United States Patent
Potyrailo et al.

(10) Patent No.: US 10,539,524 B2
(45) Date of Patent: Jan. 21, 2020

(54) RESONANT SENSING SYSTEM AND METHOD FOR MONITORING PROPERTIES OF AN INDUSTRIAL FLUID

(71) Applicant: General Electric Company, Schenectady, NY (US)

(72) Inventors: Radislav Alexandrovich Potyrailo, Niskayuna, NY (US); Igor Tokarev, Niskayuna, NY (US); Najeeb M. Kuzhiyil, McKinney, TX (US); Pradheepram Ottikkutti, Erie, PA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 369 days.

(21) Appl. No.: 15/418,820

(22) Filed: Jan. 30, 2017

(65) Prior Publication Data

US 2017/0138876 A1    May 18, 2017

Related U.S. Application Data

(63) Continuation-in-part of application No. 14/866,320, filed on Sep. 25, 2015, now Pat. No. 10,018,613,
(Continued)

(51) Int. Cl.
*G01N 27/02* (2006.01)
*G01N 33/28* (2006.01)

(52) U.S. Cl.
CPC ....... *G01N 27/026* (2013.01); *G01N 33/2847* (2013.01); *G01N 33/2888* (2013.01)

(58) Field of Classification Search
CPC ............. G01N 27/026; G01N 33/2847; G01N 33/2876; G01N 33/2888
See application file for complete search history.

(56) References Cited

U.S. PATENT DOCUMENTS

| | | | | |
|---|---|---|---|---|
| 6,028,433 | A | * | 2/2000 | Cheiky-Zelina ... G01N 33/2888 324/663 |
| 6,268,737 | B1 | * | 7/2001 | Marszalek ........... G01N 27/221 324/658 |

(Continued)

FOREIGN PATENT DOCUMENTS

DE    102007042507 A1    3/2009

OTHER PUBLICATIONS

Potyrailo, R. A., "Multivariable Sensors for Ubiquitous Monitoring of Gases in the Era of Internet of Things and Industrial Internet", Chemical Reviews, Sep. 7, 2016, 116, pp. 11877-11923, American Chemical Society, (47 pages).

(Continued)

*Primary Examiner* — Natalie Huls
(74) *Attorney, Agent, or Firm* — Philip S. Hof; The Small Patent Law Group LLC

(57) ABSTRACT

A sensing system includes a sensor and one or more processors. The sensor includes a sensing region in contact with an industrial fluid. The sensing region includes electrodes and a sensing region circuit electrically connected to the electrodes. The sensing region circuit generates an electrical stimulus having multiple different frequencies that are applied to the industrial fluid via the electrodes. The one or more processors receive one or more electrical signals from the sensor representative of an impedance response of the sensing region to the electrical stimulus. The one or more processors analyze the impedance response and determine at least one of a contaminant concentration of an external contaminant in the industrial fluid, an acid concentration of acidic components in the industrial fluid, or a base concentration of basic components in the industrial fluid based on the impedance response.

22 Claims, 51 Drawing Sheets

Related U.S. Application Data which is a continuation-in-part of application No. 14/421,245, filed on Feb. 12, 2015, now Pat. No. 9,746,452, and a continuation-in-part of application No. 14/585,690, filed on Dec. 30, 2014, and a continuation-in-part of application No. 11/560,476, filed on Nov. 16, 2006, now Pat. No. 9,589,686, and a continuation-in-part of application No. 12/325,653, filed on Dec. 1, 2008, now abandoned, and a continuation-in-part of application No. 12/824,436, filed on Jun. 28, 2010, now abandoned, and a continuation-in-part of application No. 12/827,623, filed on Jun. 30, 2010, now Pat. No. 8,936,191, and a continuation-in-part of application No. 12/977,568, filed on Dec. 23, 2010, now abandoned, and a continuation-in-part of application No. 13/331,003, filed on Dec. 20, 2011, now Pat. No. 9,045,973, and a continuation-in-part of application No. 13/484,674, filed on May 31, 2012, now Pat. No. 9,052,263, and a continuation-in-part of application No. 13/538,570, filed on Jun. 29, 2012, now Pat. No. 9,538,657, and a continuation-in-part of application No. 13/558,499, filed on Jul. 26, 2012, now Pat. No. 9,195,925, and a continuation-in-part of application No. 13/630,939, filed on Sep. 28, 2012, now Pat. No. 9,389,260, and a continuation-in-part of application No. 13/630,954, filed on Sep. 28, 2012, now Pat. No. 9,147,144, and a continuation-in-part of application No. 13/630,587, filed on Sep. 28, 2012, now Pat. No. 9,658,178, and a continuation-in-part of application No. 13/630,739, filed on Sep. 28, 2012, now Pat. No. 9,176,083, and a continuation-in-part of application No. 13/729,800, filed on Dec. 28, 2012, now Pat. No. 9,097,639, and a continuation-in-part of application No. 13/729,851, filed on Dec. 28, 2012, now Pat. No. 9,261,474, and a continuation-in-part of application No. 13/838,884, filed on Mar. 15, 2013, now Pat. No. 9,389,296, and a continuation-in-part of application No. 14/031,951, filed on Sep. 19, 2013, now Pat. No. 9,037,418, and a continuation-in-part of application No. 14/031,965, filed on Sep. 19, 2013, now Pat. No. 8,990,025, which is a continuation-in-part of application No. 14/532,168, filed on Nov. 4, 2014, now Pat. No. 9,536,122, said application No. 13/484,674 is a continuation-in-part of application No. 12/424,016, filed on Apr. 15, 2009, now Pat. No. 8,364,419.

(60) Provisional application No. 61/692,230, filed on Aug. 22, 2012, provisional application No. 61/987,853, filed on May 2, 2014.

(56) References Cited

U.S. PATENT DOCUMENTS

| | | | | |
|---|---|---|---|---|
| 6,577,140 | B1* | 6/2003 | Wenman | G01N 33/2876 |
| | | | | 324/204 |
| 6,949,936 | B2* | 9/2005 | Stone | G01N 33/2858 |
| | | | | 324/633 |
| 7,317,989 | B2 | 1/2008 | Difoggio et al. | |
| 7,562,557 | B2 | 7/2009 | Bennett et al. | |
| 7,911,345 | B2 | 3/2011 | Potyrailo et al. | |
| 7,928,741 | B2* | 4/2011 | Hedges | G01N 33/2888 |
| | | | | 324/698 |
| 8,318,099 | B2 | 11/2012 | Potyrailo et al. | |
| 8,547,110 | B2* | 10/2013 | Kesil | G01N 27/023 |
| | | | | 324/633 |
| 8,643,388 | B2 | 2/2014 | Hedges | |
| 8,833,145 | B2 | 9/2014 | Fischer et al. | |
| 8,936,191 | B2 | 1/2015 | Potyrailo et al. | |
| 9,147,144 | B2 | 9/2015 | Potyrailo et al. | |
| 9,176,083 | B2 | 11/2015 | Surman et al. | |
| 9,261,474 | B2 | 2/2016 | Potyrailo et al. | |
| 9,316,318 | B2 | 4/2016 | Ziegler | |
| 10,018,613 | B2* | 7/2018 | Potyrailo | G01N 33/2888 |
| 2003/0222656 | A1* | 12/2003 | Phillips | G01N 27/02 |
| | | | | 324/605 |
| 2004/0074303 | A1* | 4/2004 | Matsiev | G01H 13/00 |
| | | | | 73/579 |
| 2005/0179449 | A1* | 8/2005 | Wooton | G01N 33/2888 |
| | | | | 324/691 |
| 2006/0105467 | A1* | 5/2006 | Niksa | G01N 27/126 |
| | | | | 436/150 |
| 2007/0084271 | A1* | 4/2007 | Boyle | G01N 33/2876 |
| | | | | 73/53.05 |
| 2009/0001997 | A1* | 1/2009 | Lin | G01N 27/023 |
| | | | | 324/675 |
| 2009/0120169 | A1 | 5/2009 | Chandler et al. | |
| 2009/0216471 | A1* | 8/2009 | Akiyama | G01N 27/221 |
| | | | | 702/65 |
| 2012/0116683 | A1 | 5/2012 | Potyrailo et al. | |
| 2012/0161787 | A1 | 6/2012 | Potyrailo et al. | |
| 2012/0235690 | A1 | 9/2012 | Potyrailo et al. | |
| 2014/0000540 | A1* | 1/2014 | Russo | C10L 10/08 |
| | | | | 123/1 A |
| 2015/0115983 | A1 | 4/2015 | Potyrailo et al. | |
| 2015/0192558 | A1* | 7/2015 | De Coninck | G01N 29/022 |
| | | | | 73/61.49 |
| 2016/0018381 | A1 | 1/2016 | Potyrailo et al. | |
| 2016/0187277 | A1 | 6/2016 | Potyrailo et al. | |

OTHER PUBLICATIONS

Wang et al., "The Application of A.C. Impedance Technique for Detecting Glycol Contamination in Engine Oil", Sens. Actuators B, pp. 193-197, vol. 40, 1997.

Basu et al., "Smart Sensing of Oil Degradation and Oil Level Measurements in Gasoline Engines", SAE Technical Paper Series 2000-01-1366, 2000.

Foster et al., "Detection of Trace Levels of Water in Oil by Photoacoustic Spectroscopy", Sens. Actuators B, pp. 620-624, vol. 77, 2001.

Lvovich et al., "Electrochemical monitoring of water-surfactant interactions in industrial lubricants", J. Electroanal. Chem., pp. 171-180, vol. 534, 2002.

Wang et al., "Engine oil condition sensor: method for establishing correlation with total acid number", Sensors and Actuators B: Chemical, pp. 122-126, vol. 86, 2002.

Wang et al., "A New Technique for Detecting Antifreeze in Engine Oil During Early Stage of Leakage", Sens. Actuators B, pp. 157-164, vol. 96, 2003.

Buhrdorf et al., "Multiparameteric Oil Condition Sensor Based on the Tuning Fork Technology for Automotive Applications", in Advanced Microsystems for Automotive Applications, pp. 289-298, 2005.

Hempel et al., "Application of a Portable RF Impedance Spectrum Analyzer for the Investigation of Lateral Field Excited Acoustic Wave Sensors in a Liquid Environment", Proceedings—IEEE Ultrasonics Symposium, pp. 373-376, 2007.

Ulrich et al., "Simultaneous Estimation of Soot and Diesel Contamination in Engine Oil Using Electrochemical Impedance Spectroscopy", Sens. Actuators B, vol. 127, pp. 613-618, 2007.

Guan et al., "Engine Lubricating Oil Classification by SAE Grade and Source Based on Dielectric Spectroscopy Data", Anal. Chim. Acta, pp. 117-120, vol. 628, 2008.

Hempel et al., "Lateral field excited quartz crystal resonator sensors for determination of acoustic and electrical properties of liquids", IEEE International Frequency Control Symposium, pp. 705-710, 2008.

McCann et al., "Recent Advances in Lateral Field Excited and Monolithic Spiral Coil Acoustic Transduction Bulk Acoustic Wave Sensor Platforms", Meas. Sci. Tech., vol. 20, art. No. 124001, 2009.

(56) References Cited

OTHER PUBLICATIONS

Cho et al., "Capacitive Sensor for Automotive Engine Oil Degradation using Wireless Network", International Symposium on Advanced Packaging Materials: Microtech, APM '10, pp. 88-91, 2010.
Wang et al., "Impedance Analysis for Lateral Field Excited Acoustic Wave Sensors", Sens. Actuators B, pp. 969-975, vol. 156, 2011.
Liu et al., "Measurement of Density and Viscosity of Dodecane and Decane with a Piezoelectric Tuning Fork Over 298-448 K and 0.1-137.9 MPa", Sens. Actuators A 2011, pp. 347-353, vol. 167, 2011.
Latif et al., "Conductometric Sensors for Monitoring Degradation of Automotive Engine Oil", Sensors, pp. 8611-8625, vol. 11, 2011.
Guan et al., "Application of Dielectric Spectroscopy for Engine Lubricating Oil Degradation Monitoring", Sensors Actuators A, pp. 22-29, vol. 168, 2011.
Pérez et al., Low-cost Oil Quality Sensor Based on Changes in Complex Permittivity, Sensors, pp. 10675-10690, vol. 11, C:\Users\useer\Downloads\sensors-11-10675.pdf, 2011.
Fochtmann et al., "Optimization of the Lateral Field Excited Platform for Liquid Sensing Applications", Sensors Actuators B, pp. 95-103, vol. 170, 2012.
De Souza et al., "A Close Dielectric Spectroscopic Analysis of Diesel/Biodiesel Blends and Potential Dielectric Approaches for Biodiesel Content Assessment", Fuel Cells, pp. 705-710, vol. 105, 2013.
Soleimani et al., "Base Oil Oxidation Detection Using Novel Chemical Sensors and Impedance Spectroscopy Measurements", Sensors Actuators B, pp. 247-258, vol. 199, 2014.
Toledo et al., "Application of quartz tuning forks and extensional microresonators for viscosity and density measurements in oil/fuel mixtures", Microsyst. Technol., pp. 945-953, vol. 20, 2014.
Zhu et al., "An Integrated Lubricant Oil Conditioning Sensor Using Signal Multiplexing", J. Micromech. Microeng, vol. 25, 015006, 2015.
Poseidon Systems, LCC, Oil quality monitor Trident QM210, http://www.poseidonsys.com/products/oil-quality.
Tan Delta Systems Ltd., Oil quality sensor, http://www.tandeltasystems.com/products-oqs.php.
Foster-Mills et al., "Photoacoustic Spectroscopy Detects Water in Oil", Sensors Online, Oct. 2001r, http://archives.sensorsmag.com/articles/1001/12/pf_main.shtml.

\* cited by examiner

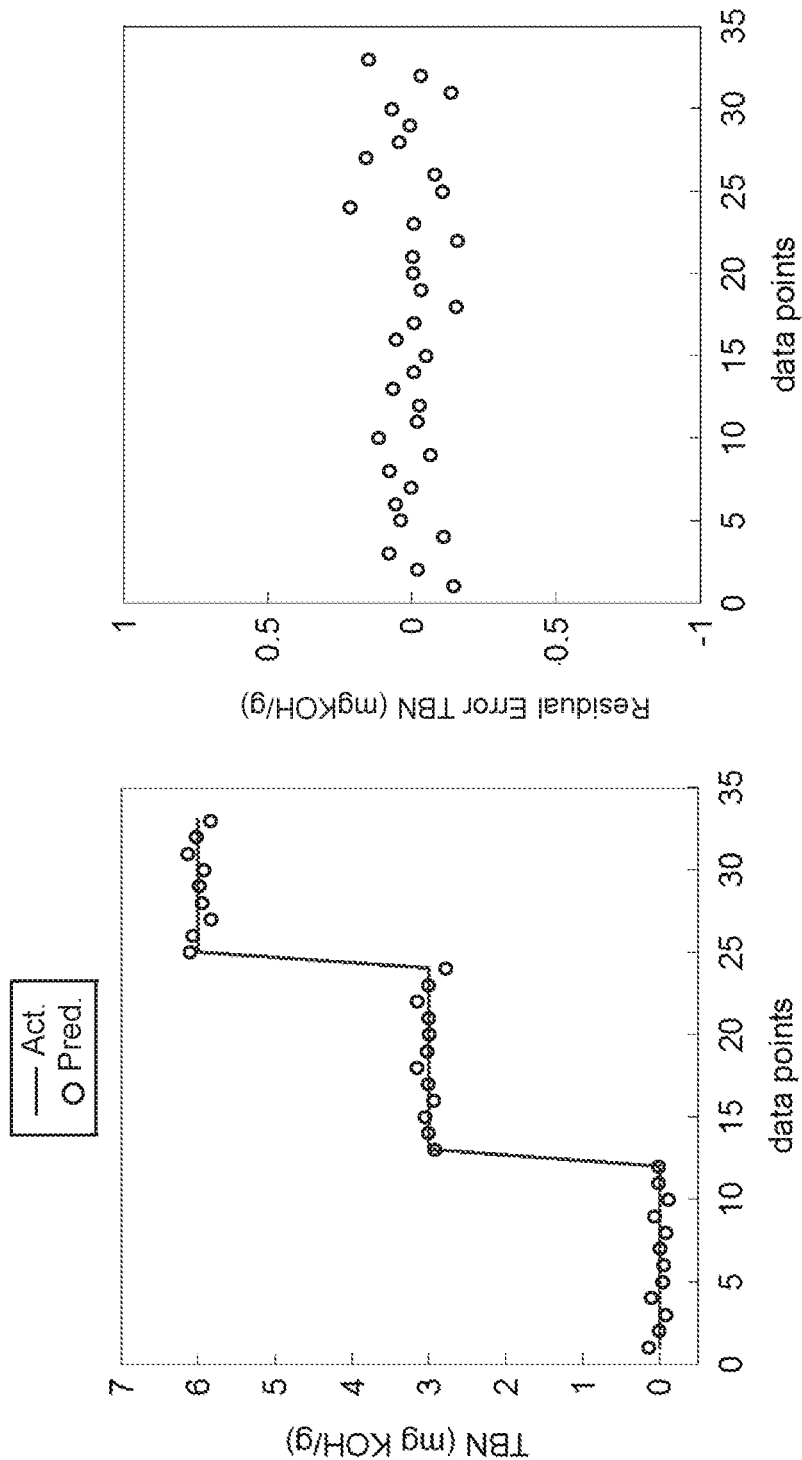

RESONANT SENSING SYSTEM AND METHOD FOR MONITORING PROPERTIES OF AN INDUSTRIAL FLUID

CROSS-REFERENCE TO RELATED APPLICATIONS

This application is a continuation-in-part of U.S. patent application Ser. No. 14/866,320, filed on 25 Sep. 2015 (the "'320 application").

The '320 application is a continuation-in-part of U.S. patent application Ser. No. 14/421,245, filed on 12 Feb. 2015 (the "'245 application"), which claims the benefit of U.S. Provisional Patent Application No. 61/692,230, filed on 22 Aug. 2012 (the "'230 application").

The '320 application also is a continuation-in-part of U.S. patent application Ser. No. 14/585,690, filed on 30 Dec. 2014 (the "'690 application"), which claims priority to U.S. Provisional Patent Application No. 61/987,853, filed on 2 May 2014 (the "'853 application"). The '690 application is a continuation-in-part of the following applications: U.S. patent application Ser. No. 11/560,476, filed on 16 Nov. 2006 (the "'476 application"), U.S. patent application Ser. No. 12/325,653, filed on 1 Dec. 2008 (the "'653 application"), U.S. patent application Ser. No. 12/824,436, filed on 28 Jun. 2010 (the "'436 application"), U.S. patent application Ser. No. 12/827,623, filed on 30 Jun. 2010 (the "'623 application"), U.S. patent application Ser. No. 12/977,568, filed on 23 Dec. 2010 (the "'568 application"), U.S. patent application Ser. No. 13/331,003, filed on 20 Dec. 2011 (the "'003 application"), U.S. patent application Ser. No. 13/484,674, filed on 31 May 2012 (the "'674 application"), U.S. patent application Ser. No. 13/538,570, filed on 29 Jun. 2012 (the "'570 application"), U.S. patent application Ser. No. 13/558,499, filed on 26 Jul. 2012 (the "'499 application"), U.S. patent application Ser. No. 13/630,939, filed on 28 Sep. 2012 (the "'939 application"), U.S. patent application Ser. No. 13/630,954, filed on 28 Sep. 2012 (the "'954 application"), U.S. patent application Ser. No. 13/630,587, filed on 28 Sep. 2012 (the "'587 application"), U.S. patent application Ser. No. 13/630,739, filed on 28 Sep. 2012 (the "'739 application"), U.S. patent application Ser. No. 13/729,800, filed on 28 Dec. 2012 (the "'800 application"), U.S. patent application Ser. No. 13/729,851, filed on 28 Dec. 2012 (the "'851 application"), U.S. patent application Ser. No. 13/838,884, filed on 15 Mar. 2013 (the "'884 application"), U.S. patent application Ser. No. 14/031,951, filed on 19 Sep. 2013 (the "'951 application"), U.S. patent application Ser. No. 14/031,965, filed on 19 Sep. 2013 (the "'965 application"), and U.S. patent application Ser. No. 14/532,168, filed on 4 Nov. 2014 (the "'168 application"). The '674 application is a continuation-in-part of U.S. patent application Ser. No. 12/424,016, filed on 15 Apr. 2009, and is now U.S. Pat. No. 8,364,419, issued on 29 Jan. 2013 (the "'419 patent").

All the aforementioned applications and patent are incorporated herein by reference in their entireties.

FIELD

One or more embodiments are disclosed that relate to sensing methods and systems. The sensors, such as resonant sensors, may include inductor-capacitor-resistor (LCR) resonant circuits that can be used as sensors or transducers for monitoring properties of fluids.

BACKGROUND

Many industrial machines (e.g., locomotives, trucks, earth-moving equipment, windmills, and the like) include elements or assemblies (e.g., mechanical drive trains) that operate within difficult environments and/or endure substantial amounts of thermal or torsional stress as well as shock and vibration. It is often desirable to monitor a condition of an element or assembly so that it may be replaced or repaired before severe and permanent damage is sustained by the machine. Often, fluid lubricants are used to provide lubrication and cooling to increase performance of the machine and/or to increase the lifetime operation of the machine. Lubricants reduce the friction between two parts that engage each other and may also dissipate heat that is generated by the friction between the two parts. In addition to lubricants, fluids include other industrial fluid such as fuels, hydraulic media, drive fluids, power steering fluids, power brake fluids, drilling fluids, oils, insulating fluids, heat transfer fluids, or the like. Such fluids allow efficient and safe operation of machinery in transportation, industrial, locomotive, marine, automotive, construction, medical, and other applications. Fluids also include naturally occurring fluids such as oils, water, body fluids, biological fluids, and the like that occur in natural living and non-living systems.

The quality of a lubricant may decrease over time due to the introduction of contaminants and/or aging of the lubricant. Lubricants in a reservoir can become contaminated by contaminants such as water, metallic particles, and non-metallic particles. Contaminated fluids may lead to damaged parts or a decreased performance of the machine. Water is a common and destructive lubricant contaminant. The water may be introduced from a coolant leak, condensation from environmental exposure, equipment cleaning, and/or combustion. Water adversely affects the lubricant properties by increasing engine wear, causing corrosion, and accelerating oil oxidation. In addition, the lubricant may age due to repetitive thermal and viscous cycles resulting in the loss of fluid properties such as viscosity as the lubricant chemically breaks down. Furthermore, stabilizing additives that are added to the lubricants to provide increased resilience within harsh environments, such as high temperatures, may begin to break down. The reduction in additive concentration provides less thermal stability for the lubricant, causing the lubricant to degrade faster over time. As the additive is depleted, acidic components, such as by-products from the degradation of the oil or additive, may be introduced into the lubricant fluid. The acidic components are contaminants that reduce the effectiveness or performance of the lubricant. Typical combustion engines (reciprocating & rotating turbine) during the combustion process create acidic by-products such as oxides of nitrogen and oxides of sulfur which enter the lubricating oil in the power cylinder or power turbine. These acidic components deplete the basic additives that are present in the lubricating oil during the life of the engine.

Conventional methods of inspecting fluids of a machine include visual inspection of the fluid (e.g., dipsticks) or a sensor that is directly wired to a system. These methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

Robust sensing of fluids may be useful in mobile and stationary equipment applications. As an example, if the equipment is a vehicle engine and the fluid is engine oil, then knowledge about oil health may be used to help reduce or prevent unexpected downtime, provide savings from unnecessary oil replacement, and improve service intervals scheduling in vehicles such as locomotives, heavy and light duty trucks; mining, construction, and agriculture vehicles. Other examples of stationary equipment applications may include wind turbines and gensets. Further, knowledge about engine oil health may prevent or reduce the total life cost of passenger cars, improve control of service intervals, and extend the life of engine.

Standard (classic) impedance spectroscopy is a technique that is employed to characterize aspects of material performance. In classic impedance spectroscopy, a material may be positioned between electrodes and probed over a wide frequency range (from a fraction of Hz to tens of GHz) to extract the fundamental information about dielectric properties of the material. Standard impedance spectroscopy may be limited due to its low sensitivity in reported measurement configurations and prohibitively long acquisition times over the broad frequency range. Therefore, standard impedance spectroscopy is difficult to perform in the field.

It may be desirable to have systems and methods for in-situ monitoring of fluid properties that differ from those systems and methods that are currently available.

BRIEF DESCRIPTION

In one or more embodiments, a sensing system (e.g., for monitoring properties of industrial fluids) is provided that includes a sensor and one or more processors. The sensor includes a sensing region configured to be in contact with an industrial fluid. The sensing region includes electrodes and a sensing region circuit electrically connected to the electrodes. The sensing region circuit is configured to generate an electrical stimulus having multiple different frequencies that are applied to the industrial fluid via the electrodes. The one or more processors are configured to receive one or more electrical signals from the sensor representative of an impedance response of the sensing region to the electrical stimulus. The one or more processors are configured to analyze the impedance response and determine at least one of a contaminant concentration of an external contaminant in the industrial fluid, an acid concentration of acidic components in the industrial fluid, or a base concentration of basic components in the industrial fluid based on the impedance response.

In one or more embodiments, a method (e.g., for monitoring properties of an industrial fluid) is provided that includes applying an electrical stimulus having multiple different frequencies to an industrial fluid via electrodes of a sensor that is in contact with the industrial fluid. The electrical stimulus is generated by a sensing region circuit of the sensor that is electrically connected to the electrodes. The method also includes receiving one or more electrical signals from the sensor at one or more processors. The one or more electrical signals are representative of an impedance response of the sensor to the electrical stimulus. The method further includes analyzing the impedance response using the one or more processors to determine at least one of a contaminant concentration of an external contaminant in the industrial fluid, an acid concentration of acidic components in the industrial fluid, or a base concentration of basic components in the industrial fluid based on the impedance response.

In one or more embodiments, a sensing system (e.g., for monitoring properties of industrial fluids) is provided that includes a sensor and one or more processors. The sensor includes a sensing region configured to be in contact with an industrial fluid. The sensing region includes electrodes and a sensing region circuit electrically connected to the electrodes. The sensing region circuit includes an inductor-capacitor-resistor (LCR) resonant circuit. The sensing region circuit is configured to generate an electrical stimulus having multiple different frequencies that is applied to the industrial fluid via the electrodes. The one or more processors are configured to receive one or more electrical signals from the sensor representative of an impedance response of the sensing region to the electrical stimulus. The one or more processors are configured to analyze the impedance response and determine a contaminant concentration of an external contaminant in the industrial fluid, a base concentration of basic components in the industrial fluid, and an acid concentration of acidic components in the industrial fluid based on the impedance response.

BRIEF DESCRIPTION OF THE DRAWINGS

FIGS. 74A-B plot the results of predicted and actual TBN levels for the different samples of oil tested using the multivariable resonant sensor and the residual error of the TBN prediction, respectively.

DETAILED DESCRIPTION

Figure 1:
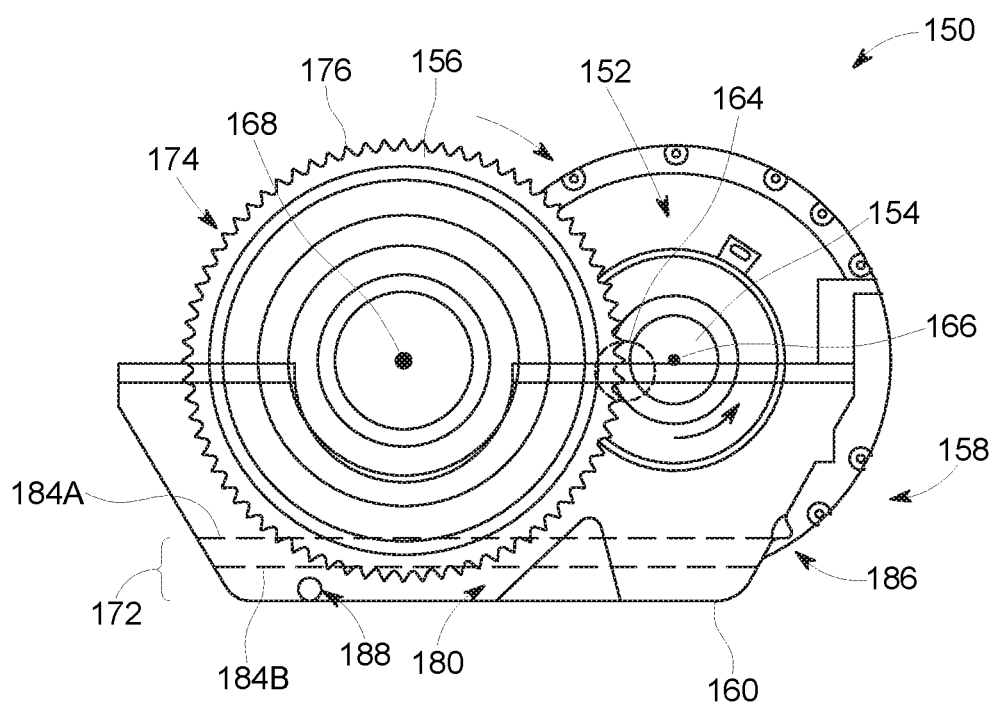
FIG. 1 is a side view of a drive train in accordance with an embodiment.

Embodiments described herein include various systems, assemblies, devices, apparatuses, and methods that may be used in a connection with obtaining one or more measurements of a machine. The measurement(s) may be representative or indicative of an operative condition of the machine. As used herein, an "operative condition of the machine" may refer to an operative condition of the machine as a whole or an operative condition of a component (e.g., element, assembly, or sub-system) of the machine. As used herein, the term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to locomotives or other rail vehicles, one or more measurements obtained from a locomotive or other rail vehicle may indicate that a lubricant in the component (e.g., drive train, gearbox, engine, and the like) is low or has an insufficient quality.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a side view of a drive train (or final drive) 150 in accordance with one embodiment. The drive train 150 includes a traction motor 152, a first (or pinion) gear 154, a second gear 156, and a base portion or shell 160 of a gear case 158. As shown in FIG. 1, the first gear 154 and the second gear 156 engage each other at a gear mesh 164. During operation of the drive train 150 the traction motor 152 drives the first gear 154 by rotating an axle (not shown) coupled to the first gear 154 about an axis of rotation 166. The first gear 154 may be rotated, for example, in a counter-clockwise direction as viewed in FIG. 1. Due to the engagement at the gear mesh 164, the first gear 154 rotates the second gear 156 in a clockwise direction about an axis of rotation 168. The second gear 156 is coupled to an axle (not shown) of a machine (not shown) that rotates with the second gear 156. The machine may be a motive machine, such that the axle of the second gear 156 is coupled to wheels (not shown) of the machine that are rotated with the axle. The wheels engage a surface (e.g., rails or tracks) to move the machine. The machine may be an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In alternative embodiments, the machine is not configured to travel. For example, the machine may be a windmill or a power-generating turbine or a transformer.

The gear case 158 includes a reservoir 172 that is configured to hold a lubricant liquid 180 (e.g., oil). The gear case 158 has a fill or inlet port 186 and a drain or outlet port 188. The liquid 180 may be provided to the reservoir 172 through the fill port 186 and drained through the drain port 188.

As shown in FIG. 1, the second gear 156 has teeth 176 along an edge 174 of the second gear 156. When the liquid 180 is held within the gear case 158, the liquid 180 may have a fill level 184. FIG. 1 illustrates a first fill level 184A and a second fill level 184B. The second fill level 184B is lower than the first fill level 184A. In some embodiments, when the drive train 150 is operating properly, the quantity of the liquid 180 correlates to the first fill level 184A such that the edge 174 of the second gear 156 is sufficiently submerged within or bathed by the liquid 180. However, when the fill level is lowered to, for example, the fill level 184B, the edge 174 and teeth 176 may be insufficiently lubricated. Such circumstances may occur when the gear case 158 has a leak. For example, the gear case may become worn and/or damaged over time such that the liquid 180 is permitted to escape the reservoir 172 and/or external contaminants are permitted to enter the reservoir 172.

Other embodiments described herein may be configured to detect other characteristics besides liquid level, such as quality (e.g., degree of contamination) of the liquid. Contaminants may include water, soot, acid, base/alkali, metallic particles, and/or non-metallic particles. Furthermore, embodiments are not limited to the drive train or a gear case of the drive train. For example, measurements may be obtained for any machine including moving parts that use a lubricating fluid, such as a turbo-charger, an air compressor, a combustion engine, and the like.

Additional embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance (Z) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

Non-limiting examples of signal changes of an individual sensor may include combined and simultaneous resonant impedance change, inductance change, resistance change, and capacitance change (referred to herein as electrical characteristics). Suitable sensors and systems disclosed herein may enhance the ability to measure changes in a fluid, such as engine oil or fuel, by contacting it with the sensor between the electrodes that constitute a resonant circuit of the sensor. The resonant circuit of the sensor may be an electrical resonant circuit. Other resonant circuits may include a mechanical resonator, where a change of viscosity and/or density of the fluid cause a response of the mechanical resonators.

Suitable mechanical resonators may include tuning fork resonators, thickness shear mode resonators, quartz crystal microbalance resonators, surface acoustic wave resonators, bulk acoustic wave resonators, and others. Unlike these and other mechanical resonators, the electrical resonators may be not predictably affected by the changes change of viscosity and/or density of the fluid. Instead, electrical resonators may be predictably affected by the changes in the complex permittivity of the fluid. Electrical resonators may be complicated in their design. For example, marginal oscillators require complicated multi-component circuits.

The degradation of at least some oils and lubricants may generate molecules and/or other moieties that may be relatively more polar than the oil and lubricant from which they were formed. The base oil or lubricant may include long chain hydrocarbon molecules that are weakly polar. Thus, the presence of polar contaminants may increase of one or more parts of the oil's complex permittivity.

The degradation of at least some oils and lubricants may generate molecules and/or other moieties that may be relatively low molecular weight and may be in the form of volatiles or gases. For example, an insulating oil of an oil-fitted transformer is employed to insulate and suppress corona and arcing and to serve as a coolant. However, the insulating oil gradually deteriorates under the impact of electrical, thermal and environmental stresses during the life of the transformer. Different types of gases are generated in the insulating oil depending on the deterioration processes. Examples of these gases include hydrogen, carbon monoxide, carbon dioxide, methane, ethane, ethylene, and acetylene. For example, thermal decomposition of mineral oil produces hydrogen and methane. Thermal decomposition of cellulose and other solid insulation materials produces carbon monoxide, carbon dioxide, and water vapor. Such gases are detected and monitored in real time using multivariable sensors as described in more detail below. For this application the sensor is coated with a sensing material that is responsive to one or more gases of interest. When the sensor is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

According to one aspect, the resonant transducers operate as re-configurable resonant structures and operate at multiple frequencies for monitoring of a status of fluids (and, further, for example, the health of equipment in contact with such fluids). Monitoring the health of fluids involves a determination of composition or a determination of contamination of such fluid.

Figure 17:
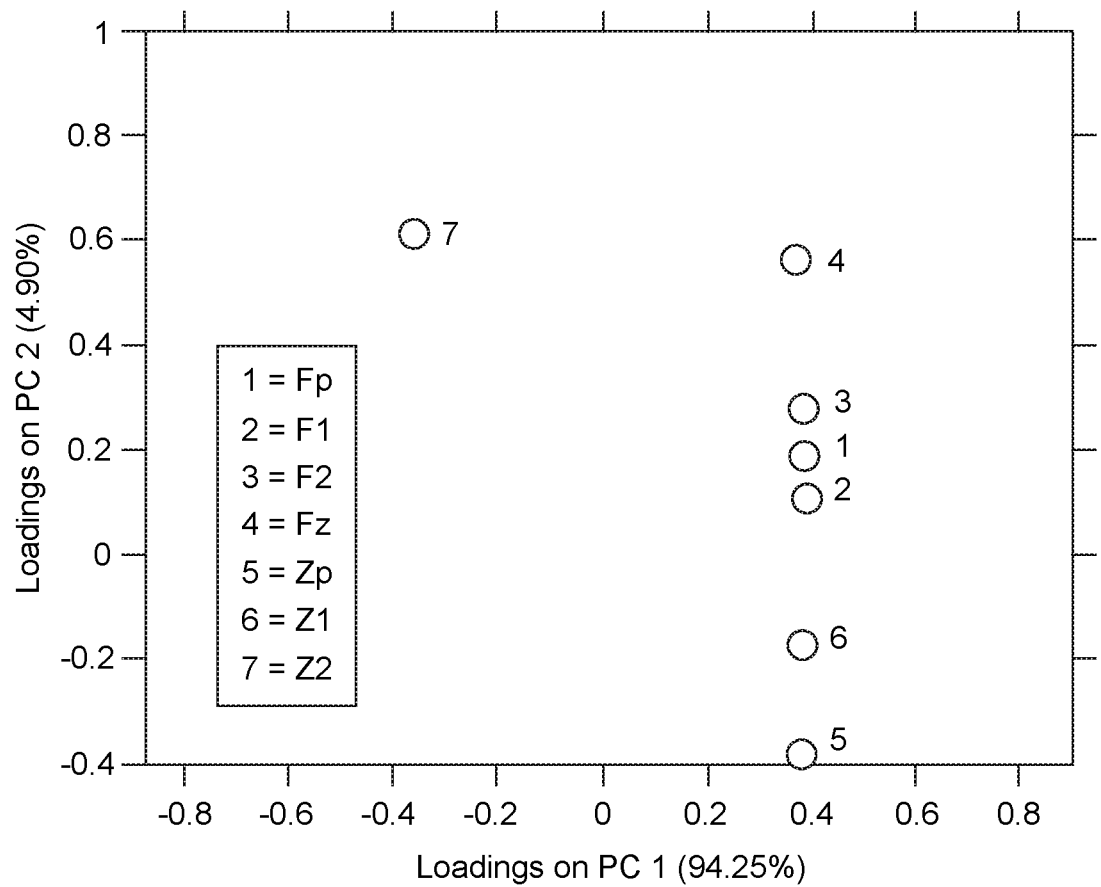
FIG. 17 is a principal components analysis of resonant impedance spectral parameters.

With reference to FIG. 17, a sensing system 1700 is shown that may be useful for assessing a fluid in contact with the sensing system 1700. For purposes of illustration, a representative fluid may be engine oil. The system may include a fluid reservoir 1712 for a fluid and a sensor 1714 disposed in, on, or within the fluid reservoir 1712. Alternatively, the sensor may be set in a flow path of the fluid outside of the reservoir 1712, such as coupled to in-line connectors in fluid communication with the fluid reservoir that define a flow path. In one embodiment, the sensor may provide continuous monitoring of the fluid within the reservoir or flow path.

Suitable fluids may include hydrocarbon fuels and lubricants. Suitable lubricants may include engine oil, gear oil, hydraulic fluid, lubricating oils, synthetic based lubricants, lubricating fluids, greases, silicones, and the like. Suitable fuels may include gasoline, diesel fuel, jet fuel or kerosene, bio-fuels, petrodiesel-biodiesel fuel blends, natural gas (liquid or compressed), and fuel oils. Still other fluids may be insulating oils in transformers, solvents, or mixtures of solvents. Still other fluids may be included with correspondingly appropriate sensor parameters, such as water, air, engine exhaust, biologic fluids, and organic and/or vegetable oils. The fluid may be a liquid, or may in in a gaseous phase. Further contemplated are multiphase compositions. The fluids may be disposed in and/or used in connection with the operation of a machine, such as a movable vehicle or a stationary machine (e.g., a wind turbine).

Non-limiting examples of various fluid components include unintended leaks from proximate systems (e.g., radiator fluid into engine oil, or water condensation in diesel fuel or transformer oil) and/or from fluid-transport devices (e.g., valves, flanges, pipes, tubes). Other detectable fluid components may include degradation products of the fluid caused by elevated temperature of operation or contact with oxidants (air, others). The operation of the system may introduce contaminants into the system, such as acids from combustion or other processes, alkaline salts (or other bases) from cleaning components of the system, dirt, salt, soot or carbon, wear metal particles, wear products, and others. For example, the base contaminants may be introduced by the process of pressure washing of various machinery (e.g., engines, gear boxes, or other machine components and sub-systems), especially when the oil reservoir develops a leak path to the ambient environment. In some environments, fouling due to bacteria or the like may be an unintended fluid component present in the industrial fluid. In all described instances, indirect measurements of the fluid, such as a pH decrease or increase that indicates an increased presence of an acidic component or increased presence of base (alkaline) components, may be useful for predicting the presence and concentration of the various fluid components. Other detectable fluid components may include external contaminants of the fluid.

The sensor may detect characteristics or properties of the fluid via a resonant impedance spectral response. One or more of the LCR resonators may measure the resonant impedance spectral response. As opposed to simple impedance measurements, the disclosed embodiments probe the sample with at least one resonant electrical circuit. The resonant impedance spectrum of the sensor in proximity to the sample (the sensor in operational contact with the fluid) varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of the resonant electrical circuit.

The electrical field may be applied by the sensor via electrodes. The electrodes may be in direct or indirect electrical contact with the sample. For example, a sensor may be a combination of a sensing region and associated circuits. The sensing region may be either bare or coated with a protective dielectric layer or a sensing layer. In each of the disclosed cases, the sensing region may be considered to be in operational contact with a fluid. In such embodiments, the sensor circuits may not contact the fluid directly. An example of indirect electrical contact with the sample may be when a sensing electrode structure is coated with a dielectric protective coating and when the electric field that may be generated between the electrodes interacts with the fluid after penetrating through the dielectric protective coating. A suitable dielectric protective coating may be conformally applied to the electrode.

Suitable sensors may include single use or multi-use sensors. A suitable multi-use resonant sensor may be a re-usable sensor that may be used during the lifetime of a system in which it may be incorporated into. In one embodiment, the resonant sensor may be a single use sensor that may be used during all or part of a reaction or process. For example, the resonant sensor may include one or more pairs of electrodes and one or more tuning elements, e.g., a resistor, a capacitor, an inductor, a resonator, impedance transformer, or combinations of two or more thereof to form an inductor-capacitor-resistor (LCR) resonant circuit operated at one or more resonant frequencies. In certain embodiments, different resonant circuits of a plurality of resonant circuits of a resonant sensor may be configured to resonate at different frequencies. Different frequencies may be selected to be across the dispersion profile of the measured fluid composition. The dispersion profile may depend on the dielectric properties of the fluid composition on the probing frequency. Various components of the fluid have different dispersion profiles. When measured at multiple resonance frequencies, concentrations of different components of the fluid may be determined.

Figure 3:
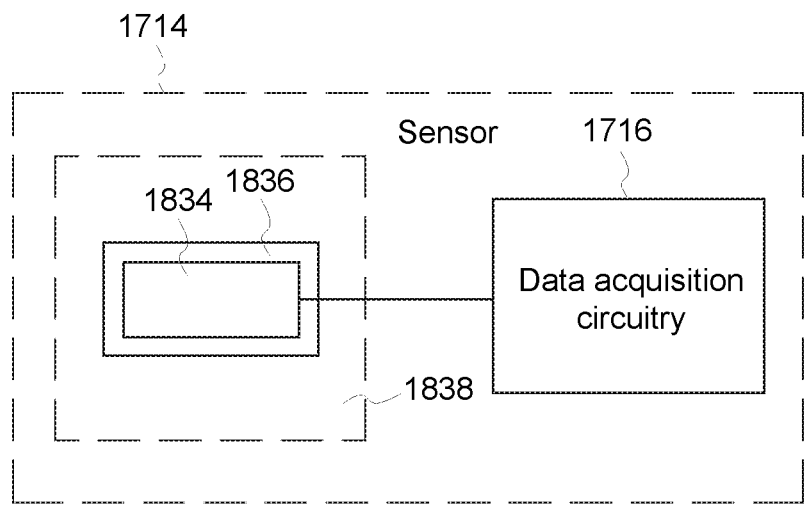
FIG. 3 is a schematic view of a resonant sensor according to an embodiment of the disclosure.

Data from the resonant sensor may be acquired via data acquisition circuitry 1716, which may be associated with the sensor or which may be associated with a control system, such as a controller or workstation 1722 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as RFID wireless communications. Other wireless communication modalities may be used based on application specific parameters. For example, where there may be EMF interference certain modalities may work where others may not. The data acquisition circuitry can be disposed within the sensor 1714 as shown in FIG. 3. Other suitable locations may include disposition being within the workstation. Further, the workstation can be replaced with a control system of the whole process where the resonant sensor and its data acquisition circuitry may be connected to the control system of process.

The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more resonant sensors 1714 (e.g., multiple sensors formed in an array or multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. The sensors may be positioned on or in fuel or fluid reservoirs, associated piping components, connectors, flow-through components, and any other relevant process components. The data acquisition circuitry may include one or more processors for analyzing the data received from the sensor 1714. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

In addition to displaying the data, the operator workstation may control the above-described operations and functions of the system. The operator workstation may include one or more processor-based components, such as general purpose or application-specific computers 1724. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 1726, keyboard 1728, electronic mouse 1730, and printer 1732 that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

The sensor 1714 may include a plurality of resonant circuits that may be configured to probe the fluid in the fluid reservoir with a plurality of frequencies. The fluid reservoir may be a reservoir bound by the engineered fluid-impermeable walls or by naturally formed fluid-impermeable walls or by the distance of the electromagnetic energy emitted from the sensor region to probe the fluid. Further, the different frequencies may be used to probe a fluid sample at different depths. In certain embodiments, an integrated circuit memory chip may be galvanically coupled to the resonant sensor. The integrated circuit memory chip may contain different types of information. Non-limiting examples of such information in the memory of the integrated circuit chip include calibration coefficients for the sensor, sensor lot number, production date, and/or end-user information. In another embodiment, the resonant sensor may comprise an interdigital structure that has a fluid-sensing region.

In certain embodiments, when an integrated circuit memory chip may be galvanically coupled to the resonant sensor, readings of the sensor response may be performed with a sensor reader that contains circuitry operable to read the analog portion of the sensor. The analog portion of the sensor may include resonant impedance. The digital portion of the sensor may include information from the integrated circuit memory chip.

FIG. 3 illustrates a non-limiting example of a design of the resonant sensor 1714. A sensing electrode structure 1834 of the sensor may be connected to the tuning circuits and the data acquisition circuitry 1716. The sensing electrode structure 1834 can be bare and in direct contact with the fluid. Alternatively, the sensing electrode structure can be coated with a protective or sensing coating 1836. The sensing electrode structure, without or with the protective or sensing coating, forms a sensing region 1838. The coating may be applied conformably, and may be a dielectric material. The sensing electrode structure, without or with the protective coating that forms the sensing region, may operationally contact a fluid. The fluid contains the analyte or contaminant(s). The sensing electrode structure may be either without (bare) or with a protective coating. A bare sensing electrode structure may generate an electric field between the electrodes that interacts directly with the fluid. A dielectric protective coated sensing electrode structure may generate an electric field that is between the electrodes that interacts with the fluid after penetrating through the dielectric protective coating. In one embodiment, the coating may be applied onto electrodes to form a conformal protective layer having the same thickness over all electrode surfaces and between electrodes on the substrate. Where a coating has been applied onto electrodes to form a protective layer, it may have a generally constant or variable final thickness over the substrate and sensor electrodes on the substrate. In another embodiment, a substrate simultaneously serves as a protective layer when the electrodes are separated from the fluid by the substrate. In this scenario, a substrate has electrodes on one side that do not directly contact the fluid, and the other side of the substrate does not have electrodes that face the fluid. Detection of the fluid may be performed when the electric field from the electrodes penetrates the substrate and into the fluid. Suitable examples of such substrate materials may include ceramic, aluminum oxide, zirconium oxide, and others.

Figure 4:
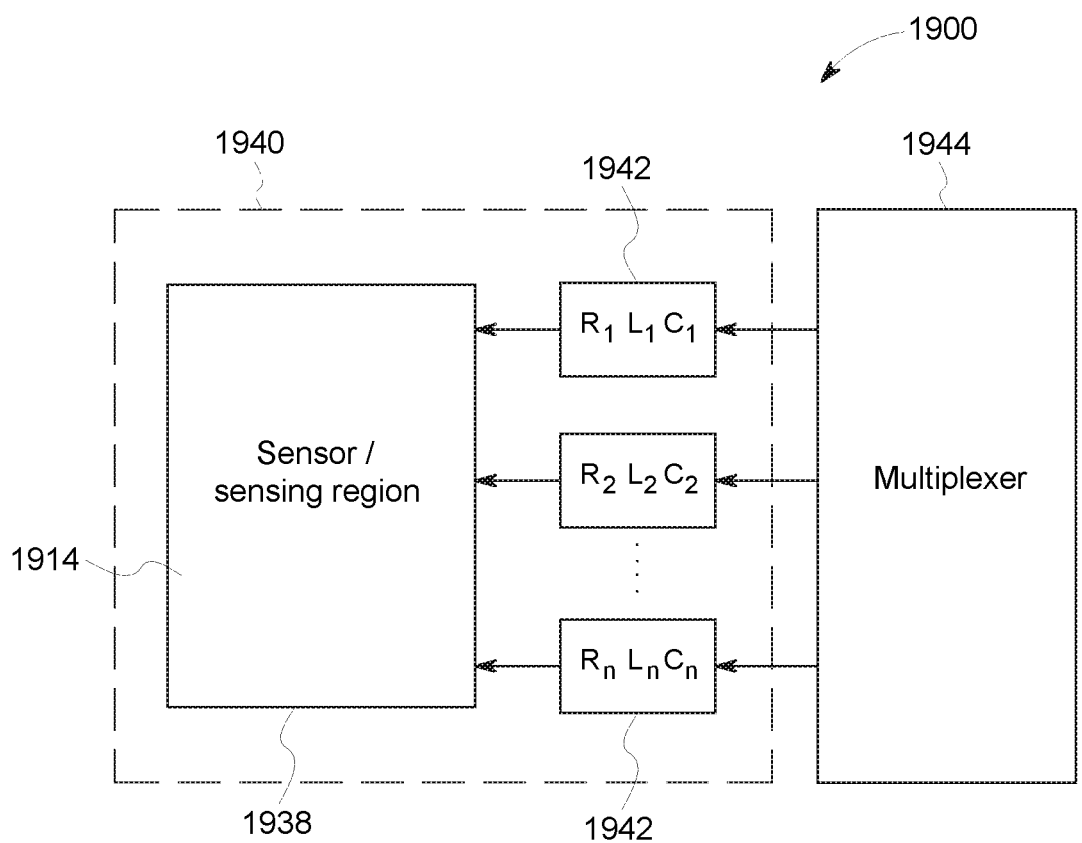
FIG. 4 is a schematic view of a portion of an example sensor system employing a sensor assembly configured for sensing of a fluid using a plurality of frequencies, in accordance with embodiments of the present disclosure.

FIG. 4 illustrates a portion of a resonant sensor system 1900 having a single sensing region 1938, and employed in a sensor assembly 1940 useful to probe a fluid sample using a plurality of frequencies. The sensing region may be disposed on a substrate and may include a suitable sensing material. In some embodiments, the substrate of the sensor may be a dielectric substrate. In some embodiments, the sensor assembly may include a plurality of tuning elements 1942. The plurality of tuning elements may be operatively coupled to the single sensing region to define a plurality of resonant circuits. The tuning elements along with the single sensing region may define a plurality of resonant circuits. Each resonant circuit of the plurality of resonant circuits may include one or more tuning elements of the plurality of tuning elements. Not shown is a semi-permeable film, semi-permeable membrane, or semi-permeable inorganic barrier (collectively a "selective barrier") that allows (or prevents) selective analytes or contaminants through the selective barrier and into the sensing region.

Suitable interdigital electrode structures for probing a fluid sample include two- and four-electrode structures. Suitable materials for electrodes include stainless steel, platinum, gold, noble metals, and others. Suitable materials of a substrate and/or a dielectric protective layer may include silicon dioxide, silicon nitride, parylene, silicone, fluorinated polymers, alumina, ceramics, and others. Suitable examples of sensing layers include semiconducting materials, metal oxides, nanocomposites, polymers, or the like. Suitable electrodes may be formed using metal etching, screen-printing, ink-jet-printing, and mask-based metal deposition techniques. The thickness of fabricated electrodes on the substrates may be in a range of from about 10 nanometers to about 1000 micrometers. The materials for the interdigital electrode structures, substrate, dielectric protective layer, sensing layer, and electrode formation methods may be selected based at least in part on the application specific parameters.

As shown in the illustrated embodiment, the plurality of tuning elements may be disposed external to the sensor. However, in one embodiment, the tuning elements may be disposed on the substrate of the sensor. In another embodiment, some of the plurality of tuning elements may be external to the sensor substrate, while other tuning elements may be disposed on the substrate. The tuning elements may comprise a resistor, a capacitor, an inductor, a resonator, impedance transformer, or combinations thereof.

The sensor assembly 1940 may include a controller that has a multiplexer 1944. The multiplexer may facilitate electronic switching between the tuning elements. The multiplexer may select one or more signals associated with the probing frequencies and forward the selected signal to an output device or a sensor reader. The multiplexer may send a plurality of signals simultaneously to a sensor reader.

During operation, each resonant circuit may resonate at a defined frequency. At least one resonant circuit may resonate at a frequency that may be different from the resonating frequency of the other resonant circuits. By way of example, if the sensing region includes a pair of electrodes, the tuning elements may be a resistor, a capacitor, and an inductor to form an inductor-capacitor-resistor (LCR) resonant circuit. The tuning elements may be electrically coupled to the sensing region. In one embodiment, the tuning elements may be in parallel connection to the sensing region. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions of fluid components. The spectral dispersions of fluid components may include spectral dispersions of external contaminants and/or acidic and/or basic components of the fluid. As used herein, basic components may refer to alkaline components, and base concentration may refer to alkali/alkaline concentration. The spectral dispersions that may be monitored with the sensors of the present disclosure may be over a frequency range of from about 0.1 Hz to about 100 GHz and include alpha, beta, gamma, delta, and other types of spectral dispersions as constrained by application specific parameters.

Figure 5:
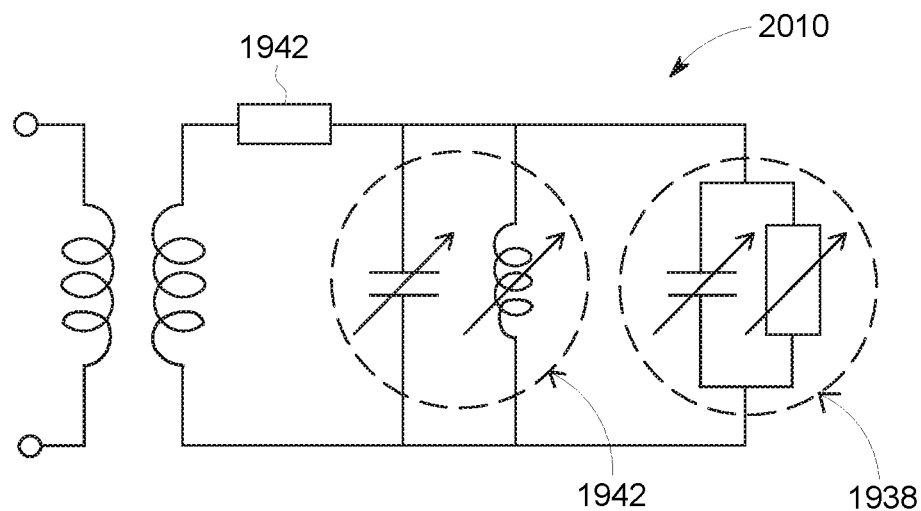
FIG. 5 is an example of an equivalent circuit of the resonant sensor according to an embodiment of the disclosure.

FIG. 5 illustrates another sensor circuit 2010. The sensing region 1938 (shown with variable resistor and capacitor) is combined with tuning components 1942 (shown with variable inductor and capacitor). To realize sensor response at a different frequency range, additional circuit elements may be utilized to tune the frequency range. Therefore, a sensor can be operating at multiple frequency ranges by using a defined or selected combination of extra circuit components—such as inductors, capacitors, and impedance transformers. These components may be connected in parallel or in series, as needed, to the sensor to vary the operating frequency range. The controller may control the impedance transformer ratio to affect the sensitivity. A sensor's frequency response and its magnitude may be based at least in part on the overall input resonant impedance changes due to the sensor's response to the fluid status, fluid behavior, and the like. Thus, the sensor's sensitivity may be controlled through the dynamic tunability of the transformer ratio. Tuning the response of each channel may be achieved, for example, by using one or more inductors. In one embodiment, wireless readout from the electrodes may provide an improvement in response selectivity and sensitivity. In one embodiment, transformer based coupling may reject parasitic LCR components from instrumentation (analyzer, cables, amongst others). The LCR resonator in FIG. 5 has a relatively simple design as compared to other resonators, for example as compared to marginal oscillators that require complicated multi-component circuits for their operation that include a current feedback amplifier and other components.

Figure 6:
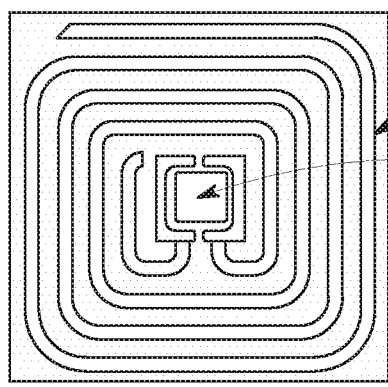
FIG. 6 is an example of an adapted radio frequency identification (RFID) tag for resonant sensing in which the sensing region constitutes a whole or a portion of the resonant antenna according to an embodiment of the disclosure.
Figure 7:
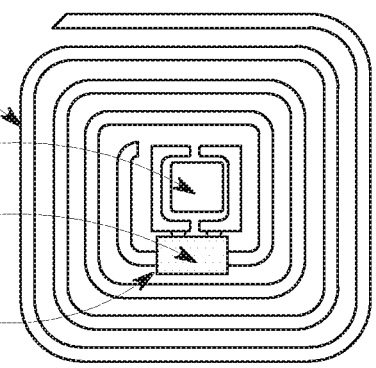
FIG. 7 is an example of an adapted RFID tag for resonant sensing in which the sensing region is in galvanic contact with the antenna and memory chip according to an embodiment of the disclosure.

As noted herein, a suitable wireless sensor may be radio-frequency identification (RFID) sensor where a passive RFID tag may be adapted to perform a sensing function. With reference to FIGS. 6 and 7, an embodiment is shown in which the resonant sensor may be an adapted RFID tag. In FIG. 6, a resonant antenna 2150 and memory chip 2152 may be coated with a protective material or sensing material 2156. The sensing material may be a sensing region of the RFID tag. In FIG. 7, the sensing region 1938 (that can optionally include the protective or sensing material) may be attached across an antenna. In both cases (e.g., both FIGS. 6 and 7), the electrical response of the sensing region may be translated into changes in the resonant impedance response of the sensor. An RFID sensor having a memory chip may operate with a frequency determined at least in part by the operating frequency used by the memory chip. That is, some operating frequencies (of the sensor and the chip) may interfere with each other and may be less desirable to have disruptive harmonics or destructive waveforms. And, the sensor can have a circular, square, cylindrical, rectangular, or other appropriately-shaped sensing region and/or antenna.

The resonant frequency of an antenna circuit may be set to a higher frequency than a resonant frequency of the sensor circuit. The frequency differential may be in a range of from, for example, as much as about 4 times to about 1000 times higher. In one embodiment, the sensor circuit may have a resonant frequency that may respond to a determined sensed environmental condition. The two resonant circuits may be connected so that when alternating current (AC) energy is received by the antenna resonant circuit, it may apply direct current energy to the sensor resonant circuit. The AC energy may be supplied through the use of a diode and a capacitor, and the AC energy may be transmitted to the sensor resonant circuit through an LC tank circuit through either a tap within the L of the LC tank circuit or a tap within the C of the LC tank circuit. Further, the two resonant circuits may be coupled such that voltage from the sensor resonant circuit may change the impedance of the antenna resonant circuit. The modulation of the impedance of the antenna circuit may be accomplished through the use of a transistor, for example a FET (field-effect transistor).

The RFID sensor's memory chip may be optional. The RFID sensor without a memory chip can be a resonant LCR sensor and can operate at different frequency ranges from a kilohertz to several gigahertz. That is, the memory chip's absence may widen the available frequency range.

Suitable sensing materials and sensing films as disclosed herein may include materials deposited onto the sensor to perform a function of predictably and reproducibly affecting the resonant impedance sensor response upon interaction with the environment. For example, a conducting polymer, such as polyaniline, changes its conductivity upon exposure to solutions of different pH. That is, the resonant impedance sensor response changes as a function of pH when such a conducting polymer film is deposited onto the RFID sensor surface. Thus, such an RFID sensor works as a pH sensor.

As an example of gaseous fluid detection, when such a polyaniline film is deposited onto the RFID sensor for detection in gas phase, the resonant impedance sensor response also changes upon exposure to basic (for example, $NH_3$) or acidic (for example, HCl) gases. Suitable sensor films include polymer, organic, inorganic, biological, composite, and nano-composite films that change their electrical and or dielectric property based on the environment in which they may be placed. Other examples of sensor films may be a sulfonated polymer such as commercially available Nafion, an adhesive polymer such as silicone adhesive, an inorganic film such as sol-gel film, a composite film such as carbon black-polyisobutylene film, a nano-composite film such as carbon nanotube-Nafion film, gold nanoparticle-polymer film, metal nanoparticle-polymer film, zeolites, metal-organic frameworks, cage compounds, clathrates, inclusion compounds, semiconducting materials, metal oxides, electrospun polymer nanofibers, electrospun inorganic nanofibers, electrospun composite nanofibers, and other sensor materials selected based on application specific parameters. To reduce or prevent the material in the sensor film from leaking into the liquid environment, the sensor materials may be attached to the sensor surface using standard techniques, such as covalent bonding, electrostatic bonding and other techniques. Some sensing materials may require a certain temperature for efficient operation. A non-limiting range of operating temperatures of the sensing materials and associated sensors onto which the sensing materials are deposited is between −260 degrees Celsius and 1600 degrees Celsius.

In one embodiment, the system may measure a resonant impedance (f) (represented by Eq. (1)) of the sensor.

$$\check{Z}(f) = Z_{re}(f) + jZ_{im}(f) \qquad \text{Eq. (1)}$$

where $Z_{re}(f)$ may be the real part of the resonant impedance and $Z_{im}(f)$ may be an imaginary part of the resonant impedance. In one embodiment, the resonant impedance spectral response of the sensor may be a multivariable response as more than one frequency may be utilized to measure sensor response across the resonance of the sensor. In some embodiments, the resonant impedance response of the sensor may be a multivariable response because more than one frequency may be utilized to measure sensor response outside the resonance peak of the sensor. In some embodiments, the sensor response may be measured at multiple frequencies across the resonance of the sensor. For example, if the sensor resonates at about 1 MHz, the measured frequencies and associated sensor responses may be measured from about 0.25 MHz to about 2 MHz. This multivariable response may be analyzed by multivariate analysis.

The multivariable response of the sensor includes the sensor's full resonant impedance spectral response and/or several individually measured parameters, such as but not limited to $F_p$, $Z_p$, $F_z$, $F_1$, $F_2$, $Z_1$, and $Z_2$. As used herein, the term "resonant impedance spectral response" may be referred to as "impedance response," "resonant impedance spectra," and/or variations thereof.

Figure 8:
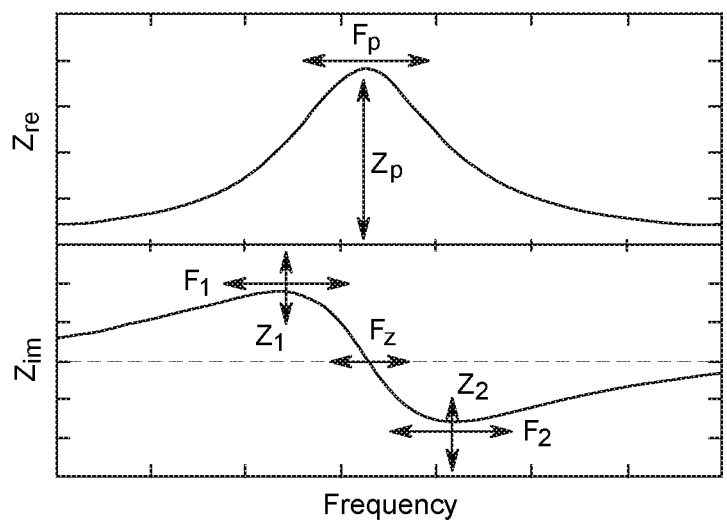
FIG. 8 is a graph of measured resonant impedance parameters of an embodiment of the resonant sensor, in accordance with embodiments of the present technique.

FIG. 8 depicts a graph of measured resonant impedance parameters of an embodiment of the resonant sensor, in accordance with embodiments of the present technique. The properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance.

Figure 9:
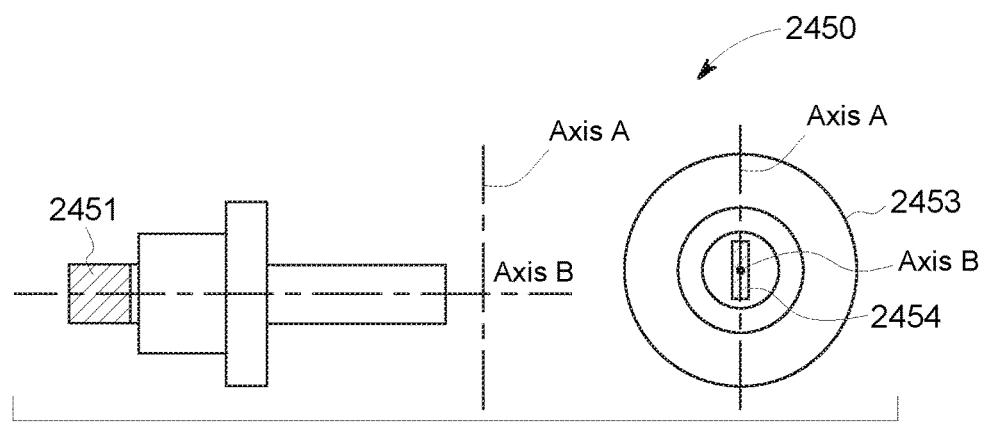
FIG. 9 is an example of a resonant sensor in which the sensing region is arranged parallel to the sensor axis insertion into the measured fluid, and therefore, perpendicular to the insertion port of the sensor according to an embodiment of the disclosure.
Figure 10:
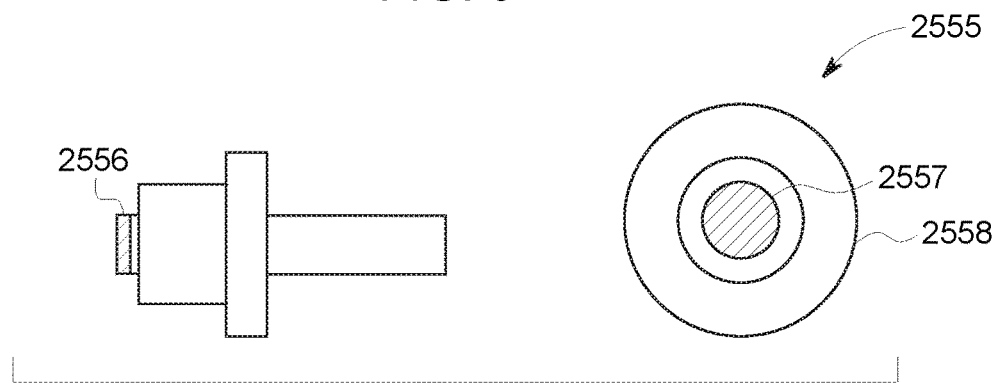
FIG. 10 is an example of a resonant sensor in which the sensing region is arranged perpendicular to the sensor axis insertion into the measured fluid, and therefore, parallel to the insertion port of the sensor according to an embodiment of the disclosure.

For measurements of fluid properties in fluid reservoirs, sensors with their sensing regions can be designed to fit standard ports or specially made ports in the reservoirs. Suitable design examples are depicted in FIG. 9 and FIG. 10. An example is provided of a resonant sensor 2450 with an aligned sensing region 2451. The sensing region defines a first Axis A, which is perpendicular to a transverse axis labeled Axis B. An insertion port structure 2453 defines an insertion aperture 2454 that is elongated along Axis A. The sensing region, then, is arranged parallel to the port's elongated aperture, translation along Axis B allows for sensor region insertion into the port and to contact a measured fluid. An example of another resonant sensor 2555 in which the sensing region 2556 is not constrained by its shape relative to an aperture 2557 defined by a port structure 2558 is depicted in FIG. 10. Alignment pins, not shown, may be used to align the sensor, and the sensing region, relative to the port aperture, as may be desired.

Figure 11:
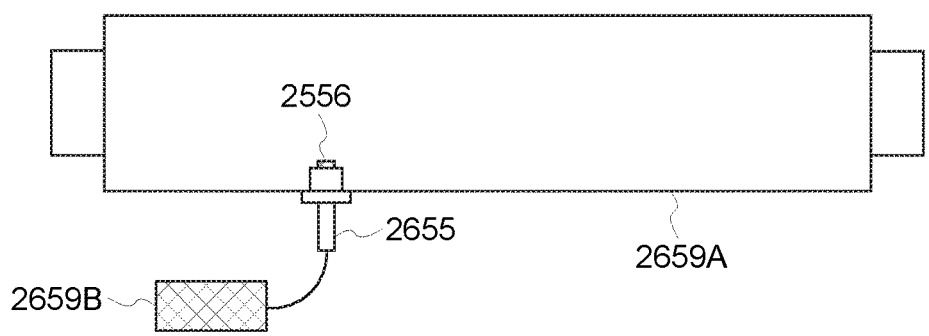
FIG. 11 is an example of sensing of fluid properties with a sensor in a fluid reservoir when the sensor is incorporated into the reservoir with the sensing region of the sensor exposed to the fluid and the sensor reader located near the sensor and connected to the sensor with a cable according to an embodiment of the disclosure.
Figure 12:
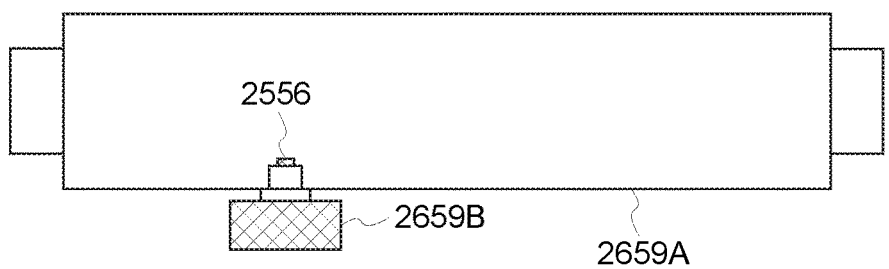
FIG. 12 is an example of sensing of fluid properties with a sensor in a fluid reservoir when the sensor is incorporated into the reservoir with the sensing region of the sensor exposed to the fluid and the sensor reader directly connected to the sensor according to an embodiment of the disclosure.

Measurements of fluid properties in fluid reservoirs may be performed using sensors with their sensing regions exposed to the fluid as shown in FIGS. 11 and 12. The sensor 2655 shown in FIG. 11 is installed in a fluid transfer pipe 2659A, and is coupled to a sensor reader 2659B. The sensor reader 2659B may be coupled by wire or cable, and located proximate to the sensor 2655 as shown in FIG. 11. In another embodiment, the sensor reader 2659B may be directly connected to the sensor without a cable—as shown in FIG. 12. During operation, a fluid flows through the pipe and contacts the sensing region 2556. As the sensing region 2556 senses an analyte of interest it signals the sensor reader 2659B.

Figures 13A, 13B, 13C:
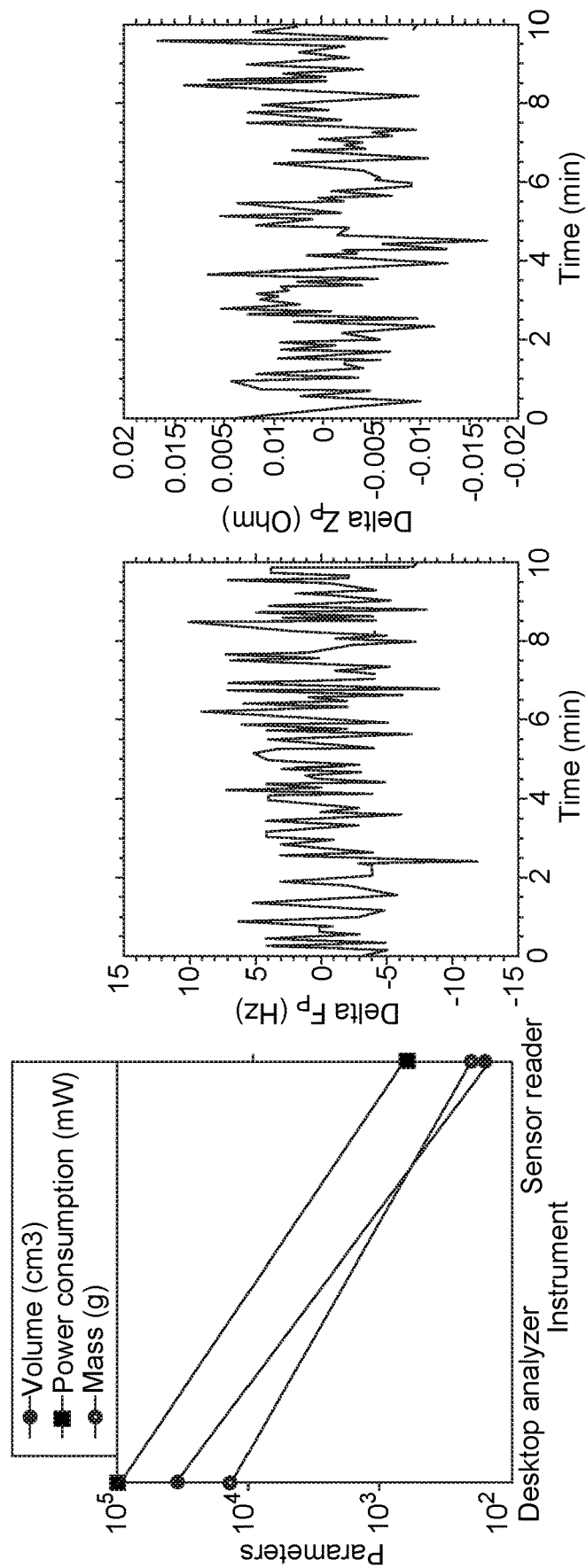
FIGS. 13A-C are graphs depicting measurements related to the sensor reader according to one embodiment.

The sensor reader (also referred to as micro-analyzer) has been developed with a small form factor, low power consumption and low cost of components. FIGS. 13A-C are graphs depicting measurements related to the sensor reader according to one embodiment. FIG. 13A is a comparison of power consumption, size, and weight between a desktop analyzer and the developed micro-analyzer. FIG. 13A depicts that the design of the micro-analyzer provided 100-500-fold reduction in power consumption, size, and weight as compared to desktop analyzers. These advancements make the sensor reader attractive for a wide range of applications including monitoring of industrial fluids, where laboratory analyzers are size-, power-, and cost-prohibitive. FIGS. 13B and 13C depict measured Fp and Zp noise levels of the developed micro-analyzer, respectively. The developed sensor reader has a $1\sigma$ Fp noise of ~5 Hz and $1\sigma$ Zp noise of 0.006 ohm. This electronic design of the sensor reader provided 4-14 times reduction in noise levels in measurements of (f) spectra as compared to measurements with a laboratory desktop analyzer with Fp noise=60 Hz and Zp noise=0.025 Ohm.

Figure 14:
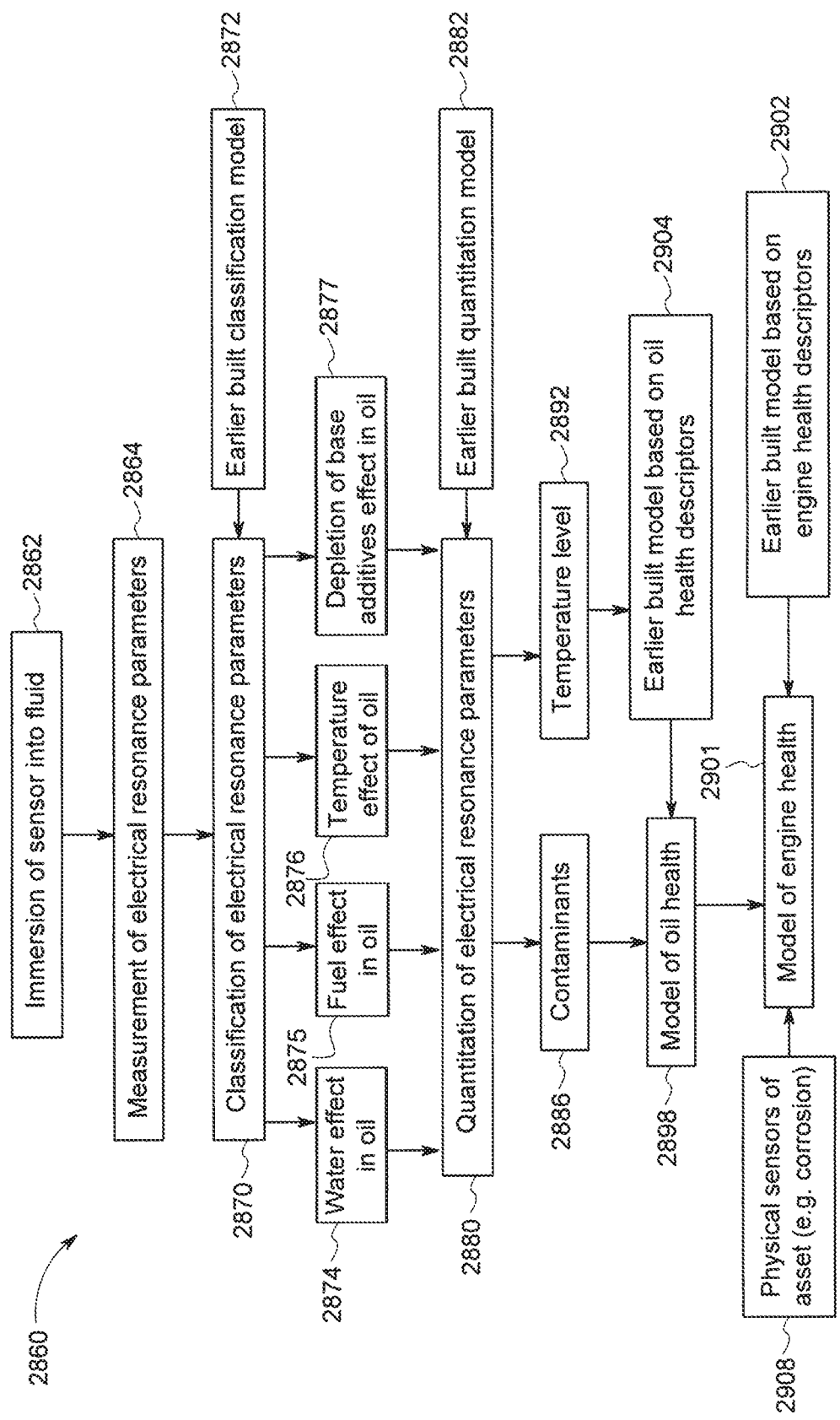
FIG. 14 is a flow diagram of fluid assessment according to an embodiment of the disclosure.

A flow diagram of a method 2860 is shown in FIG. 14. In one embodiment, a method for monitoring of oil health includes immersion of the sensor into an oil (step 2862) and measurement of electrical resonance parameters of the resonance spectra (step 2864) at several resonances of a single sensor. For quantitation of contamination of engine oil by water, fuel leaks, and soot with a sensor, the sensor may be placed into operational contact with the fluid at step 2862. In a specific embodiment, the resonant impedance spectra $(f)=Z_{re}(f)+jZ_{im}(f)$ of a sensor may be determined at step 2864. For example, the parameters from the measured (f) spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_z$ of $Z_{im}(f)$, may be calculated. In another embodiment, the electrical resonance parameters may include capacitance parameters of the sensor in operational contact with the fluid, instead or in addition to impedance parameters.

The method 2860 classifies the electrical resonance parameters at step 2870. This may be done using a determined classification model 2872 to assess, for example, one or more of water effects 2874, fuel effects 2875, temperature effects 2876, and depletion of base additives effects 2877 in oil. Quantitation of the electrical resonance parameters may be performed at step 2880 by using a predetermined, earlier saved quantitation model 2882, and determination of components 2886 in oil such as water, fuel, soot, and wear metal particles 2890 as well as the temperature 2892, and prediction of the oil health 2898 and the engine health 2901. This may be done by using one or more of determined engine health descriptors 2902 and oil health descriptors 2904 as well as inputs from any additional sensors 2908. Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameters that may be further processed upon auto scaling or mean centering of the parameters and to quantitatively determine properties of the oil. The properties of the oil that are determined via analyzing the resonance impedance spectrum may include the concentration of water, acid, base, and/or fuel in engine oil. The properties may be used to predict the remaining life of the engine oil and/or the remaining life of the engine in which the oil is disposed. The spectral parameters of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model 2872 may be built using the predicted contributions of the spectral parameters for an uncontaminated fluid and for fluid contamination using previously determined component effects and their corresponding spectral parameters. Such effects may be quantified using the quantitation model 2882 to predict if a measured or sensed fluid has any water effects, acid effects, base effects, fuel leak effects, and/or temperature effects. That is, based on previously or empirically determined effects of components on a particular fluid, the resonance parameters, both real and imaginary, may be changed and/or affected in a quantifiable manner if specific components of interest are present. Further, based on the measured parameters, a concentration of a particular component may also be predicted, and multi-component models may be generated. The disclosed techniques may be used to sense a suitable fluid and to build a component and environmental effect model.

In one embodiment, measurements of impedance parameters of fluids may be performed at two or more temperatures of the fluid. Measurements at different temperatures provide information about species of interest and other species (chemical constituents) in the fluid when measured as the frequency dispersion profiles over the broad frequency range or when measured as frequency responses over the relatively narrow frequency range. Performing analysis of resonant impedance spectra of the sensor collected at different temperatures and determining two or more properties of the fluid per temperature based on the analyzed resonant impedance spectra allows an improvement of the sensor accuracy of determinations of properties of species of interest. This improvement may be due to differences of frequency responses of species of interest and other species in the fluid as a function of temperature caused by the molecular structure of these different species. Measurements at different temperatures may be performed with a resonant sensor that has a thermal element in thermal contact with the sensing region of the resonant sensor. The thermal element produces a local change in temperature of the fluid which may be in proximity to the sensing region. This local temperature change can be above or below the temperature of the bulk of the fluid in the container with the sensor. Non-limiting examples of thermal elements include a Peltier cooler, thin-film heater, and pencil heater. The thermal element can produce a local change in temperature of the fluid in the range from about 1 degree Celsius to about 50 degrees Celsius.

In one embodiment, measurements of parameters of fluids may be performed to determine dynamic signatures of the changes of chemical constituents in the fluid. The time scales of these dynamic signatures may vary greatly. Suitable timescale in a range of from about 1 second to about 200 days may be useful to determine different types of leaks of fluids in engines. Such determinations allow the identification of dynamic signatures of the leaks in an engine, relation of the identified signature with the known leak signature from a specific engine component, and determination of the location of the leak based on the signature.

Measurements of properties of fluids may be performed at extreme temperature conditions. Depending on the application, these conditions may range from temperatures down to about −260 degrees Celsius and to temperatures up to about +1600 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +1600 degrees Celsius may be useful in monitoring equipment where the temperature of operating components of the equipment can reach about +1600 degrees Celsius. Examples of equipment that operates at about 250 degrees Celsius may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer. Examples of equipment that operates at about 1000 and up to 1500 degrees Celsius include gas turbines. Examples of equipment that operates at about 1600 degrees Celsius include aircraft jet engines.

The applicability of multivariable electrical resonators may be demonstrated by detection of engine oil contamination from water and diesel fuel and determinations of water in model fluid such as dioxane that has the dielectric constant similar to oil. Determination of resolution of the sensor measurements may be performed using hexane and toluene as model systems. Samples of some engine oil were obtained from GE Transportation, while other chemicals may be commercially obtained from Aldrich.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS Toolbox (Eigenvector Research, Inc., Manson, Wash.) operated with Matlab (The Mathworks Inc., Natick, Mass.).

Different amounts of fuel and water leaks into oil may be determined quantitatively and experimentally with a single multivariable resonant sensor. Suitable oil may be railroad internal combustion engine oil. Suitable fuel may be diesel fuel. Binary and ternary mixtures of water and fuel in oil may be produced in different proportions. Concentrations of water may be 0, 0.1% and 0.2% (by volume). Concentrations of fuel may be 0, 3% and 6% (by volume).

Figure 15:
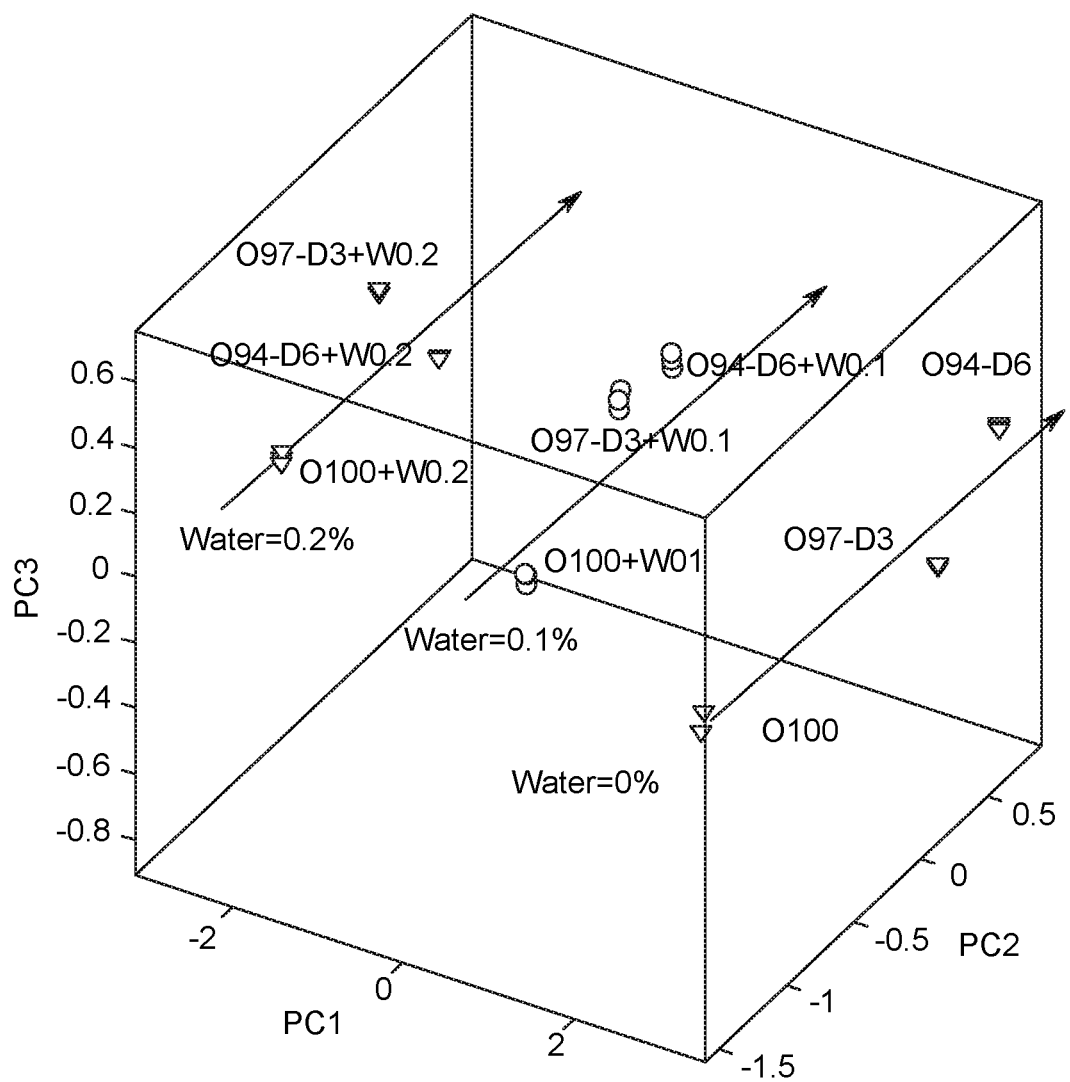
FIG. 15 is a plot of a resonant impedance data for detection of engine oil, water, and fuel with a highlighted water leak.
Figure 16:
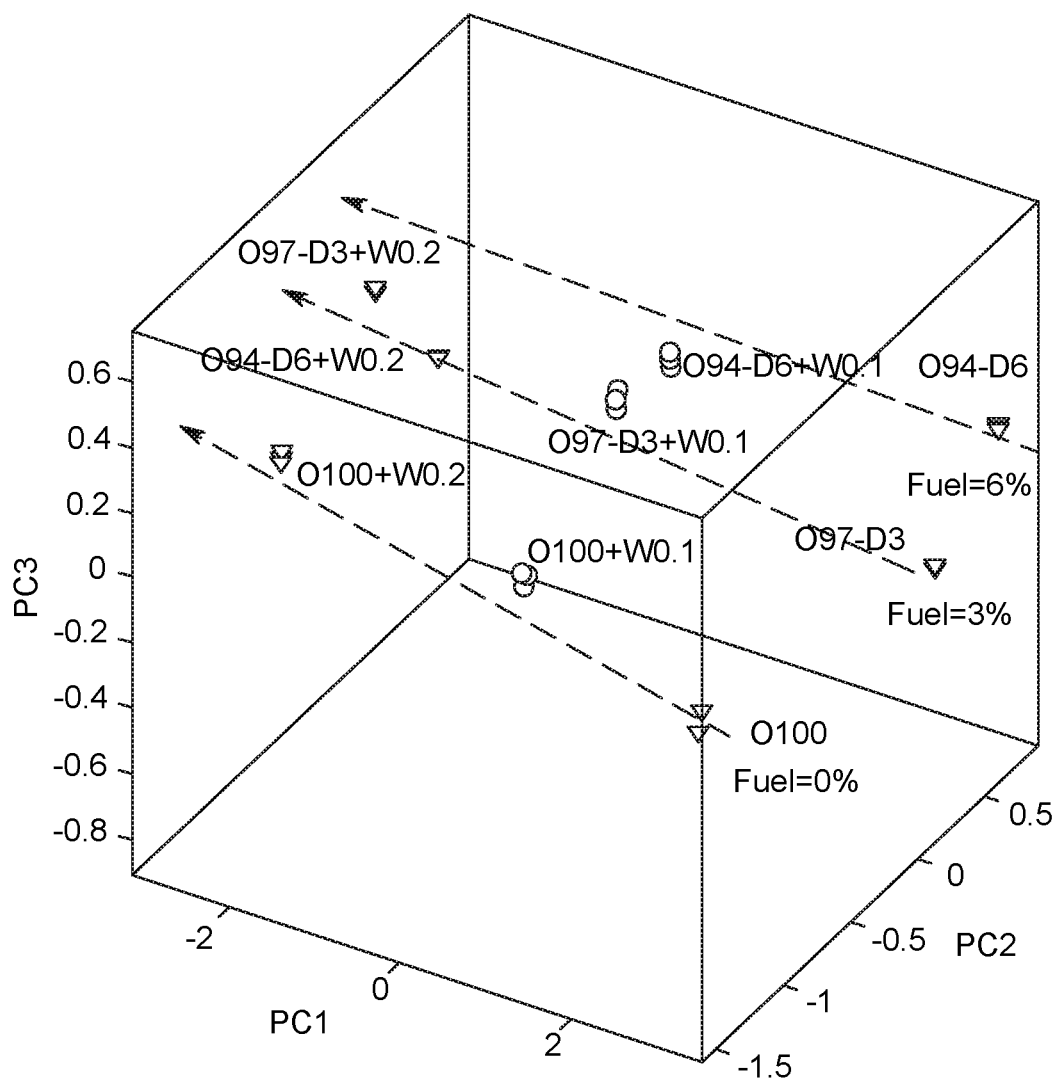
FIG. 16 is a plot of a resonant impedance data for detection of engine oil, water, and fuel with a highlighted fuel leak.

The resonance spectra from measured samples may be processed and the processed data served as inputs to the principal components analysis (PCA) tool. PCA may be a pattern recognition method that explains the variance of the data as the weighted sums of the original variables, known as principal components (PCs). A highlight of detection of water in mixtures of engine oil, water, and fuel may be illustrated in FIG. 15 that depicts a scores plot of a developed PCA model. A highlight of detection of fuel in mixtures of engine oil, water, and fuel may be illustrated in FIG. 16 that depicts a scores plot of a developed PCA model. In FIGS. 15 and 16, concentrations of water of 0.1% and 0.2% are labeled as W0.1 and W0.2, respectively. Concentrations of fuel of 3% and 6% are labeled as D3 and D6, respectively. The multivariable response of the resonant transducers originates from the measured whole resonance spectra of the transducer followed by the processing of these spectra using multivariate analysis tools. For quantitation of contamination of engine oil by water and fuel leaks with a single multivariable sensor, the resonant impedance spectra $(f)=Z_{re}(f)+jZ_{im}(f)$ of the resonant transducer may be measured. Several parameters from the measured (f) spectra may be calculated that included the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_z$ of $Z_{im}(f)$ as shown in FIG. 8.

By using multivariate analysis of calculated parameters of (f) spectra, classification of analyte may be performed. Suitable analysis techniques for multivariate analysis of spectral data from the multivariable sensors may include Principal Components Analysis (PCA), Independent Component Analysis (ICA), Linear Discriminant Analysis (LDA), and Flexible Discriminant Analysis (FDA). PCA may be used to discriminate between different vapors using the peptide-based sensing material. A loadings plot of the PCA model is illustrated in FIG. 17. This plot illustrates the contributions of individual components from the resonance spectrum. The plot shows that all components such as Fp, F1, F2, Fz, Zp, Z1, and Z2 had contributions to the sensor response.

Figure 18:
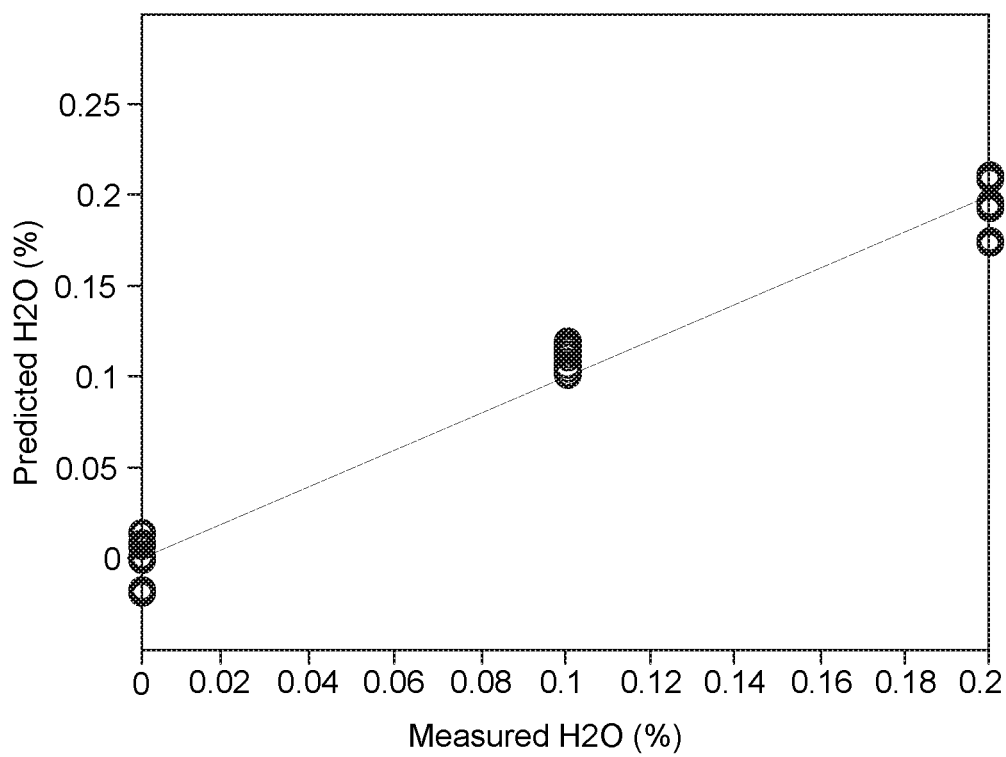
FIG. 18 is a correlation plot between the actual (measured) and predicted concentrations of water in water/fuel/oil mixtures using a single resonant sensor.
Figure 19:
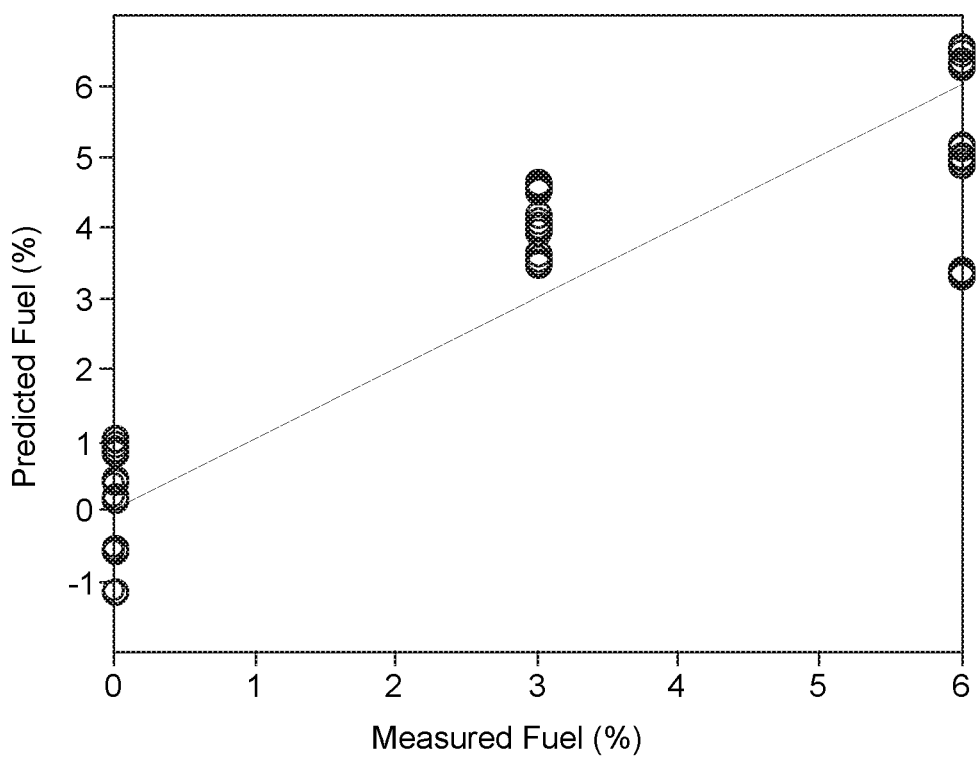
FIG. 19 is a correlation plot between the actual (measured) and predicted concentrations of fuel in water/fuel/oil mixtures using a single resonant sensor.

Quantitation of water and fuel in oil in their binary and ternary mixtures may be further performed with a single multivariable resonant sensor using PLS Toolbox (Eigenvector Research, Inc., Manson, Wash.) operated with Matlab (The Mathworks Inc., Natick, Mass.). FIG. 18 shows a correlation plot between actual (measured) and predicted concentrations of water in water/fuel/oil mixtures using a single resonant sensor. FIG. 19 shows a correlation plot between measured and predicted concentrations of fuel in water/fuel/oil mixtures using a single resonant sensor. Prediction errors of simultaneous quantitation of water and fuel in oil with the single sensor may be 0.02% of water and 1.3% of fuel.

Figure 20:
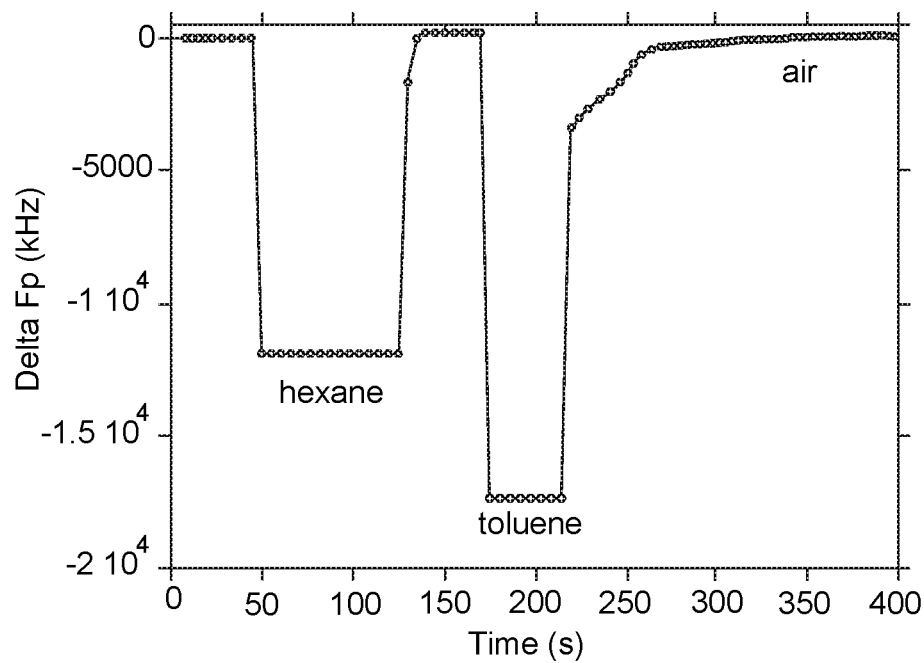
FIG. 20 is a plot of a spectral parameter showing resolution of a resonant sensor to distinguish between hexane and toluene.
Figure 21:
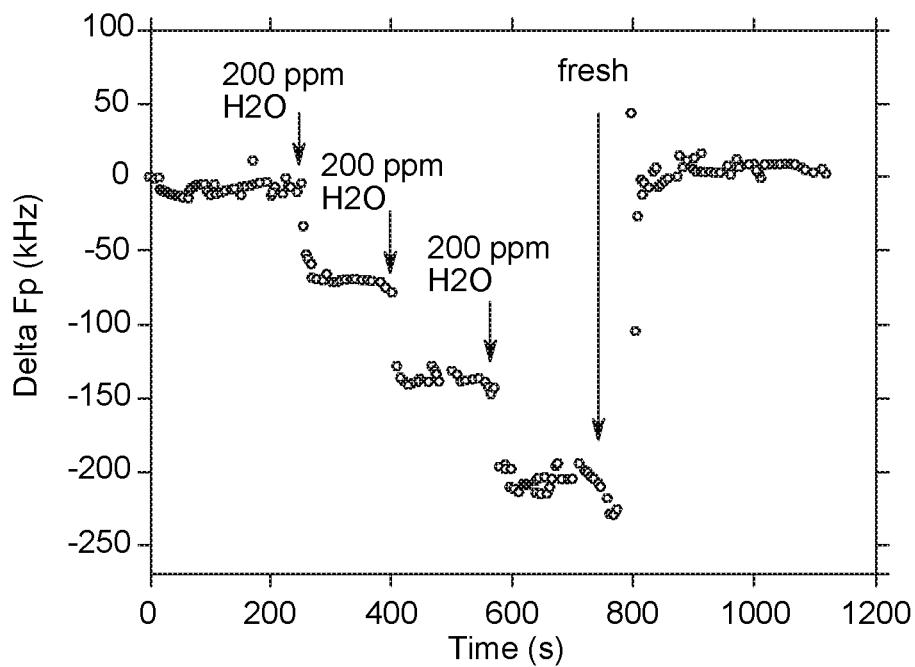
FIG. 21 is a plot of a spectral parameter showing resolution of water addition into dioxane.

In another example, sensor resolution may be determined in multi-part experiments. In a first experiment, hexane and toluene may be used as model chemicals to determine the ability of the sensor to resolve differences in the dielectric constant. Hexane has the dielectric constant of 1.88 while toluene has the dielectric constant of 2.38. A developed sensor may resolve these two liquids with the resolution of the dielectric constant of 0.0004-0.0012. Expected results are shown in FIG. 20. In the second experiment, 1,4-dioxane may be used as a model chemical for oil because the dielectric constant is similar to oil and the water miscibility is relatively high. The sensor may resolve water additions into dioxane down to 7-20 ppm. Expected results are shown in FIG. 21 illustrating that the developed sensor may be able to resolve water additions into dioxane (model system for oil) down to 7-20 ppm with water additions done in increments of 200 ppm.

Figure 22:
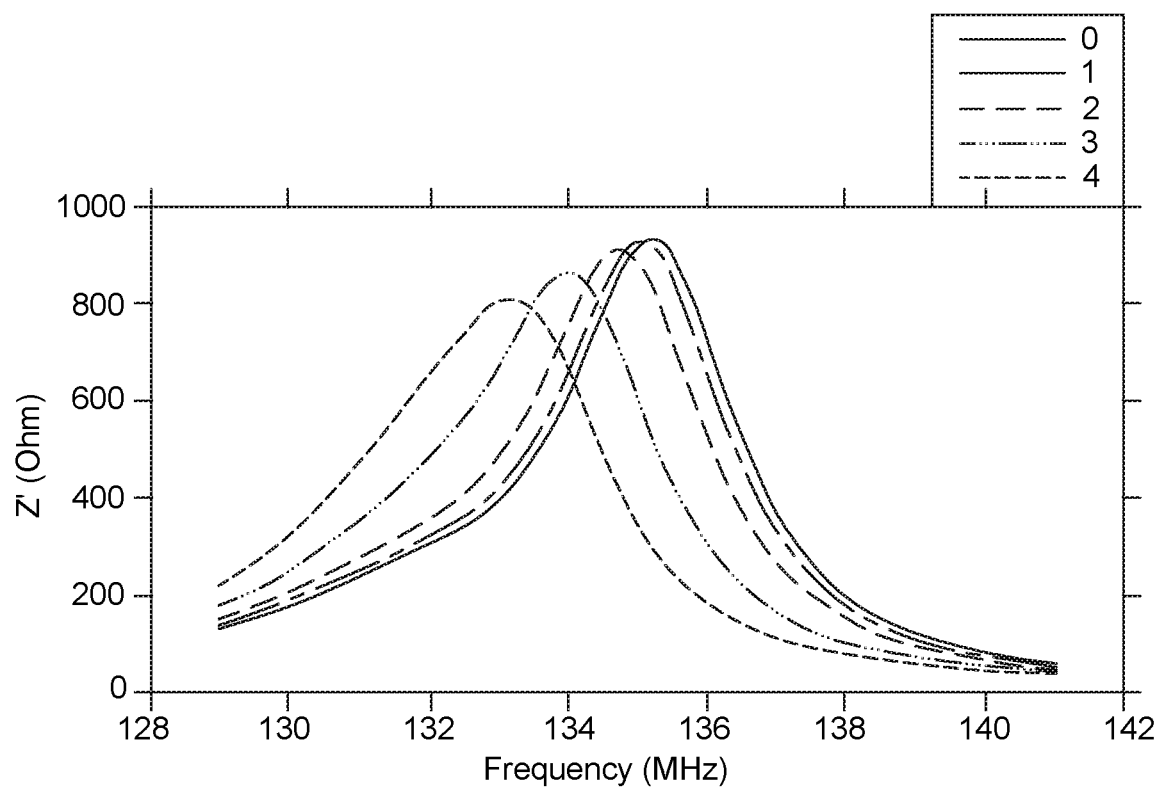
FIG. 22 is a plot of the real part of resonant impedance spectra after soot and water addition.
Figure 23:
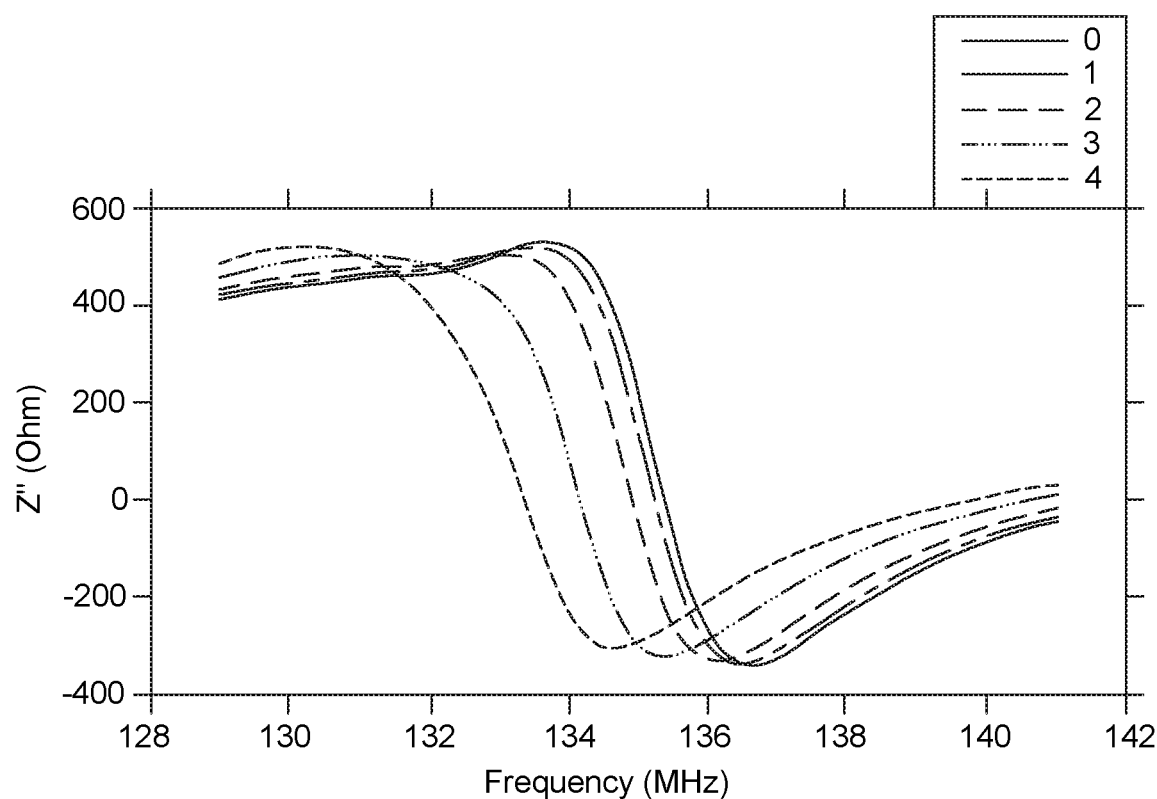
FIG. 23 is a plot of the imaginary part of resonant impedance spectra after soot and water addition.
Figure 24:
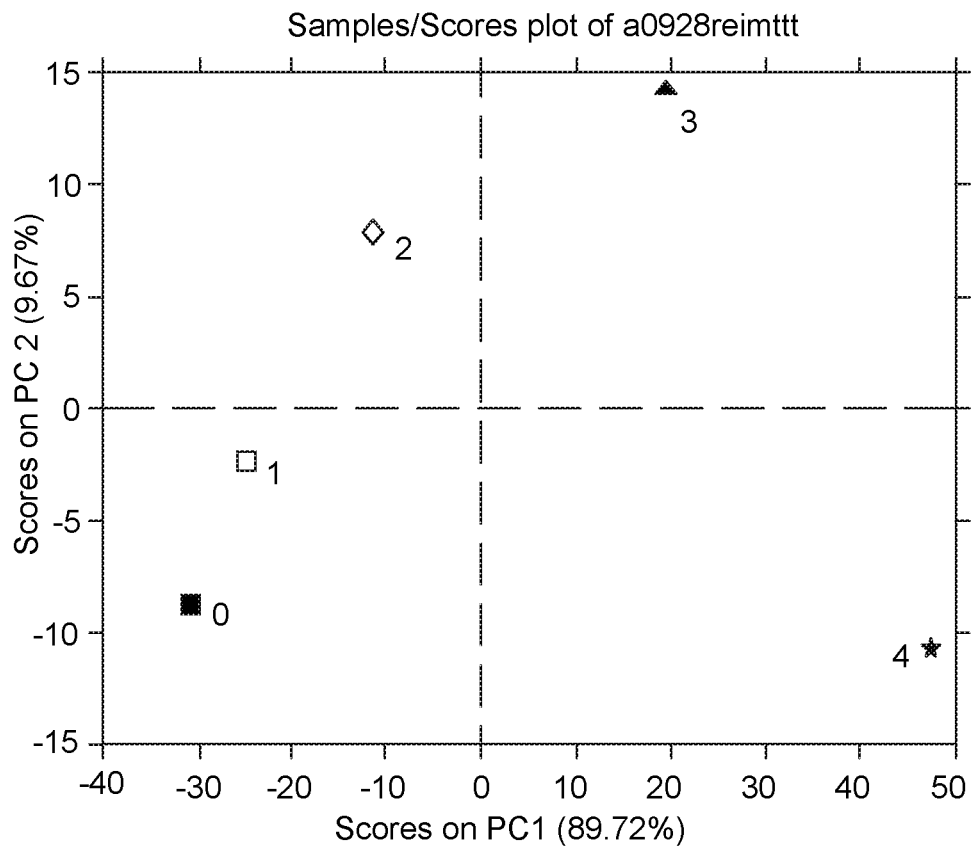
FIG. 24 depicts the PCA scores plot of PC1 vs. PC2 upon exposure of sensor to five solutions and performing resonance impedance measurements.

In another example, water and soot (carbon black) additions may be done to dioxane and measured with a sensor. Water additions may be done as 500 ppm, 1000 ppm, and 2500 ppm additions. Soot (carbon black) may be added as 100 ppm carbon black with 2500 ppm of water. Exemplary resonance spectra of a sensor are presented in FIGS. 22 and 23. Results of multivariate analysis are presented in FIG. 24. FIG. 22 shows the real part $Z_{re(f)}$ and FIG. 23 shows imaginary part $Z_{im(f)}$ of resonant impedance. Measured samples may be: (0) clean model oil (dioxane); (1) addition of 500 ppm of water; (2) addition of 1000 ppm of water, (3) addition of 2500 ppm of water; (4) addition of 2500 ppm of water and 100 ppm of soot (carbon black). FIG. 24 shows a scores plot of Principal component 1(PC1) vs. Principal component 2 (PC2) illustrating spectral relation between sensor responses to different types of contamination. Samples may be: (0) clean model oil (dioxane); (1) addition of 500 ppm of water; (2) addition of 1000 ppm of water; (3) addition of 2500 ppm of water; (4) addition of 2500 ppm of water and 100 ppm of soot (as carbon black).

Figure 25:
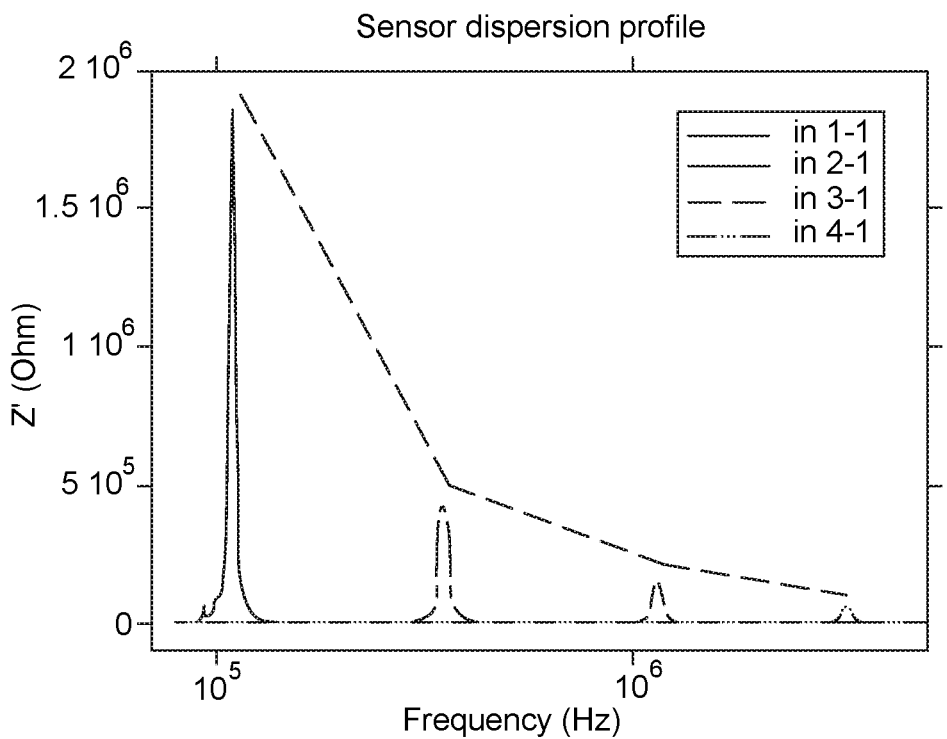
FIG. 25 displays a plot of four resonant spectral profiles from a single sensor for uncontaminated dioxane.
Figure 26:
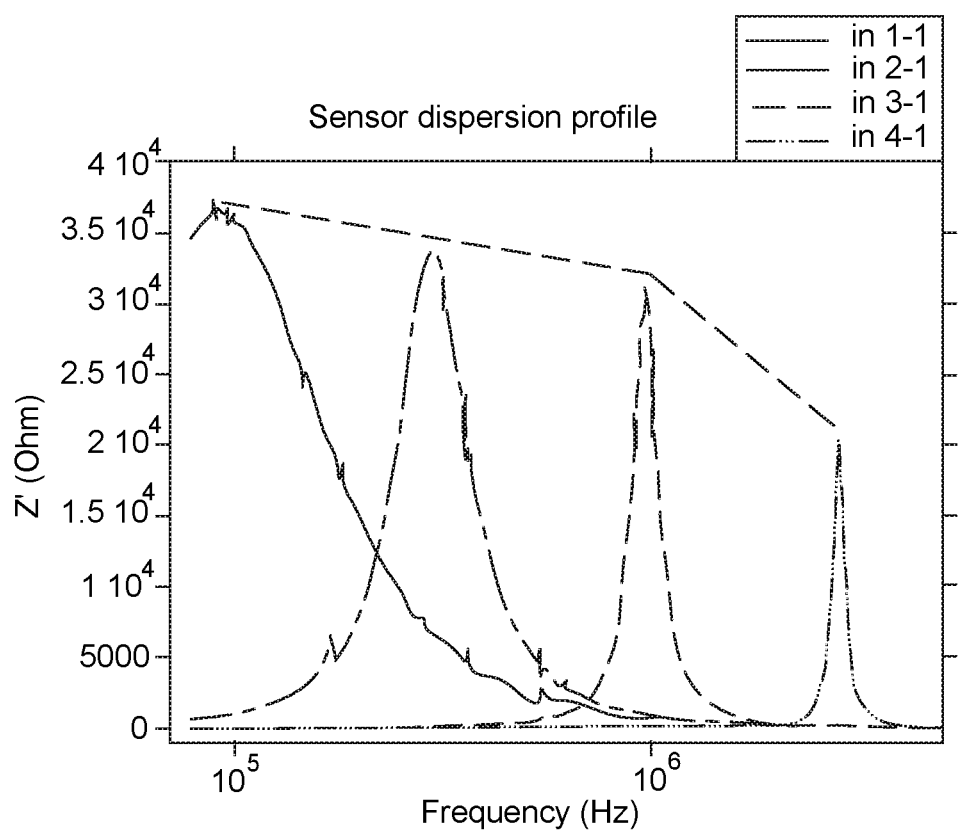
FIG. 26 displays a plot of resonant spectral profiles from a single sensor upon addition of water into the dioxane.

In another example, a multiresonant sensor system may be built with four resonant frequencies. The 1,4-dioxane can be used as a model chemical for oil, because its dielectric constant is somewhat similar to oil and it is miscible with water. Water additions may be done to dioxane and measured with a sensor. Four example resonance spectra of the sensor are presented in FIGS. 25 and 26. These values illustrate that the dispersion profile of the sensor in noncontaminated dioxane (as shown in FIG. 25) has changed its shape upon addition of water (as shown in FIG. 26). Also, the widths and the magnitudes of the resonance peaks have been modified by water addition.

Figure 27:
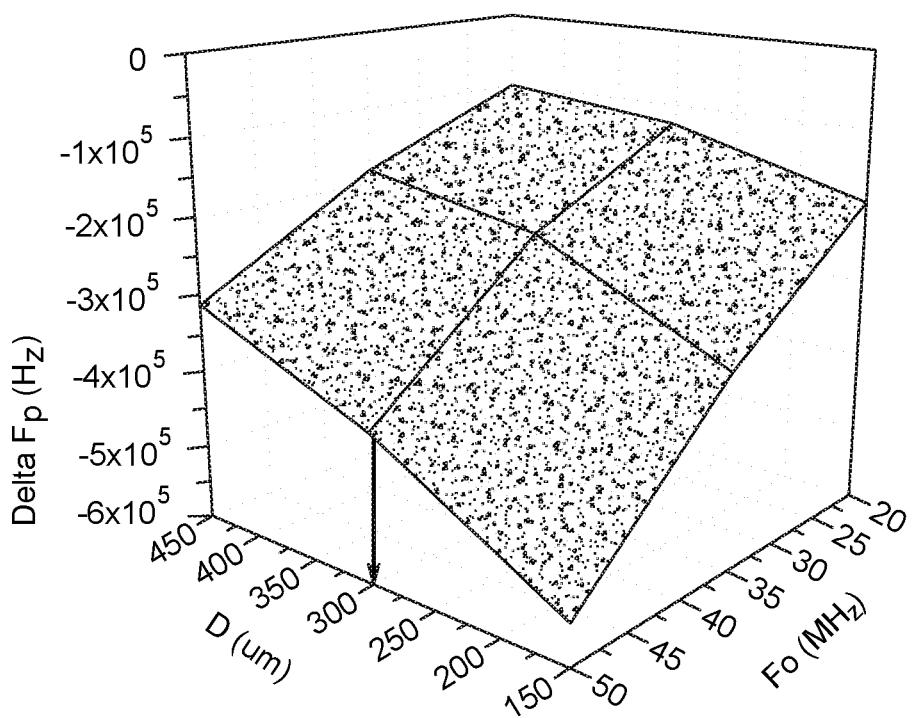
FIG. 27 is plot of effects of sensor design on sensitivity of Fp measurements.
Figure 28:
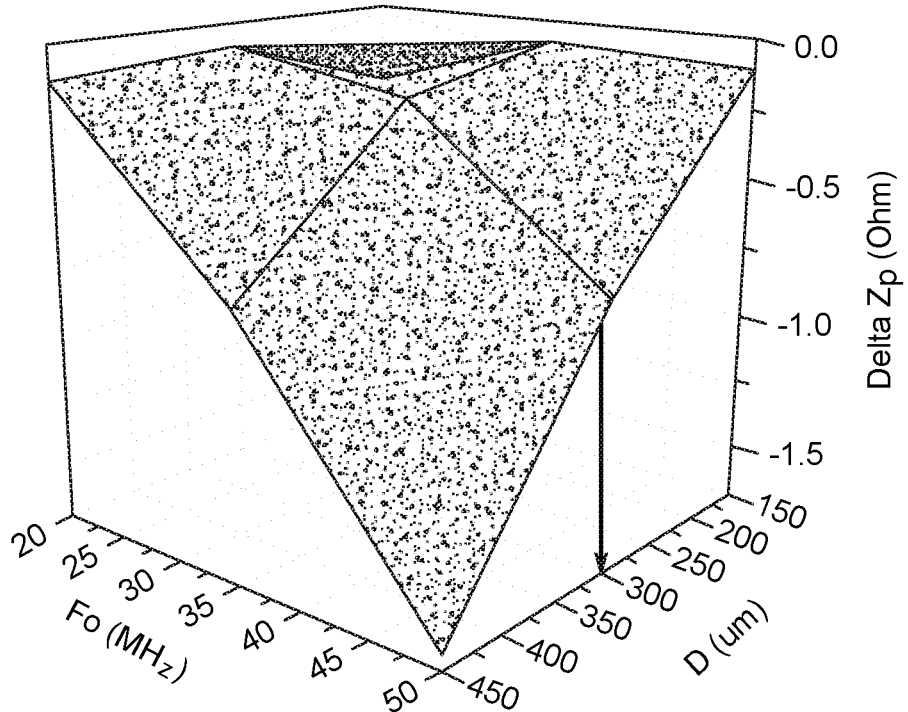
FIG. 28 displays effects of sensor design on sensitivity of Zp measurements.

In another example, sensor electrode geometries and resonant frequency may be optimized for the maximum Fp and Zp responses to water. A two-factor design of experiments may be done by varying interdigital electrode (IDE) spacing D and electrode width W, where D=W=150, 300, 450 micrometers (μm) and varying resonance frequency, Fp, as Fp=20, 35, 50 MHz (in air). Measurements may be performed by adding water to dioxane at 5000 ppm concentration. FIG. 27 shows effects of sensor design on sensitivity of Fp measurements. FIG. 28 shows effects of sensor design on sensitivity of Zp measurements. A 300 μm IDE spacing and 50 MHz operation frequency yielded strong Fp and Zp signals.

Figure 29:
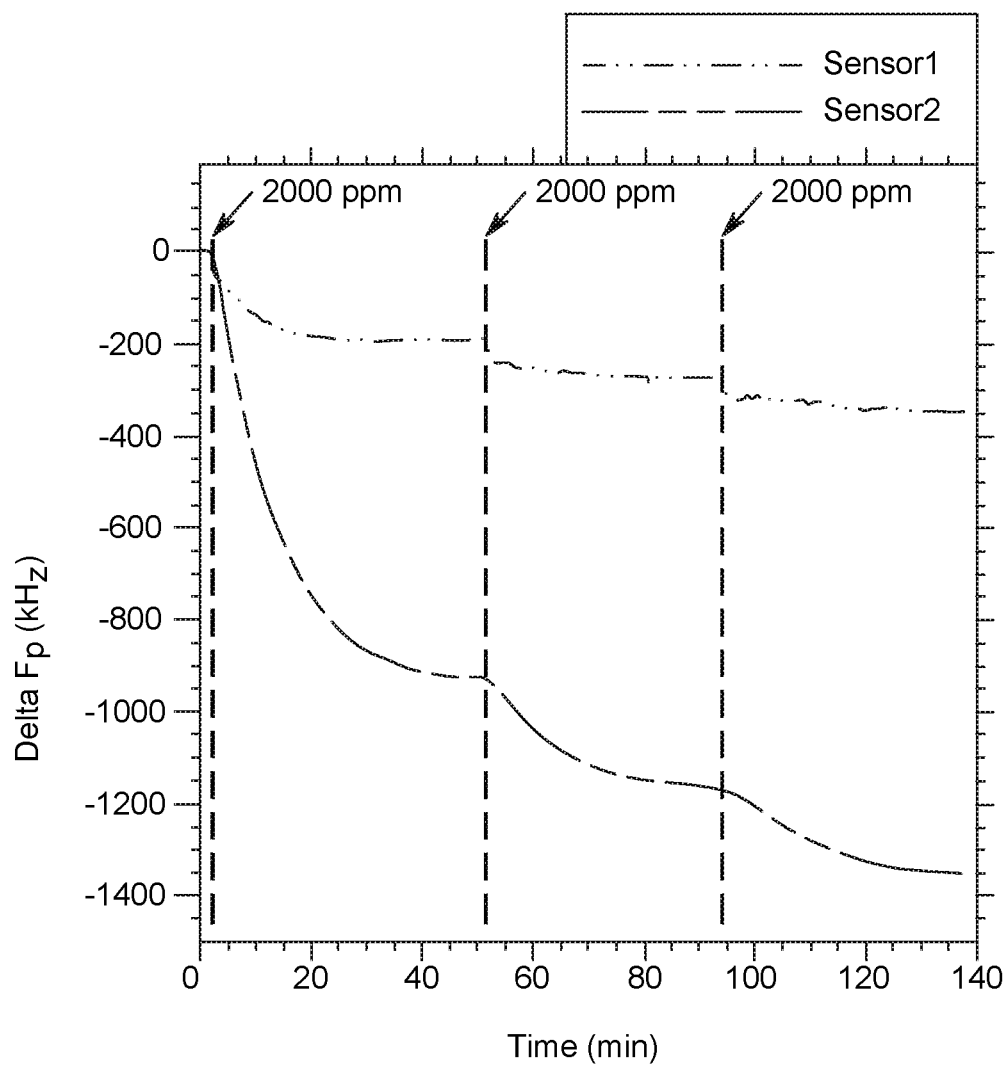
FIG. 29 is plot of results of measurements of water in oil with two multivariable resonant sensors.

In another example shown in FIG. 29, determination of water in oil may be performed by circulating oil in a test loop and adding water at 2000 ppm increments to generate water concentrations in oil of 2000 ppm, 4000 ppm, and 6000 ppm. Measurements may be performed using two resonant sensors. Sensor 1 had area of 2 $cm^2$ with the electrode width/spacing of 0.4 mm/0.4 mm and resonating at 80 MHz in air. Sensor 2 may be one of geometries from the design of experiments and had area of 4 $cm^2$ with the electrode width/spacing of 0.15 mm/0.15 mm and resonating at ~50 MHz in air. The limit of detection of water in oil may be determined at the signal-to-noise level of three to be 3-12 ppm (Sensor 1) and 0.6-2.6 ppm (Sensor 2) based on the measured sensor noise levels and signal levels at 2000 ppm of added water.

Figure 30:
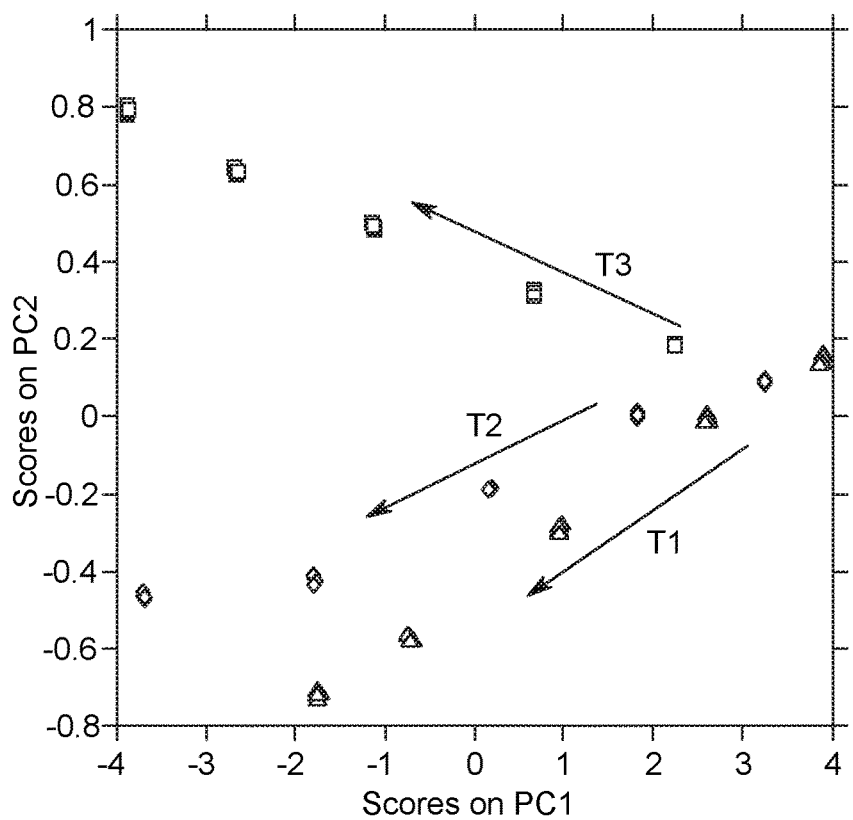
FIG. 30 is a scores plot of a developed PCA model of responses of the resonant sensor to additions of water at different temperatures, showing different response directions.
Figure 31:
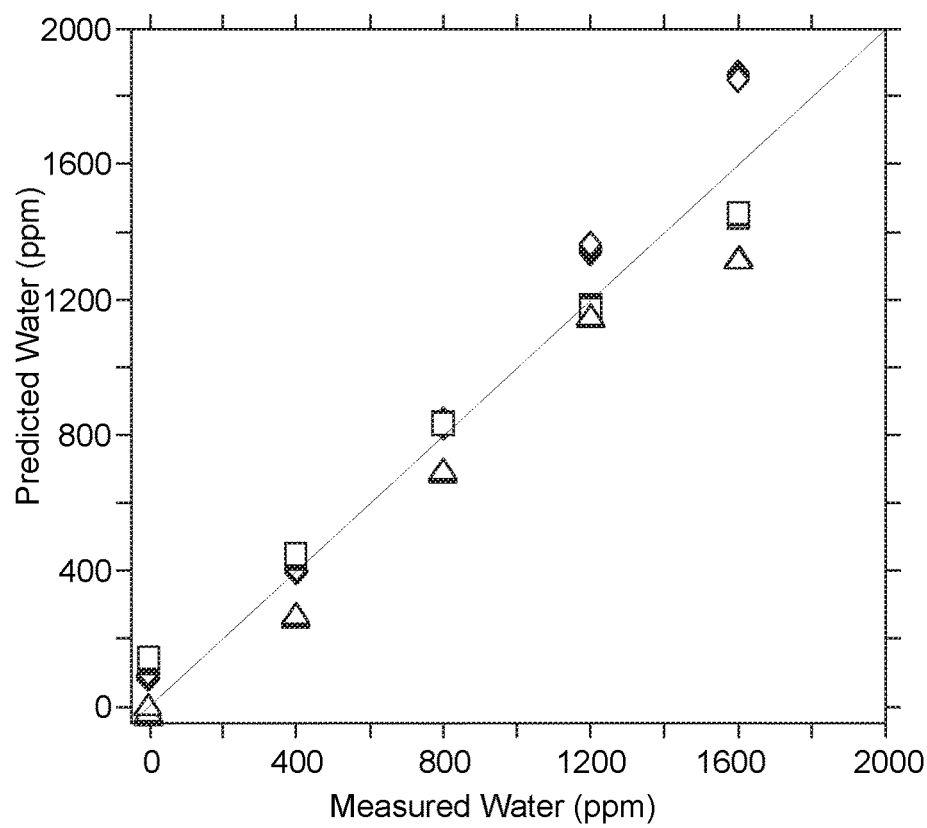
FIG. 31 is plot of results of multivariate linear regression model using partial least squares technique to quantify water concentrations in oil using responses of the single sensor.
Figure 32:
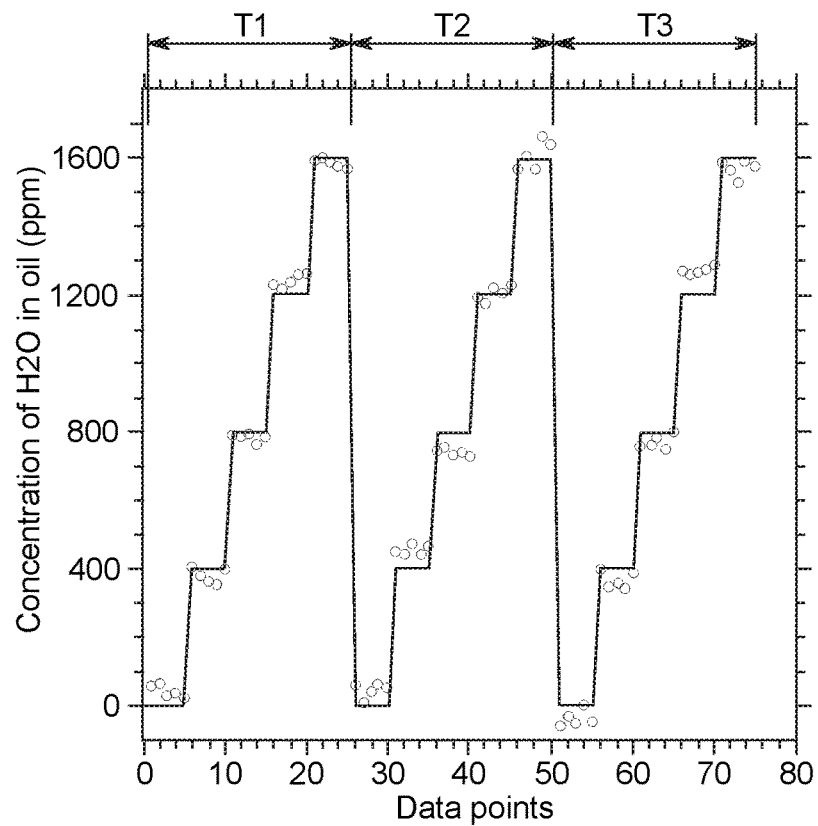
FIG. 32 is a plot of the actual (measured) concentrations of water in oil over time at three temperatures (solid line) and predicted concentrations (open circles).

In another example, determination of water in oil at different oil temperatures may be performed by circulating oil in a test loop and adding water at 400 ppm increments to generate water concentrations in oil of 400 ppm, 800 ppm, 1200 ppm, and 1600 ppm. The nominal temperatures of oil may be T1=80 degrees Celsius, T2=100 degrees Celsius, and T3=120 degrees Celsius as produced by a thermal bath. FIG. 30 depicts a scores plot of a developed PCA model illustrating that responses of the resonant sensor to additions of water at different temperatures may be in different directions. Each individual arrow in FIG. 30 points in the direction of increasing water concentrations at oil temperatures T1, T2, and T3. FIG. 31 may depict results of multivariate linear regression model using partial least squares (PLS) technique to quantify water concentrations in oil using responses of the single sensor. The PLS technique may determine correlations between the independent variables and the sensor response by finding the direction in the multidimensional space of the sensor response that explains the maximum variance for the independent variables. FIG. 32 shows that such multivariate linear regression may be able to predict water concentrations independent of oil temperature.

Figure 33:
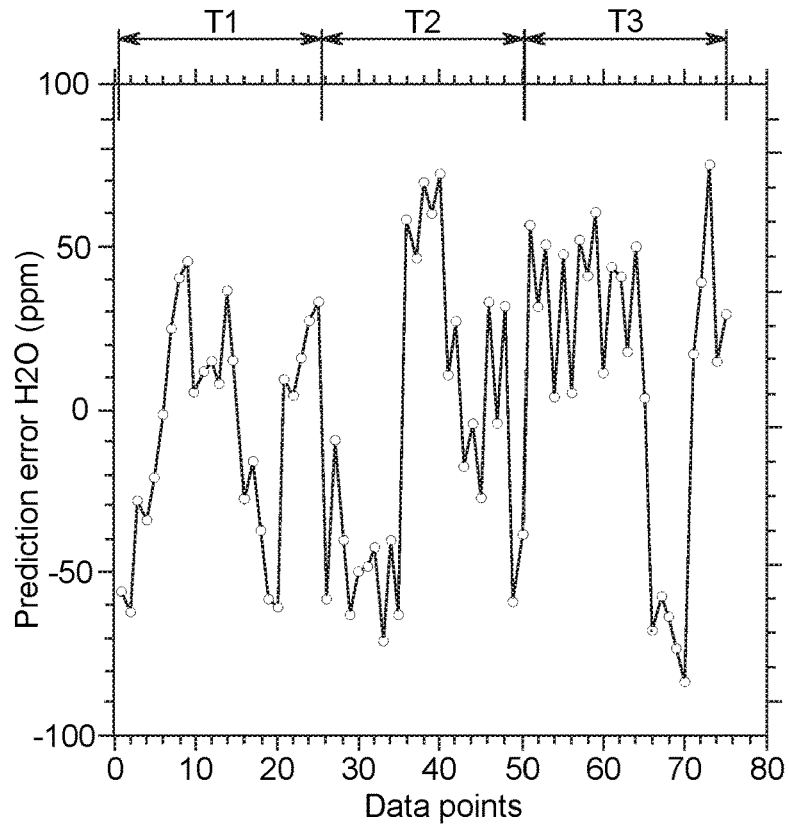
FIG. 33 is a plot of prediction error between actual and predicted concentrations of water in oil over time at three temperatures.
Figure 34:
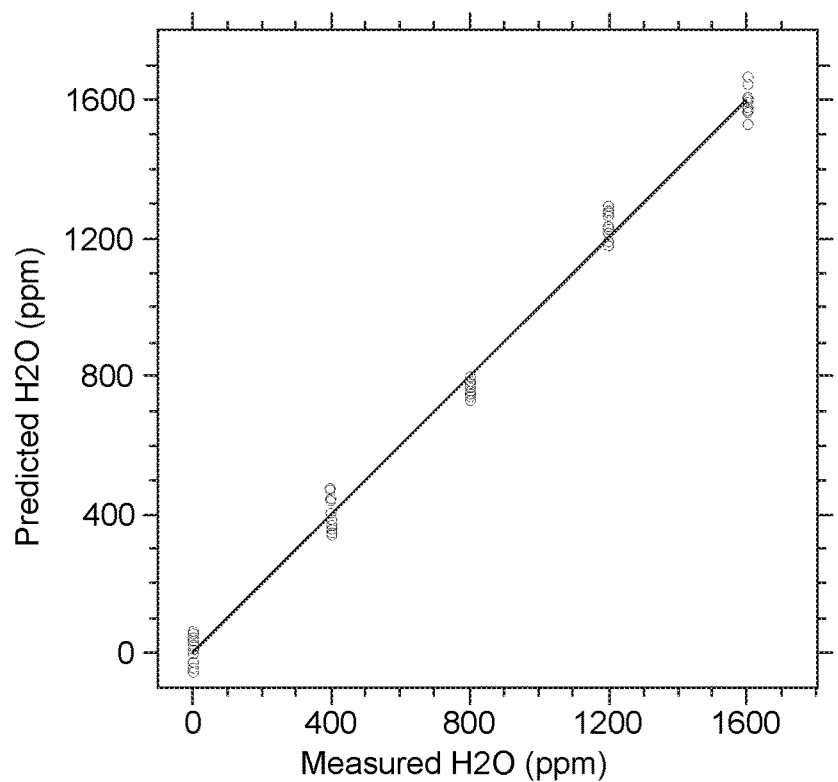
FIG. 34 is a plot of correlation between actual (measured) and predicted concentrations of water in oil at three temperatures.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be performed using a multivariate non-linear (quadratic) regression. FIG. 32 depicts the actual (measured) concentrations of water in oil at three temperatures (solid line) and predicted concentrations (open circles). FIG. 33 depicts prediction error between actual and predicted concentrations of water in oil at three temperatures. FIG. 34 depicts a correlation plot between actual (measured) and predicted concentrations of water in oil at three temperatures.

Figure 35:
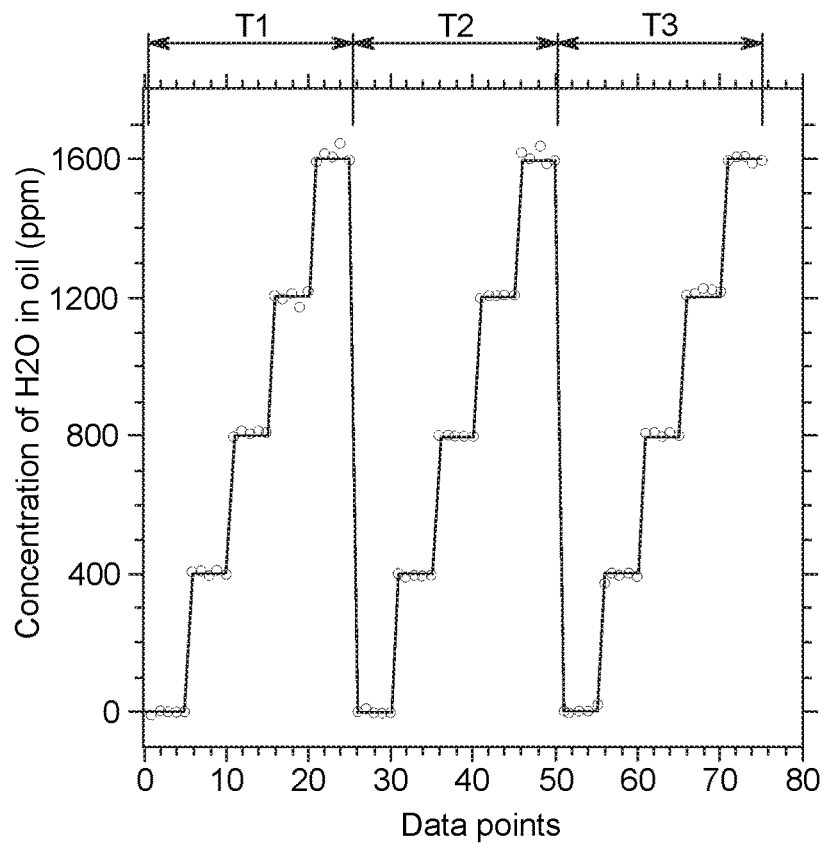
FIG. 35 is a plot of the actual (measured) concentrations of water in oil over time at three temperatures (solid line) and predicted concentrations (open circles) using responses of a multivariable resonant sensor and oil temperature sensor.
Figure 36:
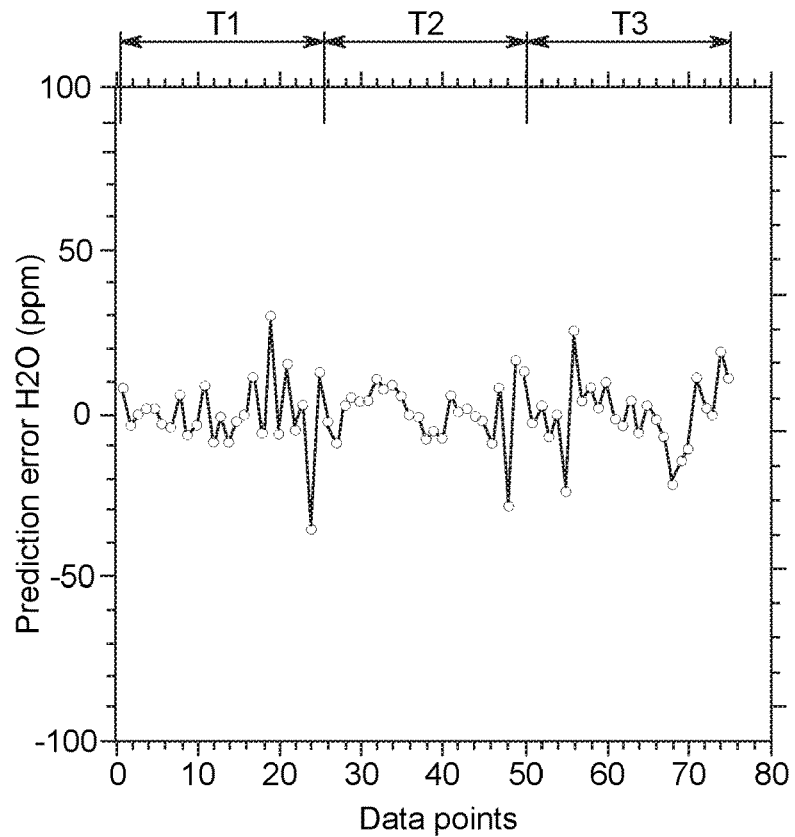
FIG. 36 is a plot of prediction error between actual and predicted concentrations of water in oil over time at three temperatures using responses of a multivariable resonant sensor and oil temperature sensor.
Figure 37:
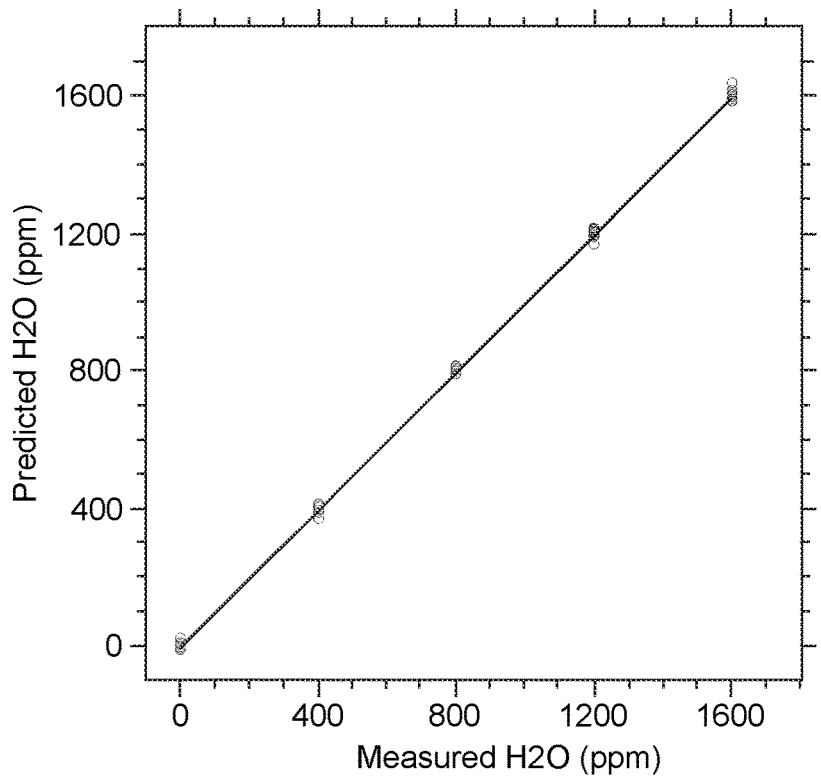
FIG. 37 is a plot of correlation between actual (measured) and predicted concentrations of water in oil at three temperatures using responses of a multivariable resonant sensor and oil temperature sensor.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be further performed using a multivariate non-linear (quadratic) regression with an additional input from a temperature sensor positioned in measured oil. FIG. 35 depicts the actual (measured) concentrations of water in oil at three temperatures (solid line) and predicted concentrations (open circles). FIG. 36 depicts prediction error between actual and predicted concentrations of water in oil at three temperatures. FIG. 37 depicts a correlation plot between actual (measured) and predicted concentrations of water in oil at three temperatures.

Figure 38:
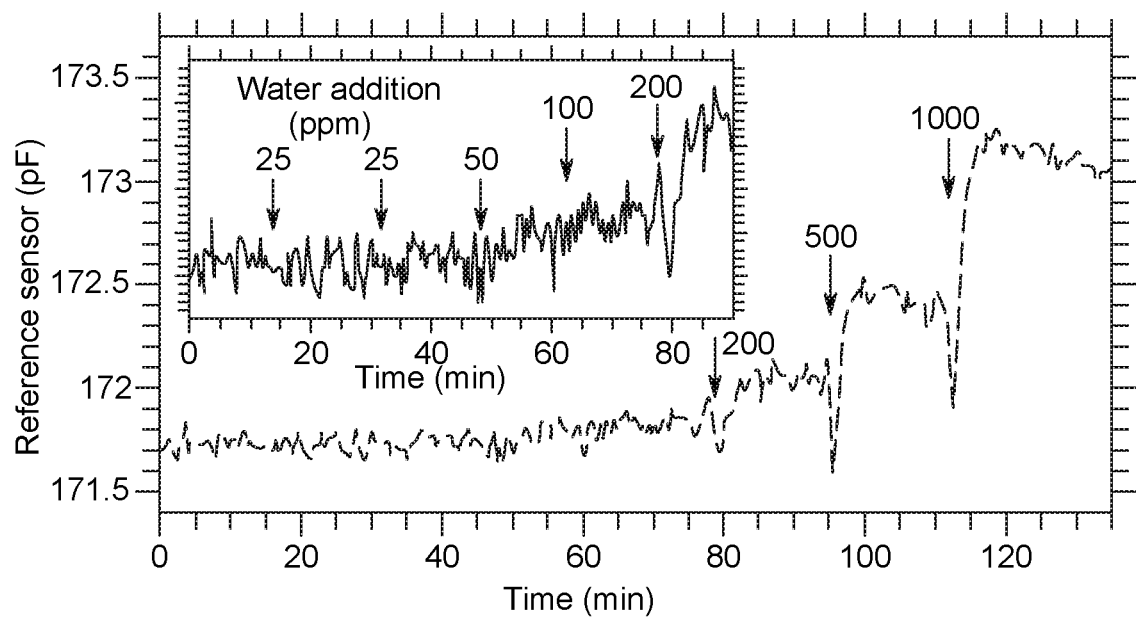
FIG. 38 is a response of a reference capacitance sensor to water leaks into engine oil at levels of 25, 25, 50, 100, 200, 500, and 1000 ppm each. Inset shows response to initial water leaks.
Figure 39:
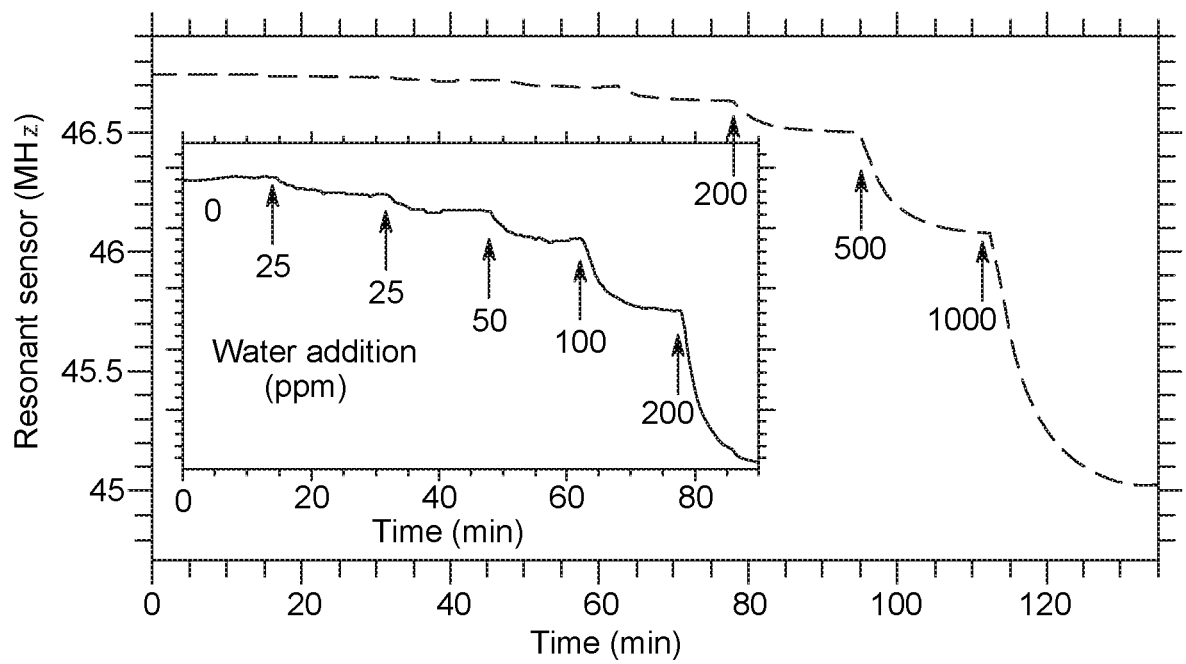
FIG. 39 is a response of a developed resonant sensor to water leaks into engine oil at levels of 25, 25, 50, 100, 200, 500, and 1000 ppm each. Inset shows response to initial water leaks.

The performance of this developed resonant sensor may compare with the performance of a standard non-resonant capacitance sensor that served as a reference capacitance sensor. This reference capacitance sensor has two co-axis pipes, and it is possible to measure capacitance of the fluid being tested by applying a sinusoidal signal to the inner pipe. The comparison may be performed by having both sensors in the same circulating-oil loop where water leaks may be introduced and presented to both sensors. Water leaks levels may be 25, 25, 50, 100, 200, 500, and 1000 ppm. FIG. 38 depicts the response of a reference capacitance sensor to water leaks into engine oil at levels of 25, 25, 50, 100, 200, 500, and 1000 ppm each. This figure illustrates that the reference capacitance sensor did not show an appreciable signal change from its noise until water leaks of 25, 25, 50, 100, and 200 ppm are all introduced. In contrast, FIG. 39 shows the response of a resonant sensor to water leaks into engine oil according to an embodiment, where this sensor may detect the smallest water leak at 25 ppm as well as all other water leaks presented to both sensors.

Figure 40:
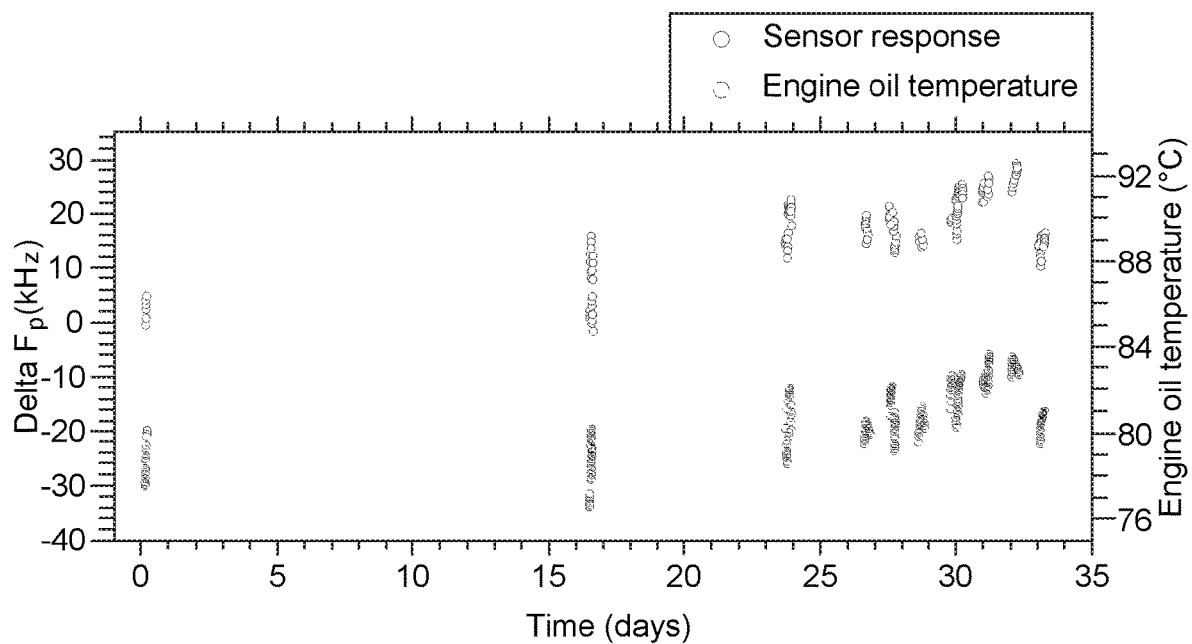
FIG. 40 shows operation of the developed resonant sensor in a single cylinder locomotive engine.
Figure 41:
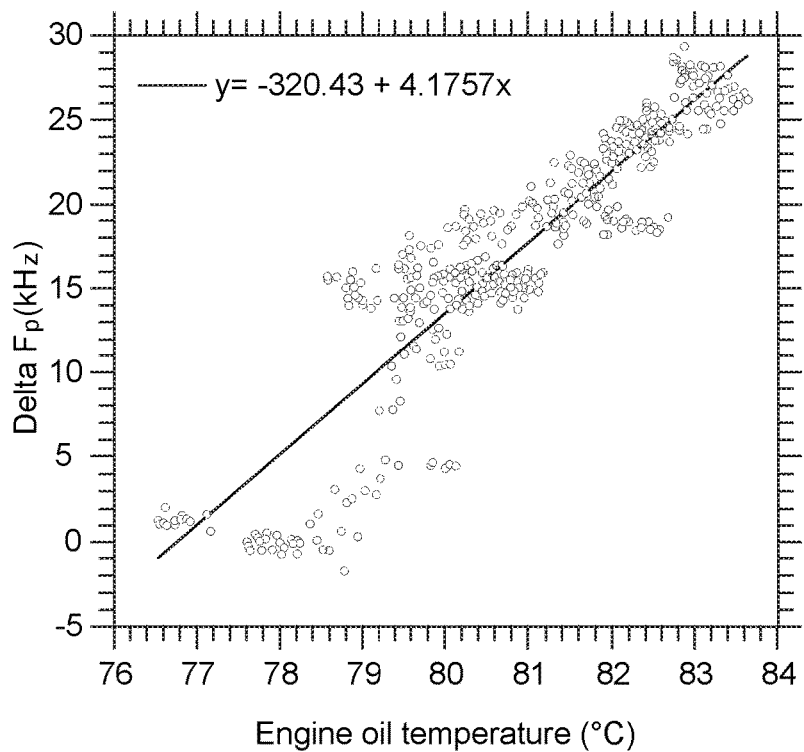
FIG. 41 shows correlation between response of the developed resonant sensor in a single cylinder locomotive engine and the temperature of oil.

The resonant sensor may be tested in a single cylinder locomotive engine test bed for about 34 days. FIG. 40 is a graph depicting results of temperature of oil and sensor response after operating the developed resonant sensor in a single cylinder locomotive engine test bed for a period of 34 days. FIG. 41 illustrates a correlation between response of the developed resonant sensor in a single cylinder locomotive engine for about 34 days and the temperature of oil.

In another example, sources of leaks in an engine may be determined by identifying dynamic signatures of the leaks, relating the identified signature with a known leak signature from a specific engine component, and determining the location of the leak based on the signature or relationship. Such approach may provide the ability for proactive maintenance, replacing reactive maintenance, and may increase the time-in-use for assets having lubrication systems or internal combustion engines.

Figure 42:
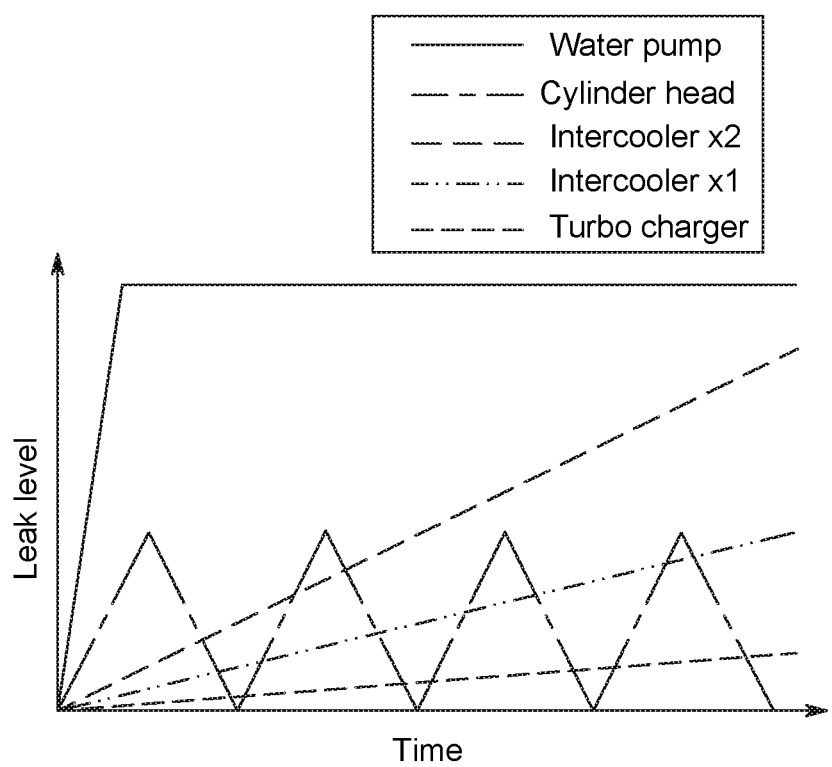
FIG. 42 is a schematic of dynamic signatures of leaks in typical components in an internal combustion engine.

Non-limiting examples of such assets with internal combustion engines include various vehicle types, each having its own set of operating parameters. Embodiments disclosed herein may provide a prognostics sensor tool for early determination of leaking components via dynamic leak signatures. These sensors may be applied in multiple locations in the engine to pinpoint the origin of leak. FIG. 42 depicts a schematic of dynamic signatures of leaks of a turbo charger (1-2 turbo chargers per engine), an intercooler (2 intercoolers per engine), a water pump (1 water pump per engine), and a cylinder head (likely multiple cylinder heads per engine).

Figure 43:
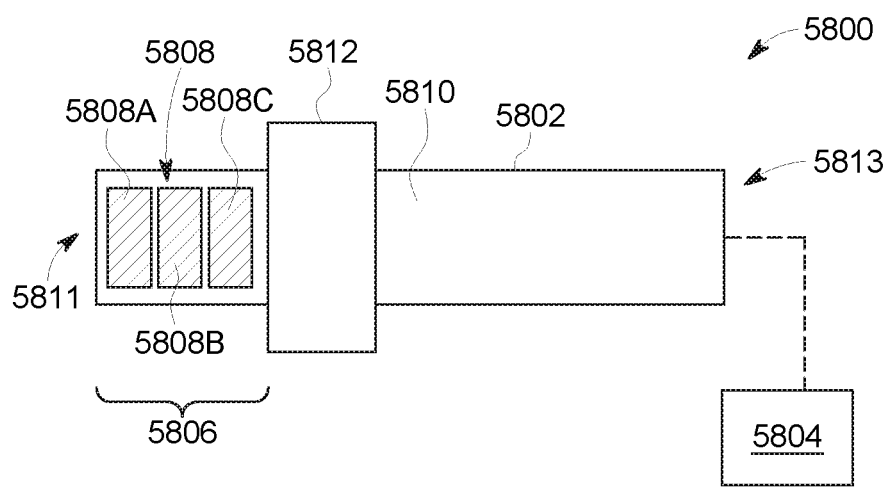
FIG. 43 is a schematic diagram of a sensing system that includes a sensor and a sensor reader.

FIG. 43 is a schematic diagram of a sensing system 5800 that includes a sensor 5802 and a sensor reader 5804. The sensor reader 5804 may be at least similar to the sensor reader 2659B shown in FIGS. 11 and 12. The sensor 5802 includes a sensing region 5806 that includes multiple electrodes 5808. The sensing region 5806 is configured to be placed in operational contact with an industrial fluid of interest, such as an oil, a fuel, or a solvent. The electrodes 5808 may contact the industrial fluid directly or indirectly due to a dielectric sensing layer that may cover at least some of the electrodes 5808. The sensing layer is applied to improve detection of water or other polar compounds in an industrial fluid. The sensing layer may be an inorganic sensing layer, unlike some conventional sensors that use polymeric sensing layers. Polymeric sensing layers in conventional resonant sensors operate by swelling and changing the resonant frequency of the sensor. In the sensor 5802, water uptake by the sensing film does not produce swelling and does not change film thickness. Rather, water uptake produces a change in the dielectric property and the capacitance of the sensing film at multiple frequencies. Unlike conventional resonant sensors, the sensor 5802 produces dielectric property changes of the sensing film at multiple frequencies (produced using tuning components illustrated in FIGS. 4 and 5) that allows more accurate determinations of the contaminants, such as water or other polar compounds. Such improved accuracy is provided by measurements of spectral dispersion of the sensing film before and after fluid contamination. Non-limiting examples of water sorbing or sensing layers include porous silicon porous ceramic, anodized aluminum oxide, and others. The sensing region 5806 has an electrode geometry that matches the measurement needs of the sensing region 5806.

The sensor 5802 in an embodiment includes a probe body 5810 that has a shoulder 5812 extending outward from the probe body 5810 such that the shoulder 5812 has a greater radial width or diameter than the probe body 5810. The shoulder 5812 is disposed along an intermediate segment of the probe body 5810. The sensing region 5806 extends from the shoulder 5812 to a distal end 5811 of the probe body 5810. A proximal end 5813 of the probe body 5810 is operably coupled to the sensor reader 5804. The electrodes 5808 are disposed on the sensing region 5806 at different distances relative to the shoulder 5812 such that the electrodes 5808 extend different depths into the industrial fluid. In an embodiment, at least two of the electrodes 5808 operate at one or more high frequencies and at least one of the electrodes 5808 (that is different than the electrodes 5808 that operate at high frequencies) operates at one or more low frequencies.

For example, the sensor 5802 in the illustrated embodiment includes multiple sensing sub-regions that each includes one or more electrodes 5808 disposed therein. The sub-regions with electrodes each contain electrode structures where these structures are two-electrode structures or four-electrode structures. The sensing sub-regions include a distal sensing sub-region 5808A, an intermediate sensing sub-region 5808B, and a proximal sensing sub-region 5808C. The electrodes 5808 in the intermediate sub-region 5808B are located between the distal sub-region 5808A and the proximal sub-region 5808C. The electrodes 5808 in the different sub-regions 5808A-C may operate at different frequencies and/or frequency ranges relative to one another. Some of the electrodes 5808 in the different sub-regions 5808A-C may be used for contaminant (such as water) concentration detection, while other electrodes 5808 in the different sub-regions 5808A-C may be used for fluid aging detection. As an alternative to water, some examples of other contaminants that may be detected by the sensing system 5800 include fuel, dust, and other external contaminants.

The electrodes 5808 in the different sub-regions 5808A-C may have different electrode spacings between adjacent electrodes 5808.

The distal sensing sub-region 5808A in an embodiment is covered by the sensing layer. The distal sensing sub-region 5808A may be configured to measure low concentration water or other contaminant leaks in oil. Each electrode 5808 in the distal sensing sub-region 5808A may be an interdigitated electrode that has an area in the range from 0.1 mm$^2$ to 100 mm$^2$. The electrode spacing for the electrodes 5808 in the sub-region 5808A may be relatively small, such as in the range from 0.1 μm to 10 μm. For example, the electrodes 5808 may have an area of 2 cm×2 cm with an electrode spacing of 0.15 mm. The electrodes 5808 may resonate at around 50 MHz in air. The electrodes 5808 in the distal sub-region 5808A may be operated at relatively high frequencies and/or frequency ranges compared to the electrodes 5808 in the intermediate and/or proximal sub-regions 5808B, 5808C.

The electrodes 5808 in the intermediate sensing sub-region 5808B are located more proximate to the sensor reader 5804 than the distal sensing sub-region 5808A. The intermediate sensing sub-region 5808B is provided for preferential measurements of leaks of nonpolar external contaminants and fluid aging detection. These electrodes 5808 in an embodiment are not coated with a sensing layer. The electrodes 5808 in the intermediate sub-region 5808B may have relatively small spacing in the range from 0.1 μm to 10 μm. The electrodes 5808 of the intermediate sub-region 5808B may be operated at relatively high frequencies and/or frequency ranges compared to the electrodes 5808 in the proximal sub-region 5808C.

The electrodes 5808 in the proximal sensing sub-region 5808C are disposed more proximate to the sensor reader 5804 than the sensing sub-regions 5808A and 5808B. The electrodes 5808 in the sub-region 5808C are provided for preferential measurements of fluid aging detection. These electrodes are not coated with a sensing layer and can have relatively large spacing in the range from 1 μm to 5000 μm. The electrodes 5808 of the proximal sub-region 5808B may be operated at relatively lower frequencies and/or frequency ranges compared to the electrodes 5808 in the distal and/or intermediate sub-regions 5808A, 5808B. In other embodiments, the sensing region 5806 may include different numbers and/or arrangements of electrodes and/or sensing sub-regions.

With additional reference to FIGS. 4 and 5, the sensor 5802 includes at least one inductor-capacitor-resistor (LCR) resonant circuit having one or more tuning elements 1942. The one or more resonant LCR circuits are configured to generate an electrical stimulus having a spectral frequency range. The electrical stimulus is applied to the industrial fluid at the sensing region 5806 via the electrodes 5808. The electrical stimulus may include multiple electric fields and/or multiple frequencies.

The sensor 5802 is operably coupled to the sensor reader 5804, such as via a mechanical fixed connection, a wired connection, or a wireless electrical connection. For example, the sensor 5802 may include a communication unit (e.g., a transceiver or discrete transmitter and receiver) that wirelessly transmits electrical signals to the sensor reader 5804. The sensor reader 5804 includes one or more processors. The one or more processors may be one or more controllers (e.g., microcontrollers) or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

The one or more processors are configured to receive an electrical signal from the sensor 5802 that is representative of a resonant spectral response (or resonant impedance spectra) of the sensing region in operational contact with the industrial fluid in response to the electrical stimulus being applied to the industrial fluid.

The one or more processors are configured to analyze the resonant spectral response and determine properties of the fluid. For example, in one embodiment, the one or more processors may be configured to determine both a water concentration in the industrial fluid and an aging level of the industrial fluid based on the analyzed resonant spectral response. In another embodiment, described herein with reference to FIG. 64, the one or more processors may be configured to determine both a water concentration in the industrial fluid and at least one of an acid concentration or a base concentration in the industrial fluid based on the resonant spectral response. The resonant spectral response is indicative of a dielectric dispersion profile of the industrial fluid over the spectra frequency range of the electrical stimulus. The one or more processors may be configured to analyze the resonant spectral response by extracting resonance parameters from the resonant spectral response. The resonance parameters are described with reference to FIGS. 8 and 14.

The concentration of water or other external contaminants in the industrial fluid and the aging level of the fluid may be determined by comparing the extracted resonance parameters to known resonance parameters associated with various water concentrations of the industrial fluid and various aging levels of the industrial fluid. The comparison may include classifying the extracted resonance parameters using an earlier built classification model (as described in steps 2870 and 2872 of FIG. 14) and quantitating the extracted resonance parameters using an earlier built quantitation model (as described in steps 2880 and 2882 of FIG. 14).

In an embodiment, the sensor 5802 includes multiple LCR resonant circuits. Each resonant LCR circuit has a different resonant frequency. The electrical stimulus applied to the industrial fluid is generated over a spectral frequency range that includes or incorporates the resonant frequencies of the resonant LCR circuits such that the impedance spectral response is measured over the resonant frequencies. Optionally, the sensor 5802 may include a multiplexer 1944 (shown in FIG. 4) that is configured to individually control the resonant LCR circuits to tune the electrical stimulus that is applied to the industrial fluid. The multiple resonant frequencies allow the sensing system 5800 to detect multiple variables or properties of the industrial fluid, such as the concentration of water and the age of the fluid. For example, the sensing system 5800 may include four resonant frequencies.

Figure 2:
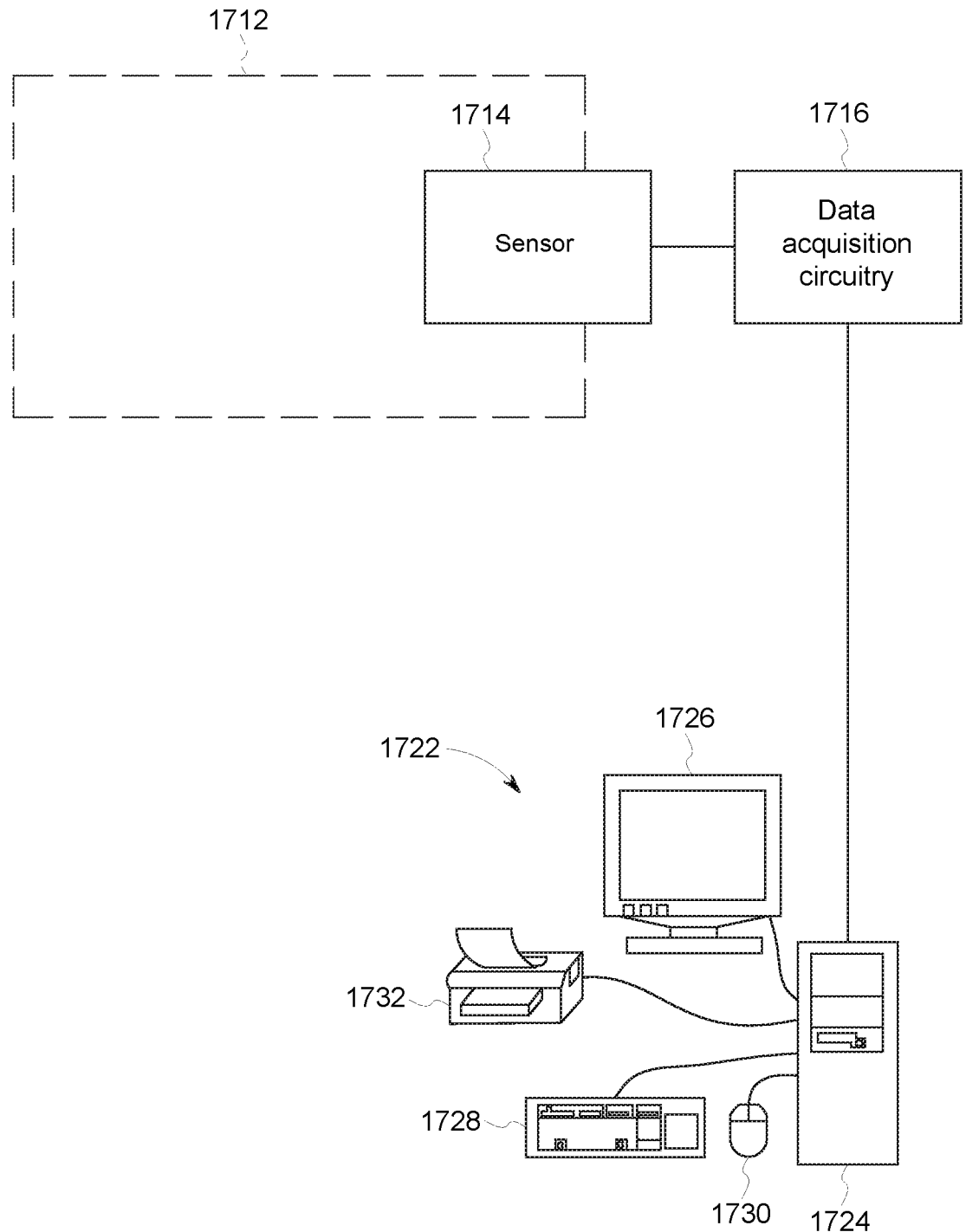
FIG. 2 is a block diagram of a system for assessing fluid according to an embodiment of the disclosure.

The sensor 5802 may also include data acquisition circuitry or sensing region circuitry (not shown), which may be similar to the data acquisition circuitry 1716 shown in FIGS. 2 and 3. The sensing region circuitry is configured to generate an electrical signal representative of the measured resonant impedance spectra. The electrical signal may be transmitted to a processing device with one or more processors, such as the sensor reader 5804, for analysis of the resonant impedance spectra to determine one or more properties of the industrial fluid. The one or more properties in one embodiment are both a concentration of water (or another external contaminant) in the fluid and an aging level of the fluid. The properties in another embodiment are both a concentration of water (or another external contaminant) and a concentration of at least one of acidic or basic components in the fluid.

The analysis of the resonant impedance spectra may be performed by comparing the extracted resonance parameters from the measured resonant impedance spectra from the electrodes in the sensing region (e.g., the sensing sub-regions 5808A, 5808B, and 5808C) to known resonance parameters of the same or a similar fluid at various controlled properties of the fluid, such as defined concentrations of water in the fluid or other external contaminant and at various age levels of the fluid. In an example in which water is the external contaminant, the tested fluid of interest may be determined to have a specific water concentration and a specific age level responsive to the measured set of resonance parameters matching a set of known resonance parameters associated with the specific water concentration and the given age level to a greater extent than the measured set of resonance parameters matches other sets of known resonance parameters associated with other concentrations of water and/or age levels. Statistical methods may be used to compare and "match" the measured resonance parameters to the known resonance parameters. The statistical method used may be a regression analysis, such as a linear regression, a nonlinear regression, or the like. In another example, a series of experiments may be performed using a single sensor to determine the measured resonance parameters of a resonant impedance spectral response of the sensor in a given industrial fluid at various concentrations of water or other external contaminant in the fluid and at various age levels of the fluid, which are the two or more variables that change across the series of experiments. The measured resonance parameters for the series of experiments may be plotted as data points on a graph, and may be used to develop a quantitative model that is used to predict the water or other external contaminant concentration and the age level of monitored fluids (where the water concentration or other external contaminant and the age are unknown). The quantitative model may be a transfer function for the sensing region 5808 broadly or for the individual sensing sub-regions 5808A, 5808B, and 5808C. Thus, measured resonance parameters from a resonance impedance spectral response may be input as variables into the quantitative model to predict water or other external contaminant concentration and aging level of the tested fluid.

The determination of the contaminant concentration in and/or age of the fluid of interest may be performed by establishing correlations between the spectral impedance responses of the sensing sub-regions 5808A, 5808B, and 5808C at multiple frequencies across the dispersion profiles of the fluid and the experimental impedance responses as determined initially via independent reference laboratory methods. Once these correlations (also known as transfer functions) are established, they are further utilized to predict the unknown measured concentrations. Such predictions may be performed by having the measured signals from the sensing sub-regions 5808A, 5808B, and 5808C at multiple frequencies across the dispersion profiles of the contaminant concentration and/or the age of the fluid, entering the values of these signals into the transfer functions or a single function, and obtaining the predicted values of the contaminant concentration and/or the age of the fluid. Depending on the transfer functions, one or more contaminants may be quantified from the measured signals from the sensing sub-regions 5808A, 5808B, and 5808C at multiple frequencies across the dispersion profiles of the contaminants concentration and/or the age of the fluid.

Figure 44:
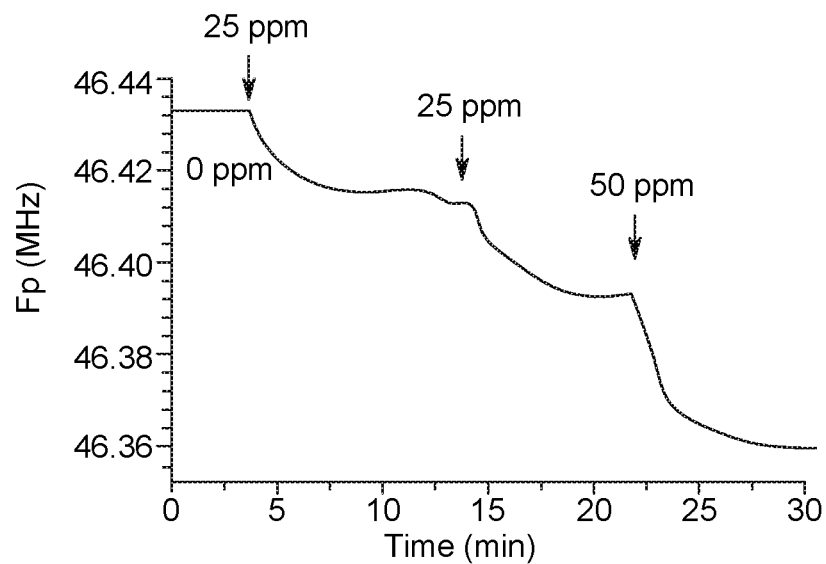
FIG. 44 depicts responses of a developed resonant sensor to water leaks into engine oil at levels of 25 ppm, 25 ppm, and 50 ppm each.

The concentrations of water or other external contaminants detected by the sensor 5802 may be down to 1 ppm. FIG. 44 depicts responses of this developed resonant sensor 5802 to water leaks into engine oil at levels of 25 ppm, 25 ppm, and 50 ppm each. The water levels indicate additions of water, so the second addition of water at 25 ppm results in doubling the amount of water added to the sample fluid, and the third leak level results in four times the concentration of water relative to the first leak level. The data in FIG. 44 illustrates that this sensor 5802 may detect the water leaks at the lowest tested level of 25 ppm with high signal-to-noise ratio quality, resulting in the ability to resolve 1 ppm of water leak with a signal-to-noise (S/N) ratio of 3.

Figure 45:
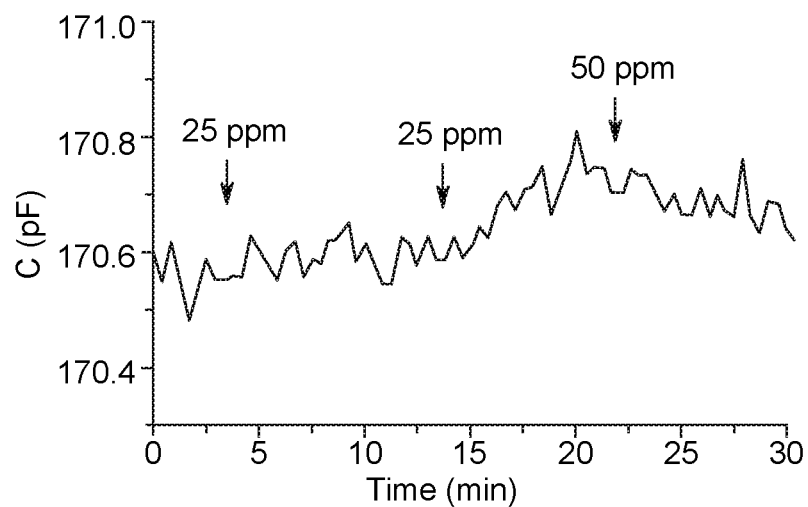
FIG. 45 depicts the response of a reference capacitance sensor to water leaks into engine oil at levels of 25 ppm, 25 ppm, and 50 ppm each.

The performance of this developed resonant sensor may be compared with the performance of a standard non-resonant capacitance sensor that is used as a reference capacitance sensor. The comparison may be performed by having both sensors in the same circulating-oil loop where water leaks may be introduced and presented to both sensors. Water leak levels may be 25 ppm, 25 ppm, and 50 ppm each. FIG. 45 depicts the response of the reference capacitance sensor to water leaks into engine oil at levels of 25 ppm, 25 ppm, and 50 ppm each. This figure illustrates that the reference capacitance sensor did not show an appreciable signal change responsive to the additions of water, likely due to noise. The experimental results indicate an inability of the reference capacitance sensor to distinguish among the different concentrations of water leaks.

Figure 46:
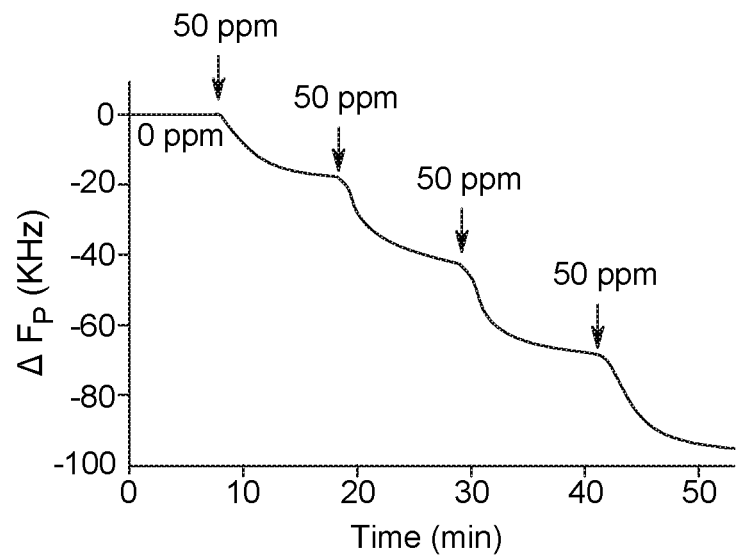
FIG. 46 shows the response of a multivariable resonant sensor to water leaks into engine oil responsive to the 50 ppm steps.
Figure 47:
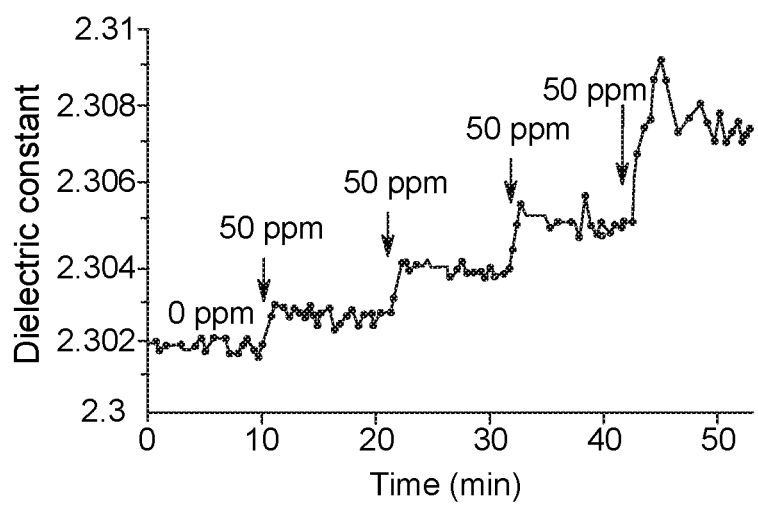
FIG. 47 depicts the response of a control tuning fork sensor to water leaks into engine oil at 50 ppm steps.

Benchmarking of the multivariable resonant sensor 5802 may be performed in comparison to a control or reference tuning fork sensor for quantitation of water leaks into oil. The tuning fork sensor is a mechanical resonator sensor that measures viscosity, density and dielectric constant of a test fluid. The benchmarking was performed by having both the resonant sensor 5802 and the reference tuning fork sensor in the same circulating-oil loop where water leaks were introduced and presented to both sensors. Water leaks levels were induced at 50-ppm steps. FIG. 46 shows the response of the multivariable resonant sensor to water leaks into engine oil responsive to the 50 ppm steps. FIG. 46 indicates that the sensor 5802 detects water leaks with a high signal-to-noise ratio. FIG. 47 depicts the response of the control tuning fork sensor to water leaks into engine oil at 50 ppm steps. The data in FIG. 47 demonstrates a significantly lower signal-to-noise ratio for the control tuning fork sensor relative to the sensor 5802.

In an experimental example, quantitation of water leaks at various stages of oil aging was performed using the sensor of one or more of the embodiments disclosed herein. The industrial fluid was automotive oil 10W-30. Water was added into the oil at different levels ranging from 25 parts per million (ppm) to 900 ppm when oil had three different aging levels. The aging levels were fresh (0% aging), old (100% aging), and intermediate (50% aging). The fresh oil indicates new oil, the old oil indicates oil with a mileage of 5000 miles in an automotive, and the intermediate oil is a 50/50 ratio of fresh and old oil. The oil may be considered new or fresh at or proximate to a beginning of a recommended fluid life of the oil, the oil may be considered old at or proximate to an end of the recommended fluid life of the oil, and the oil may be considered intermediate at or proximate to the middle of the recommended fluid life. For example, for an oil with a recommended fluid life of 5000 miles in a vehicle, the oil may be considered as new or fresh during the first 10% of the recommended fluid life (e.g., during roughly the first 500 miles), the oil may be considered as old for the last 10% of the recommended life (e.g., during roughly the final 500 miles before reaching 5000 miles) and during any additional miles beyond the recommended life, and the oil may be considered as intermediate for the middle 10% of the recommended life (e.g., during the period roughly between miles 2250 and 2750).

Figure 48:
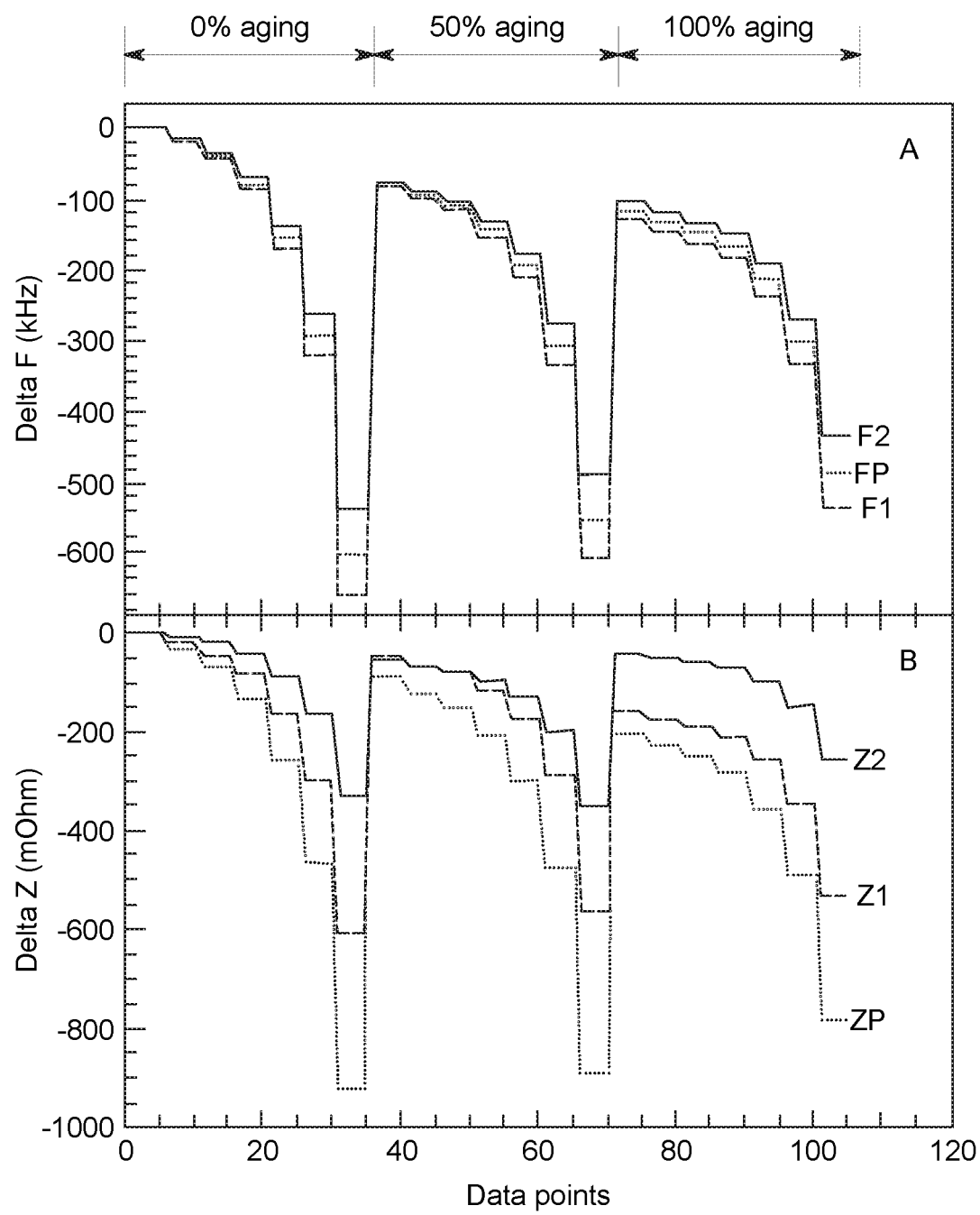
FIG. 48 is a plot depicting raw responses of resonance parameters of a resonant impedance spectra measured by the multivariable resonant sensor.
Figure 49:
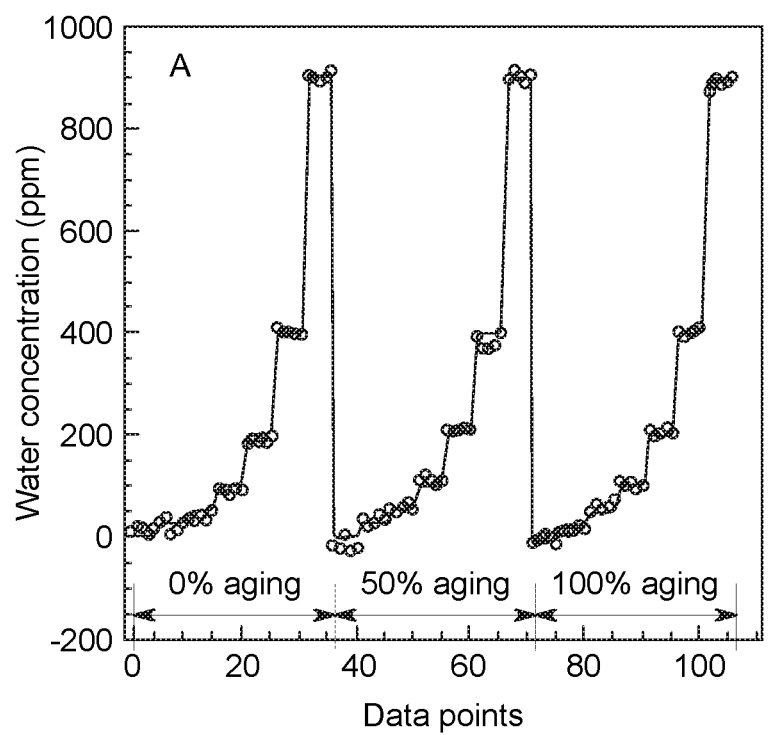
FIG. 49 shows the results of predicted versus actual concentrations for individual different levels of aging.
Figure 50:
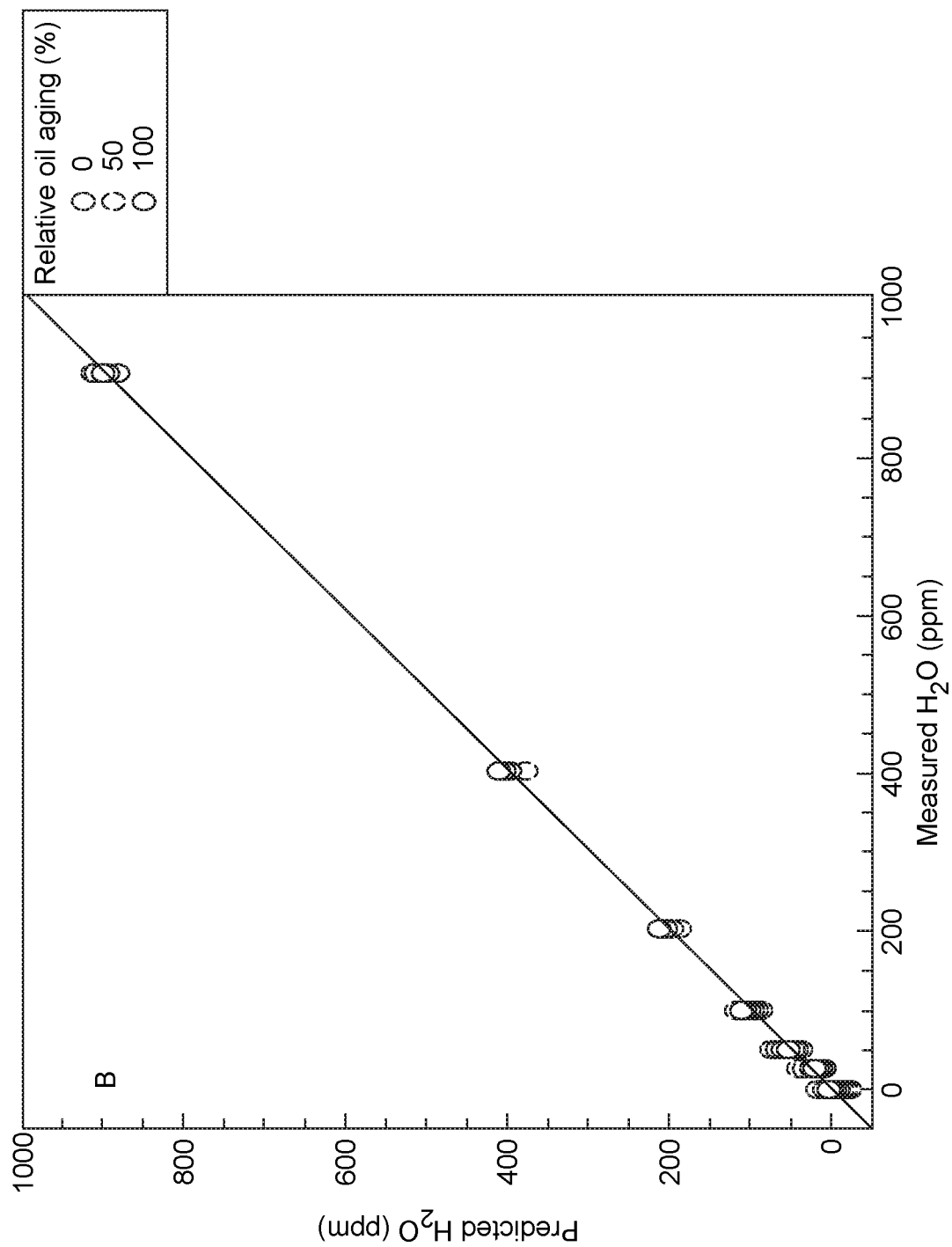
FIG. 50 shows a correlation plot between the actual and predicted water concentrations for three levels of oil aging (e.g., beginning of a recommended oil life, middle of the recommended oil life, or end of the recommended oil life).
Figure 51:
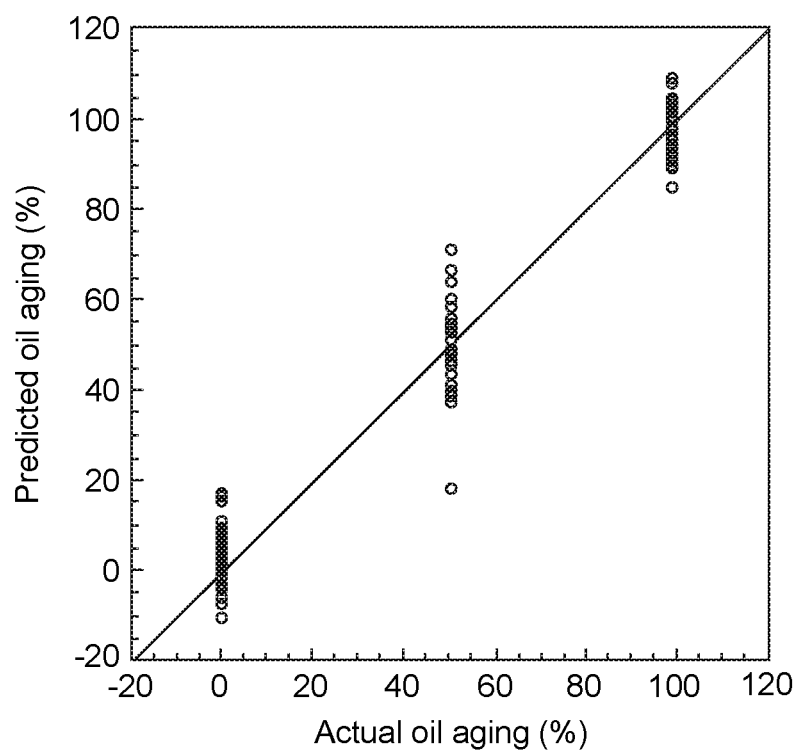
FIG. 51 is a correlation plot between actual and predicted oil aging using the multivariable resonant sensor.

FIG. 48 is a plot depicting the raw responses of the resonance parameters (e.g., F1, F2, Fp, Z1, Z2, and Zp) of the resonant impedance spectra measured by the sensor 5802 (shown in FIG. 43). As shown in FIG. 48, the sensor 5802 responds differently to the water additions depending on the aging levels of the oil samples. A quadratic transfer function was developed based on the raw data obtained in the experiment in order to predict water leaks into the oil. The results of the predicted versus actual concentrations are presented in FIGS. 49 and 50. FIG. 49 shows the results of the predicted versus actual concentrations for individual different levels of aging, and FIG. 50 shows a correlation plot between the actual and predicted water concentrations for the three levels of oil aging (e.g., beginning of a recommended oil life, middle of the recommended oil life, or end of the recommended oil life). The solid plot line represents a quantitative curve or model developed based on a series of experiments using known water concentrations in the oil and known age levels of the oil. The circular data points represent predicted water concentrations and age levels based on resonance parameters extracted or calculated from measured resonant impedance spectral responses of the sensor in contact with fluids of unknown water concentration and unknown age. These results demonstrate that the single developed multivariable sensor discriminates well between water leaks and oil aging and provides the ability to predict water concentrations. FIG. 51 is a correlation plot between actual and predicted oil aging using the sensor, which indicates that the single developed multivariable sensor also discriminates well between oil aging levels and provides the ability to predict oil aging. As a result, the single sensor is able to predict with significant accuracy both the concentration of water in the industrial fluid and the age of the fluid (relative to a recommended fluid life) without the need for multiple sensors to obtain such information.

Figure 52:
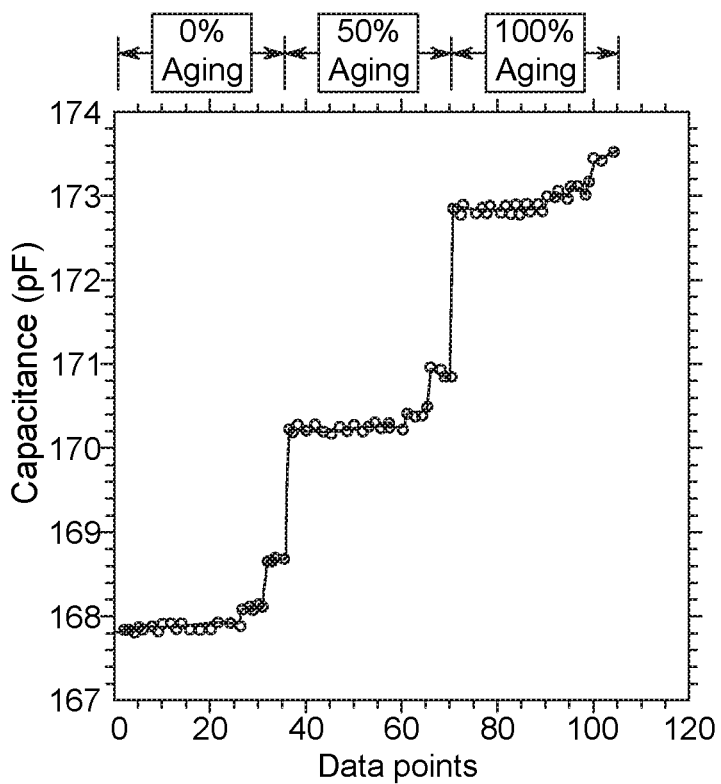
FIG. 52 depicts raw responses of a conventional capacitance sensor to water additions into differently aged oil samples.
Figure 53:
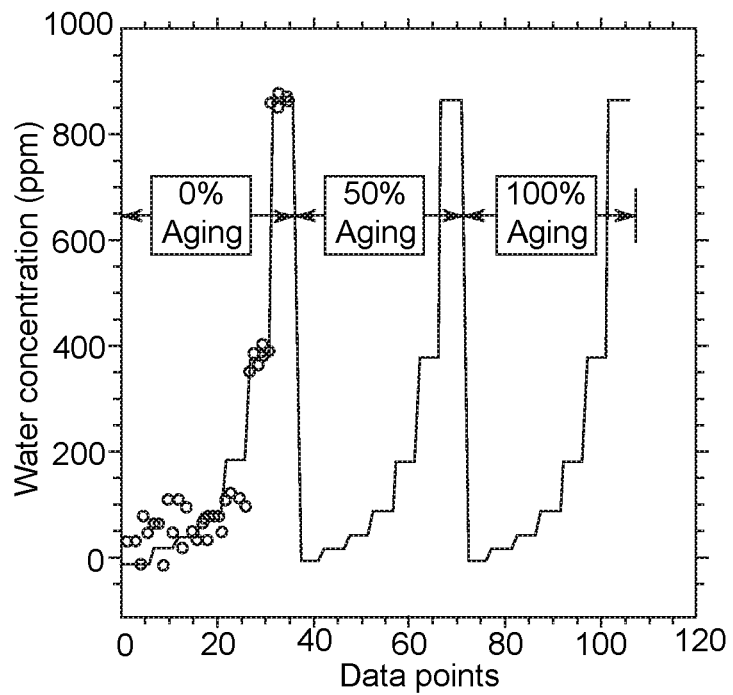
FIG. 53 plots results of predicted vs. actual concentrations of water concentrations for individual different levels of aging measured with a conventional capacitance sensor.

A similar experiment was performed using a conventional capacitance sensor using the same oil and the same water concentrations and aging levels. The results of the experiment indicate that the conventional capacitance sensor does not discriminate between water leaks and oil aging. The conventional capacitance sensor is not able to predict water concentrations at more than one aging level. Measurements were performed simultaneously with the conventional capacitance sensor and the multivariable resonant sensor (e.g., such as the sensor 5802 shown in FIG. 43). FIG. 52 depicts the raw response of the conventional capacitance sensor to water additions into differently aged oil samples. The capacitance sensor responded significantly to differently aged oil samples and less to the water additions into oil. A quadratic transfer function was developed to predict water leaks into fresh oil. Results of the predicted vs actual concentrations of water concentrations for individual different levels of aging measured with a conventional capacitance sensor are presented in FIG. 53. These results demonstrate that a conventional capacitance sensor does not discriminate between water leaks and oil aging and only provides the ability to predict water concentrations in fresh oil.

Figure 54:
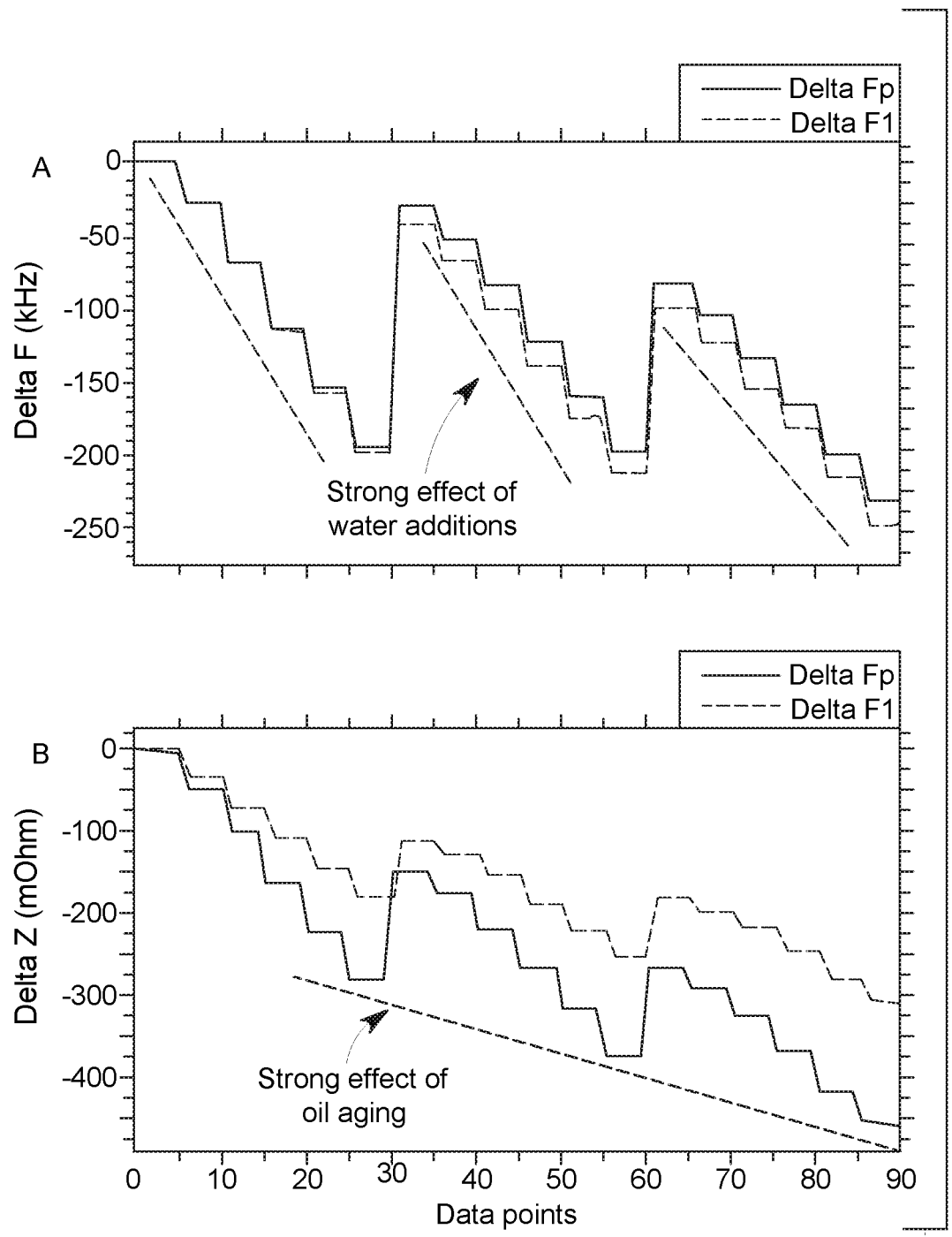
FIG. 54 depicts raw responses of (A) $F_p$, $F_1$, $F_2$ and (B) $Z_p$, $Z_1$, $Z_2$ of the multivariable resonant sensor to water additions into differently aged oil samples.

The performance of the developed multivariable resonant sensor was further benchmarked with the tuning fork sensor in quantitation of water leaks into oil at various stages of oil aging at one temperature. The employed model oil was automotive oil 10W-30 (AutoZone). Water was spiked into oil at 50-ppm levels providing steps of 50, 100, 150, 200, and 250 ppm of total water additions when oil had three levels of aging such as 50, 70, and 100%. FIG. 54 depicts raw responses of (A) $F_p$, $F_1$, $F_2$ and (B) $Z_p$, $Z_1$, $Z_2$ of the multivariable resonant sensor to water additions into differently aged oil samples. The data points corresponding to three levels of aging were from 0 to 30 (aging 50%), from 31 to 60 (aging 70%), and from 61 to 90 (aging 100%). The mileage for aged oil was 5000 miles. The 0% aging was fresh oil; the 100% was oil aged at 5000 miles; the 50% and 70% were 50/50 and 70/30 ratios of fresh and aged oil. The multivariable resonant sensor responded differently to the water additions into differently aged oil samples.

Figure 55A:
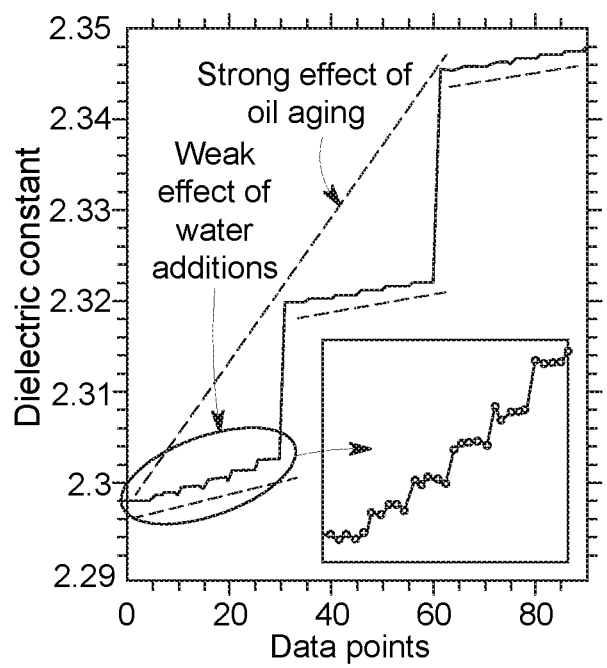
FIGS. 55A-C depict raw dielectric constant, density, and viscosity outputs, respectively, of a tuning fork sensor.
Figure 55B:
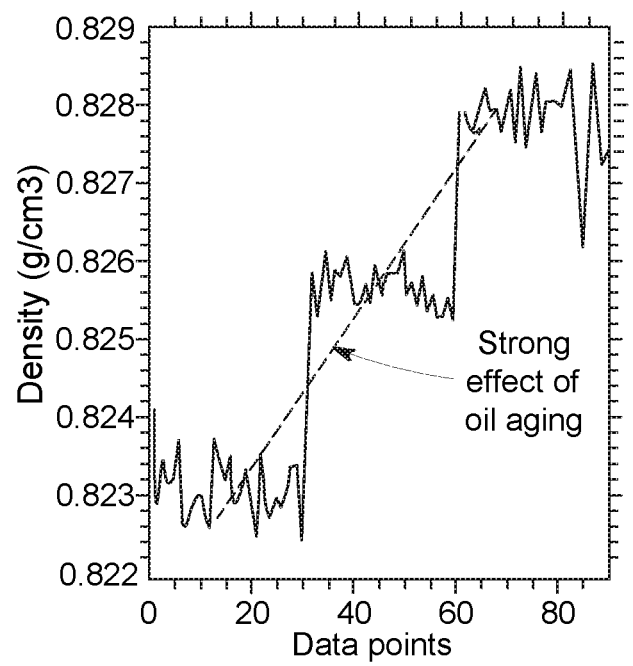
Figure 55C:
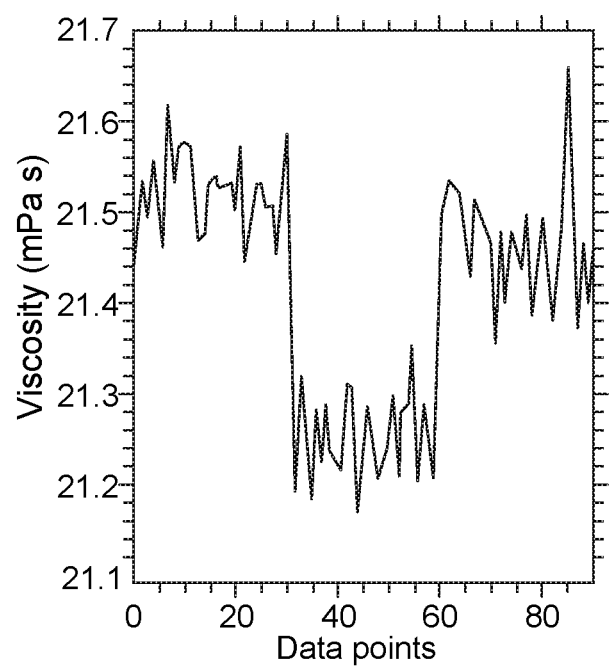

As a benchmark, quantitation of water leaks at various stages of oil aging was performed using the tuning fork. Measurements were performed simultaneously with the tuning fork and the multivariable resonant sensor (e.g., such as the sensor 5802 shown in FIG. 43). FIGS. 55A-C depict the raw dielectric constant, density, and viscosity outputs, respectively, of the tuning fork sensor. The tuning fork sensor responded strongly to differently aged oil samples and relatively much less to the water additions into oil as depicted in FIG. 55A. Response of the tuning fork to oil aging was dominating over the response to water leaks. In particular, dielectric constant response (FIG. 55A) showed strong response to aging (signal jumps at 30 and 60 points) and only relatively small effect of water leaks (small slopes of response over 0-30, 31-60, and 61-90 data points. The density (FIG. 55B) and viscosity (FIG. 55C) outputs showed only responses to aging.

Figure 56:
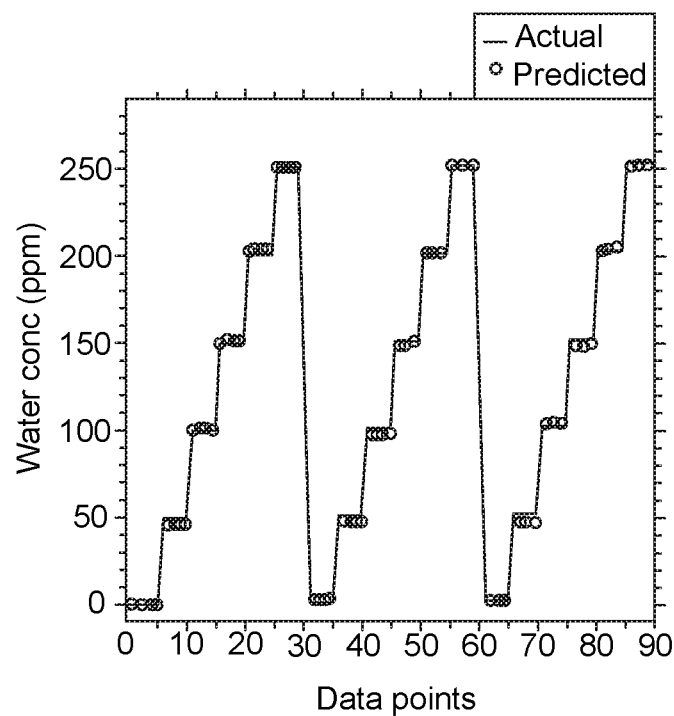
FIG. 56 shows the results of predicted and actual concentrations of water leaks into oil for the multivariable resonant sensor at different oil aging levels.
Figure 57:
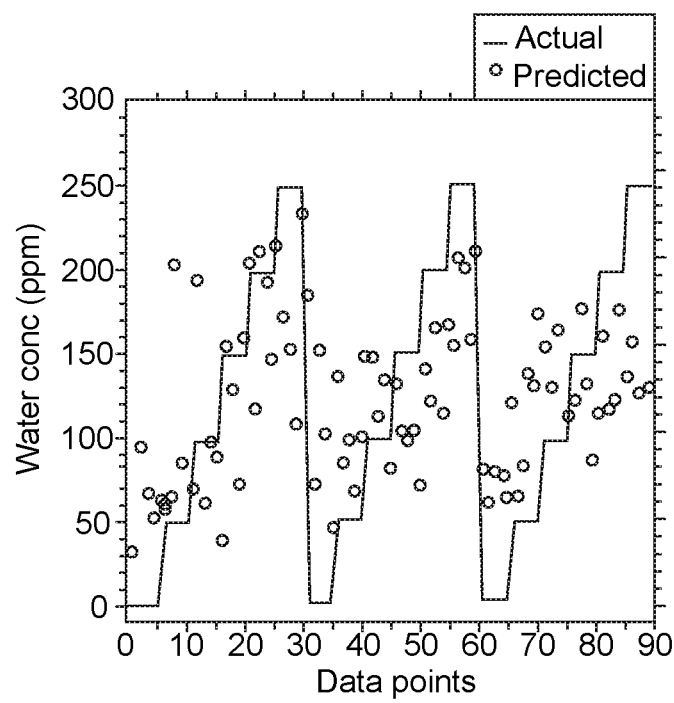
FIG. 57 shows the results of predicted and actual concentrations of water leaks into oil for the conventional tuning fork sensor at different oil aging levels.

Water leaks and oil aging levels were attempted to be quantified using the multivariable resonant sensor (e.g., the sensor 5802 shown in FIG. 43) and the conventional tuning fork sensor. Transfer functions were constructed for each sensor based on their respective outputs. The transfer functions were used to predict water leaks and oil aging levels. The residual prediction errors were evaluated by subtracting actual and predicted values of water leaks and oil aging. FIG. 56 shows the results of predicted and actual concentrations of water leaks into oil for the multivariable resonant sensor at different oil aging levels. These results demonstrate that a single developed multivariable sensor provided the ability to predict water concentrations, as illustrated by the close positioning of predicted values (open circles) to the actual values (solid line) in FIG. 56. FIG. 57 shows the results of predicted and actual concentrations of water leaks into oil for the conventional tuning fork sensor at different oil aging levels. These results demonstrate that the tuning fork sensor was unable to predict water concentrations in oil of different aging levels, as illustrated by the seemingly random scatter of predicted values (open circles) to the actual values (solid line) in FIG. 57.

To determine positions of resonances in the multi-resonant sensor, dielectric properties of fresh and aged oil samples in a broad range of frequencies from 100 Hz to 10 MHz were measured using a dielectric spectroscopy setup consisting of an Agilent 4294A precision impedance analyzer and an Agilent 16452A liquid test fixture. Dielectric spectra were transferred from the 4294A impedance analyzer to a data processing computer using a 4294A data transfer program available from Agilent as a Microsoft Excel macro and was analyzed as described in the 16452A test fixture manual to obtain the real and imaginary parts of the complex dielectric constant ($\varepsilon'$ and $\varepsilon''$, respectively). These measurements were used in the determination of the spectral dispersion properties of oils and allowed further downselection of operating frequencies for the multi-resonance sensor operation.

Figure 58A:
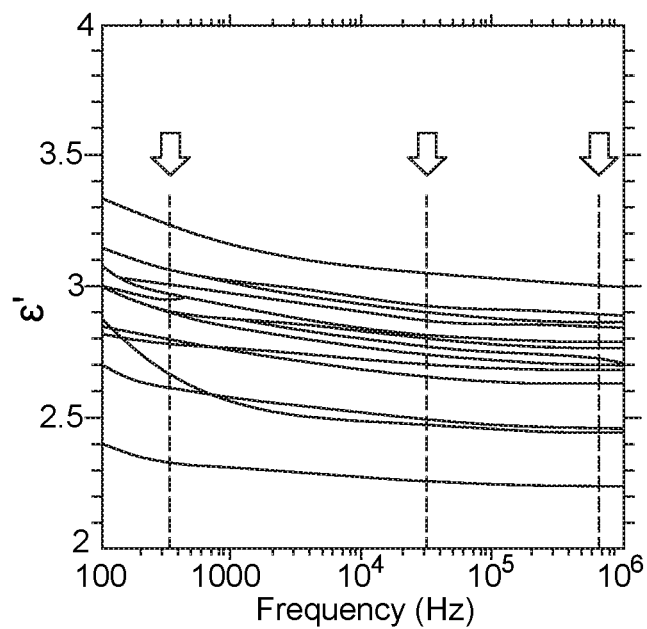
FIGS. 58A-B depict an application of the multiresonant sensor system for the correction for oil aging that shows an example of the selection of operating frequencies of the multiresonant sensor system across the spectral dispersion of locomotive oil.
Figure 58B:
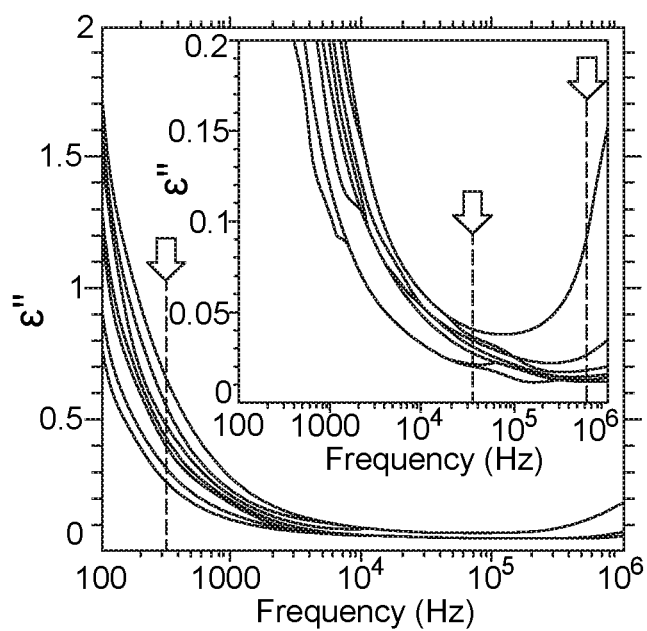
Figure 59A:
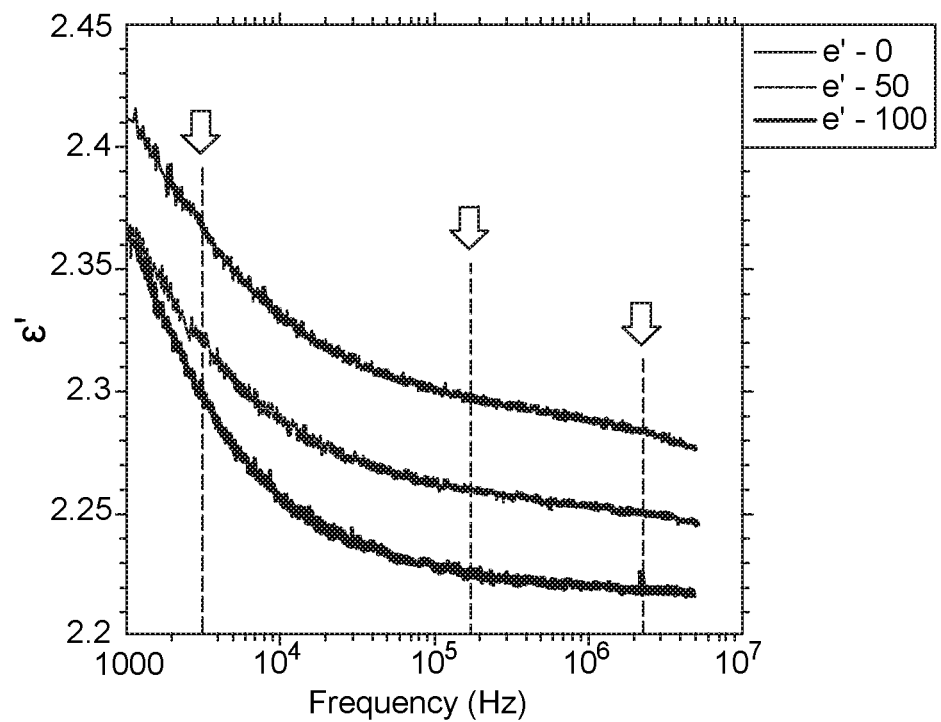
FIGS. 59A-B depict the real and the imaginary portions of the complex permittivity of the employed model automotive oil 10W-30 with three levels of aging such as 0, 50, and 100%.
Figure 59B:
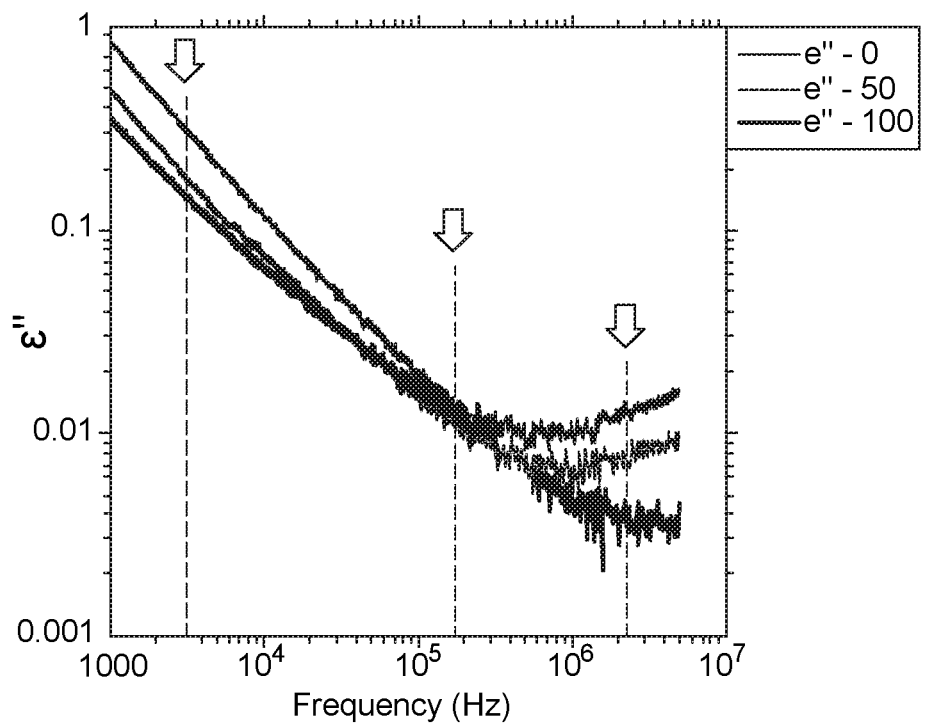

FIGS. 58A and 58B depict an application of the multi-resonant sensor system for the correction for oil aging that shows an example of the selection of operating frequencies of the multiresonant sensor system across the spectral dispersions shown for a range of fresh and used (aged) locomotive oils. FIG. 58A is the real part ($\varepsilon'$) and FIG. 58B is the imaginary part ($\varepsilon''$) of the complex dielectric constant of a locomotive oil. Arrows and dotted lines indicate initially selected regions for the multiresonant sensor operation. The real and the imaginary portions of the complex permittivity are depicted with the initially selected regions for the multiresonant sensor operation. These regions are selected based on the dispersion of $\varepsilon'$ and $\varepsilon''$ to capture spectral trends upon oil aging. FIGS. 59A and 59B depict the real and the imaginary portions of the complex permittivity of the employed model automotive oil 10W-30 with three levels of aging such as 0, 50, and 100% and illustrates trends of $\varepsilon'$ and $\varepsilon''$ upon oil aging, which is attractive for the selection of operating frequencies of the multiresonant sensor system. Arrows and dotted lines indicate initially selected regions for the multiresonant sensor operation.

In another experimental example, water leaks into oil were studied during the operation of a helicopter engine. The helicopter engine was a turboshaft CT7 helicopter engine made by GE. Water in the form of an emulsion was added to the oil sump prior to the engine start. A homogenizer was used to emulsify water with the CT7 engine oil. First, the loss of water in the oil during the helicopter engine operation was studied with the near-infrared spectroscopy using a Cary 500i UV-vis-NIR spectrophotometer (Varian, Inc., Santa Clara, Calif.) using quartz cuvettes with a 1-cm path length. Initially, oil samples with known amounts of water were measured to establish the relationship between near-infrared absorbance and water content. Next, samples were taken between the runs of the helicopter engine and analyzed with near-infrared spectroscopy for the presence of residual water. The 500 ppm water was added to the sump of the engine, and then the engine was allowed to run for specified time periods in the ground idle mode. Oil samples were taken between the runs and analyzed with near-infrared spectroscopy for the presence of residual water. The water presence was deduced from the characteristic water absorption band at 1900 nm after the measurement setup calibration with oil-water mixtures with the known water content. The results indicated that for a given concentration of 500 ppm water, water was completely eliminated from the oil in around five minutes on the ground idle. Thus, the water signature could be detected within the first few minutes after the engine start.

Figure 60A:
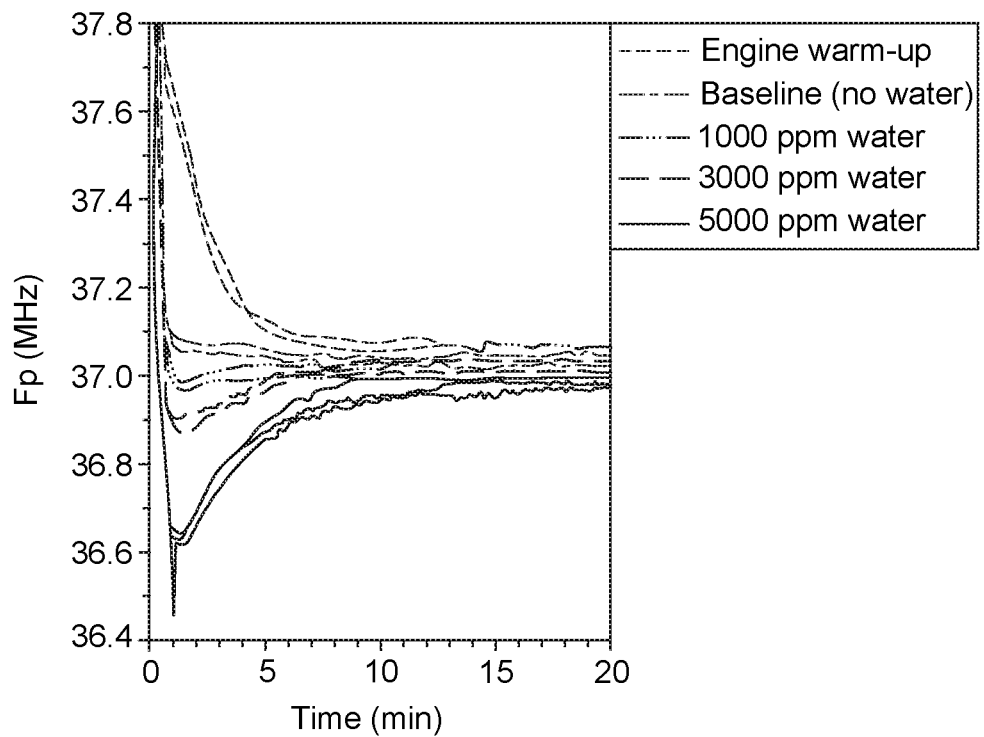
FIGS. 60A-B show the results of triplicate runs with for the engine warm-up, baseline (no added water), and water additions of 1000, 3000, and 5000 ppm, and the correlation between the sensor response and added water concentration, respectively.
Figure 60B:
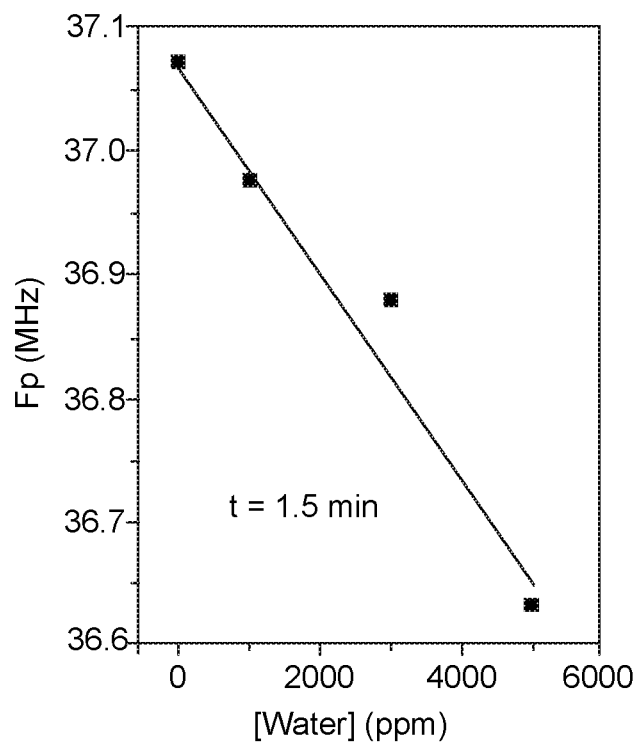

Detection of water concentrations in a turboshaft helicopter engine was further performed using the multivariable resonant sensor (e.g., such as the sensor 5802 shown in FIG. 43). The 4-cm$^2$ 100-μm-IDE-spacing sensor operating at around 38 MHz (in oil) was placed inside a 1-inch T-connector that was a part of a specially installed ⅜" OD bypass oil line connected to the engine to ensure oil flow through the sensor during the engine operation. Benchmarking of the performance of the multivariable resonant sensor was done by comparison with a conventional tuning fork sensor, installed sequentially. Measurements of water leaks were performed by adding water concentrations of 1000, 3000, and 5000 ppm and observing dynamic response patterns. Results of these experiments are summarized in FIG. 60A, which shows the results of triplicate runs with for the engine warm-up, baseline (no added water), and water additions of 1000, 3000, and 5000 ppm. The correlation between the sensor response and added water concentration was established by measuring sensor response after 1.5 min upon water addition, as shown in FIG. 60B.

Figure 61A:
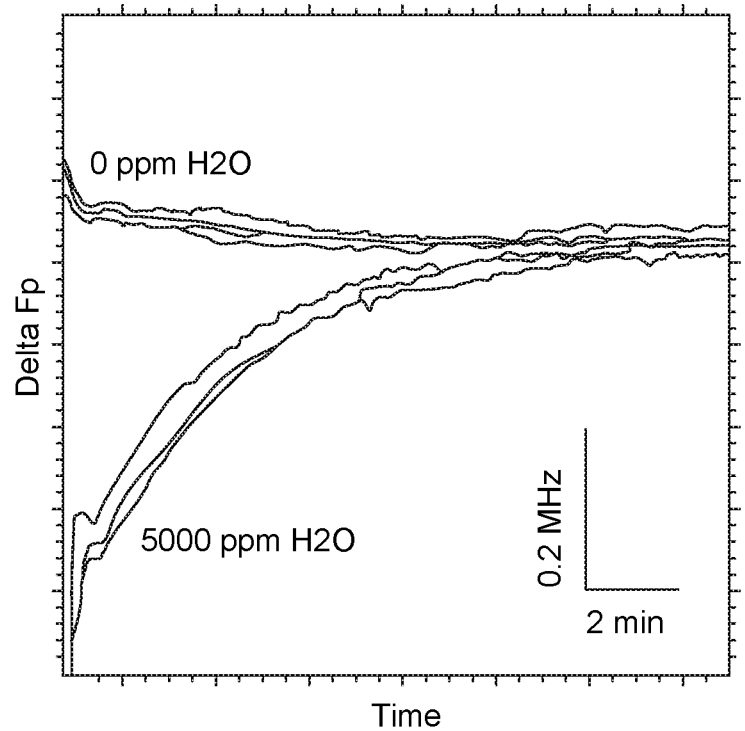
FIGS. 61A-B show responses of an installed multivariable resonant sensor and a tuning fork sensor, respectively, upon testing of engine oil of the turboshaft helicopter with an added 5000 ppm of water and observing dynamic response patterns.
Figure 61B:
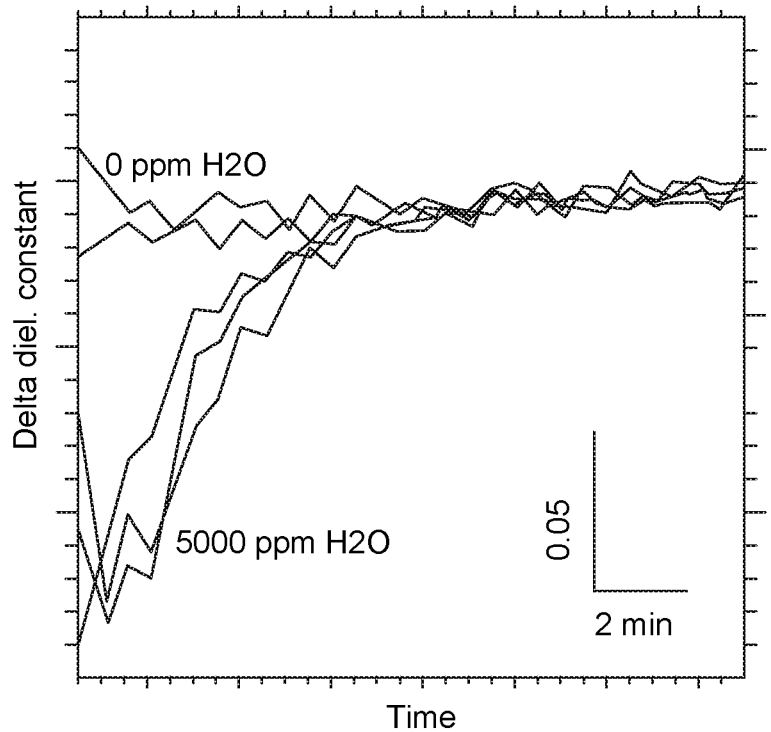

FIGS. 61A and 61B show responses of the installed multivariable resonant sensor and the tuning fork sensor, respectively, upon testing of engine oil of the turboshaft helicopter with an added 5000 ppm of water and observing dynamic response patterns. The tuning fork sensor response shown in FIG. 61B was corrected for the temperature fluctuation during the measurement. The estimated signal-to-noise ratio of both sensors was taken at their maxima, and the noise levels were taken upon water evaporation at stable response regions during individual runs. As shown in FIG. 61A, the signal-to-noise ratio of the multivariable resonant sensor was in the range of generally 230-525. As shown in FIG. 61B, the signal-to-noise ratio of the tuning fork sensor was in the range of generally 25-60. In FIG. 61B, the dielectric constant increases with the addition of water.

Figure 62:
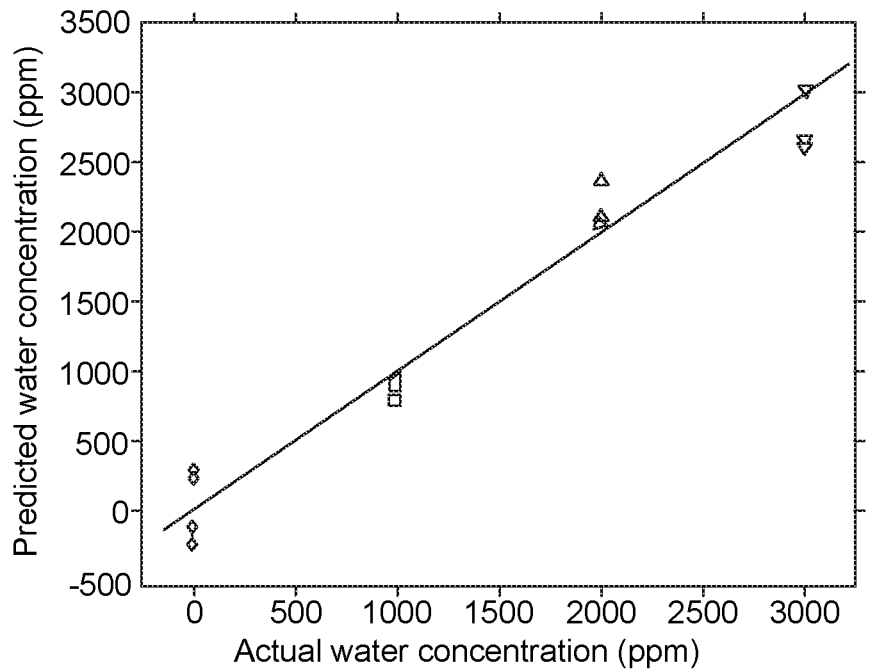
FIG. 62 illustrates results of predicted water concentrations versus actual water concentrations in different types of oils using a single transfer function.

Using an approach of selecting the appropriate frequency ranges as depicted in FIGS. 58A and 58B and FIGS. 59A and 59B, four types of automotive oil were measured with different levels of added water at concentrations of 0 ppm, 1000 ppm, 2000 ppm, and 3000 ppm. The different types of automotive oil were 0W-20, 10W-30, 15 W-40, and SAE30. FIG. 62 illustrates results of predicted water concentrations versus actual water concentrations in different types of oils using a single transfer function. The data in FIG. 62 illustrates the ability of the developed sensing methodology to detect and quantify an external contaminant such as water into diverse types of oil without effects of the type of oil.

Figure 63:
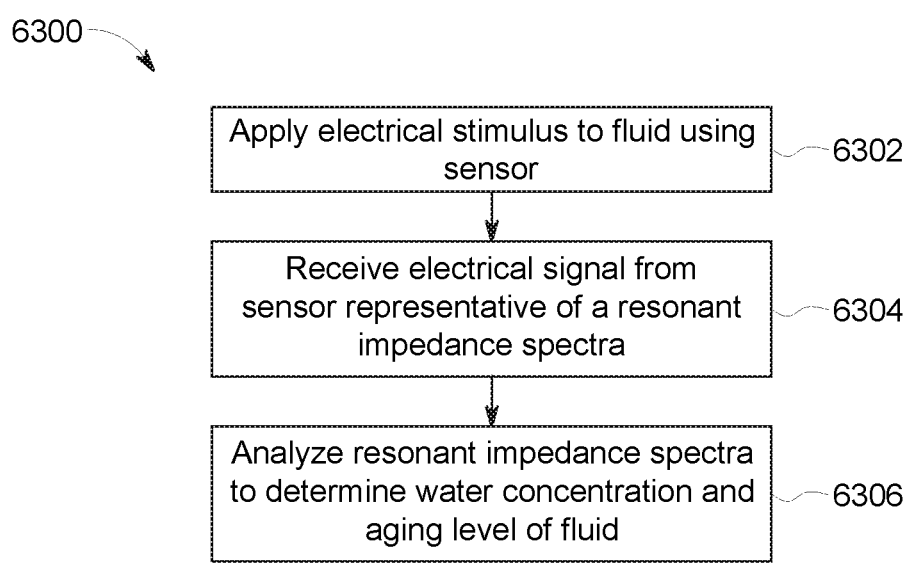
FIG. 63 is a flow chart representative of a method for determining multiple properties of an industrial fluid.

FIG. 63 is a flow chart representative of a method 6300 for determining multiple properties of an industrial fluid. At 6302, an electrical or electromagnetic stimulus is applied to an industrial fluid using a sensor. The "electrical stimulus" may additionally or alternatively be an electromagnetic stimulus. The sensor includes at least one resonant inductor-capacitor-resistor (LCR) circuit configured to generate the electrical stimulus. The electrical or electromagnetic stimulus is applied to the industrial fluid via multiple electrodes at a sensing region of the sensor in operational contact with the industrial fluid. Optionally, the sensor may include multiple LCR circuits that have different resonant frequencies. Applying the electrical or electromagnetic stimulus to the industrial fluid may include generating the electrical or electromagnetic stimulus to incorporate the resonant frequencies of the resonant LCR circuits such that the resonant impedance spectral response is measured over the resonant frequencies of the resonant LCR circuits. The method 6300 may also include tuning the electrical or electromagnetic stimulus generated by the at least one LCR circuit using one or more tuning elements. The tuning elements may include one or more inductors, capacitors, resistors, resonators, or impedance transformers.

At 6304, an electrical or electromagnetic signal is received from the sensor. The electrical or electromagnetic signal is representative of a resonant impedance spectral response of the sensing region in operational contact with the industrial fluid in response to the electrical or electromagnetic stimulus being applied to the industrial fluid. At 6306, the resonant impedance spectral response is analyzed to determine both a water concentration in the industrial fluid and an aging level of the industrial fluid based on the analyzed resonant impedance spectra. Although "water concentration" is mentioned, in other embodiments the concentration may be of another external contaminant other than water. The water or other external contaminant concentration in the industrial fluid and the aging level of the industrial fluid may be determined by comparing the extracted resonance parameters to known resonance parameters associated with various water or other external contaminant concentrations in the industrial fluid and various aging levels of the industrial fluid. The aging level of the fluid is determined by categorizing the fluid as three levels as one of fresh, old, or intermediate. The aging level of the fluid may be also determined by categorizing the fluid with more levels of aging where the number of levels of aging may be 8, 64, 128, or more. The number of aging levels determined by the sensor may depend on the developed transfer function between fluid aging and multivariable sensor response.

The determination of oil aging by levels is important for different applications. For example a two-level aging of oil means that level 1 is a fresh oil and level 2 is aged oil that requires oil replacement or some other action. The higher number of resolution levels of oil aging, the more accurate performed actions can be, including prognostic algorithms to predict the remaining life of oil and/or the machine or an industrial system or site.

Analyzing the resonant impedance spectra may include extracting resonance parameters of the resonant impedance spectra. The resonance parameters are at least some of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), and a zero-reactance frequency (Fz) at the imaginary part of the resonant impedance spectra.

In an alternative embodiment, the resonant impedance spectra are analyzed to determine both water concentration and acid concentration in the fluid. Acid concentration of an oil is useful for estimating an amount of depletion of additives, an amount of acidic contamination, and/or an amount of fluid degradation. Some industrial fluids such as engine oil may have additives added to the fluids that are designed to increase the stability of the fluids in extreme temperature environments. The additives may be acidic compounds that elevate the acid concentration of the fluid. However, as the fluid ages, the additives deplete over time. The reduced amount of additives in the fluid reduces the acidity or acid concentration of the fluid. On the other hand, acidic contamination and fluid degradation may have the reverse effect of increasing the acid concentration of the fluid. Acidic contamination refers to external acidic components that are undesirably introduced into the fluid via leak paths through the reservoir housing that holds the fluid. For example, acidic components may be introduced into the fluid through a leak path with other external contaminants, such as water. As the amount of acidic contaminants increases, the acid concentration of the fluid increases and the performance or effectiveness of the fluid, such as for providing lubrication and/or heat dissipation, may decrease. The acids in the fluid may reduce the performance of the fluid and/or the machine in which the fluid is used by increasing the viscosity of the fluid and forming gums and resins.

Furthermore, the fluid may degrade over time as the fluid ages, such that the components of the fluid break up into smaller constituents. The rate of degradation may be affected by the high temperatures of the environment and/or the type and amount of additives and contaminants in the fluid. For example, the fluid may degrade at a higher rate once the stabilizing additives are depleted. The additives may include anti-oxidants, such that the fluid oxidizes at a greater rate once the additives are depleted. Typically, as the fluid degrades with age, the fluid may break down into corrosive acids which increase the acid concentration of the fluid. The corrosive acids also reduce the performance of the fluid and can cause component failure (e.g., engine failure) if the fluid is not replaced by new fluid.

Typical stabilizing additives may be basic (e.g., alkaline) in nature to neutralize acids in oil. Acids in oil may be generated from combustion of the fuels and the combustion byproducts being absorbed by oil and/or by organic acids due to oxidation of oil during engine operation.

Monitoring the acid concentration of the fluid over time may be used to determine when to replace the fluid. For example, a lubricating fluid may contain a basic (alkaline) additive package. The base concentration of the fluid may gradually decrease over time as the basic (alkaline) additives are gradually depleted. After the basic additives are depleted, the acid concentration may gradually increase due to at least one of acidic contaminants that leak into the fluid or degradation of the fluid. By monitoring the initial decrease in the base concentration in the fluid and the subsequent increase in the acid concentration, the sensing system can be used to predict the concentration of an additive package in the oil, when the additives are depleted, if there is a significant acid contamination, when the fluid should be replaced due to high acid concentration that exceeds a predetermined threshold level, and/or the like. For example, a low acid concentration may indicate that the fluid is relatively new or fresh and/or that the concentration of the basic additive package is relatively high. Based on the information provided by the sensing system, responsive actions may be taken to improve the fluid quality and/or increase the life of the fluid and/or machine in which the fluid is used. For example, the machine may be scheduled for repair and/or replacement responsive to detection of an acid contamination, and/or the fluid may be replaced responsive to determination of a high acid concentration that exceeds the predetermined threshold level.

Acidic components and water are both polar components. Conventional sensors, such as conventional capacitive sensors like the one described with reference to FIG. 52, are not able to discriminate between different polar components in a signal response to identify the individual contributions of water and acidic components in the fluid. However, the multivariable resonant sensor of the embodiments described herein is able to individually detect both water concentration and acid concentration of a fluid using only the single sensor.

Figure 64:
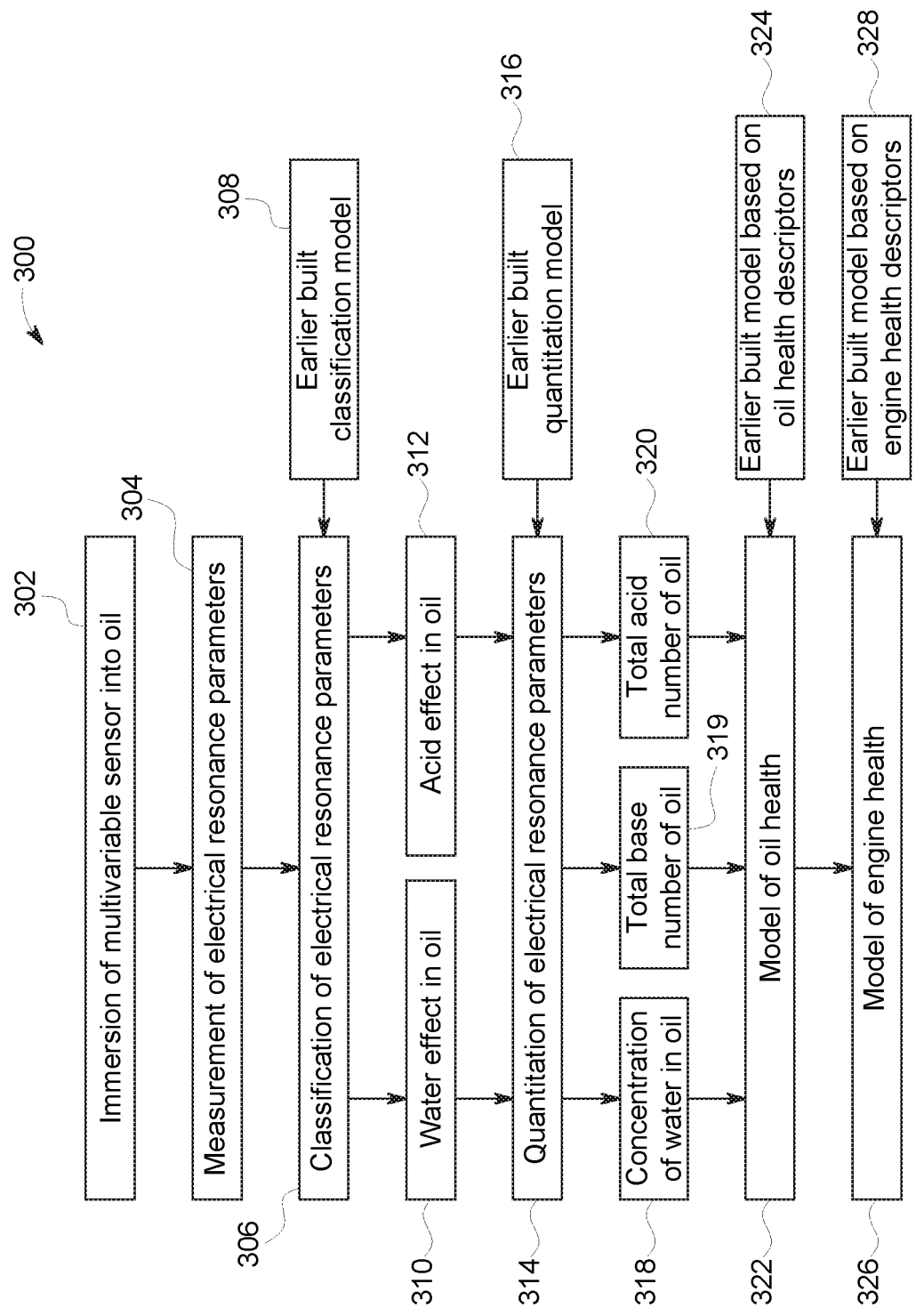
FIG. 64 is a flow diagram of method 300 for monitoring and assessing a lubricating oil according to another embodiment.

FIG. 64 is a flow diagram of method 300 for monitoring and assessing a lubricating oil according to another embodiment. Although the method 300 is described with reference to a lubricating oil, the method 300 may be performed on a different industrial fluid other than a lubricating oil. The method 300 shown in FIG. 64 is a modified version of the method 2860 for monitoring oil health shown in FIG. 14. For example, the method 300 may be used to independently monitor a concentration of water in oil, a concentration of acid in oil (e.g., total acid number of oil), and/or a concentration of base in oil (e.g., total base number of oil), while the method 2860 is used to determine a concentration of water in oil, a concentration of fuel in oil, and a temperature of the oil.

At 302, a multivariable resonant sensor (e.g., the sensor 1714 shown in FIG. 2 and/or the sensor 5802 shown in FIG. 43) is immersed into oil. The oil may be used for lubricating a machine having moving parts, such as an engine. The sensor is immersed into the oil such that a sensing region of the sensor is in operational contact with the oil. The sensor includes electrodes and a sensing region circuit electrically connected to the electrodes. The sensor is configured to apply an electrical stimulus to the oil via the electrodes. The electrical stimulus may be generated by the sensing region circuit. The sensing region circuit in an embodiment includes one or more LCR resonant circuits. The electrical stimulus applied to the oil may include multiple electrical fields and/or multiple resonant frequencies. For example, in an embodiment, the sensing region circuit includes four LCR resonant circuits (or tuning elements shown in FIGS. 4 and 5) that have different resonant frequencies. The electrical stimulus has a spectral frequency range that includes the four resonant frequencies of the four LCR resonant circuits.

At 304, electrical resonance parameters are measured responsive to the application of the electrical stimulus to the oil. The electrical resonance parameters are measured by receiving an electrical signal from the sensor that is representative of a resonant impedance response or spectra of the sensing region of the sensor in operational contact with the oil. The electrical signal may be transmitted from the sensor to one or more processors, such as the one or more processors of the sensor reader 5804 shown in FIG. 43. The resonant impedance response shows the response of the sensing region in contact with the oil over the frequency range that includes the multiple resonant frequencies of the LCR resonant circuits. As described above, the resonance parameters for the resonant impedance spectra (e.g., $(f)=Z_{re}(f) + jZ_{im}(f)$) may include one or more of the frequency position $F_p$ and magnitude $Z_p$ of $Z_{re}(f)$, the resonant $F_1$ and antiresonant $F_2$ frequencies, the magnitudes $Z_1$ and $Z_2$ of $Z_p(f)$, and zero-reactance frequency $F_z$ of $Z_{im}(f)$. In an embodiment, at least four resonance parameters are extracted from the impedance response. The one or more processors are configured to analyze the resonance parameters to quantitatively determine (e.g., estimate) the concentrations of water, acid, and/or base in the oil (as shown in steps 306, 308, 310, 312, 314, 316, 318, 319, 320). The one or more processors optionally may also be configured to estimate a health of the oil and/or the machine in which the oil is used based on the concentrations of water and acid in the oil (as shown in steps 322 and 324). Furthermore, the one or more processors may be configured to predict a remaining life of the oil and/or the machine based on the concentrations of water and acid in the oil (as shown in steps 326 and 328).

At 306, the electrical resonance parameters are classified, which may be done using an earlier-built classification model at 308, to assess the water effects in the oil at 310, the acid effect in the oil at 312, and/or the base effect in the oil at 319. The classification model may be built using spectral resonant parameters of a control group that is accumulated from previously-determined analyses of the effects of water and acid on the same or a similar type of oil. At 314, the electrical resonance parameters may be quantified using an earlier-built quantitation model at 316, to independently determine a concentration of water in the oil at 318, a concentration of base in the oil (e.g., a total base number (TBN) of the oil) at 319, and a concentration of acid in the oil (e.g., a total acid number (TAN) of the oil) at 320. Total Base Number (TBN) is the measure of basic chemical components or compounds in the oil. The basic components in engine oil may be components of additive packages. The basic components are used to neutralize acidic combustion products within the engine oil. The Total Acid Number (TAN) is the measure of acidic components of compounds in the oil. The acidic components in engine oil may be components of additive packages, by-products of combustion reactions, by-products of the chemical breakdown of oil, external acidic contaminants, or the like.

In an embodiment, the analysis of the resonant impedance response may be performed by comparing the extracted resonance parameters from the measured resonant impedance response to known resonance parameters of a control group. The parameters in the control group may be recorded resonance parameters of the same or a similar type of oil at various controlled properties of the oil, such as at different specific concentrations of water in the oil, different specific concentrations of acid in the oil, and/or different specific concentrations of base (alkali) in the oil. For example, a first subset of the resonance parameters in the control group may be associated with the same type of oil having a negligible amount of water and a first concentration of acid; a second subset of the resonance parameters in the control group may be associated with the same type of oil having a first concentration of water and the first concentration of acid; and a third subset of the resonance parameters in the control group may be associated with the same type of oil having the first concentration of water and a negligible amount of acid. The resonance parameters may also correspond to different specific concentrations of base in the oil. The data for the resonance parameters in the control group may be obtained via previous tests in the field and/or in the laboratory. The data for the previous tests may be stored and used to build the classification model and/or the quantitation model.

For example, a series of experiments may be performed using a single multivariable resonant sensor to determine the measured resonance parameters of a resonant impedance spectral response of the sensor in a given type of oil at various concentrations of water, acid, and base of the oil. The concentrations of water, acid, and base are variable that are modified across the series of experiments. The measured resonance parameters for the series of experiments may be plotted as data points on a graph, and may be used to develop the quantitative model that is used to predict the water concentration, the acid concentration, and/or the base concentration of monitored oil. The quantitative model may be a transfer function. Thus, the measured or extracted resonance parameters from a resonance impedance spectral response may be input as variables into the quantitative model to predict water concentration and acid concentration of the tested oil.

In an embodiment, the properties of the oil that is monitored by the sensor may be determined by comparing the extracted resonance parameters from the measured impedance response to the resonance parameters in the control group that are associated with known properties of the oil (e.g., known water, acid, and base concentrations). For example, the water concentration, the acid concentration, and the base concentration in the oil may be determined by matching the extracted resonance parameters to a specific subset of resonance parameters in the control group. For example, if the extracted resonance parameters more closely match or align with the resonance parameters of the second subset of resonance parameters described above (relative to the matching or alignment with the resonance parameters of the first and third subsets), then the measured oil is determined to have the first concentration of water and the first concentration of acid. Statistical methods may be used to compare and match the measured resonance parameters to the control group of known resonance parameters. The statistical method used may be a regression analysis, such as a linear regression, a nonlinear regression, or the like. Although only three subsets of resonance parameters are mentioned above, the quantitation model may have more than three subsets in order to provide more accurate determinations of the water concentration, the acid concentration, and/or the base concentration in a sample of oil. For example, the one or more processors may be configured to determine the concentration of water in an oil at 100, 300, 500, or more different levels or concentrations such as part per million concentrations, and may be configured to independently determine the concentration of acid and base within the same oil sample at 100, 300, 500, or more different levels or concentrations in order to provide an accurate determination of both properties.

At 322, the concentrations of water, acid, and base in the oil may be used to generate or update a model of oil health, which may be based on an earlier-built model using oil health descriptors at 324. In general, a relatively high concentration of water and/or a relatively significant increase in the concentration of water in the oil may signal poor oil health. The significant increase in water concentration may indicate a leak condition that should be addressed. Furthermore, a relatively high concentration of acid and/or a relatively significant increase in the acid concentration may signal poor oil health, especially if the oil is not fresh or new. For example, if the oil is new, the high concentration of acid may be at least partially due to the presence of stabilizing additives added to the oil, such that the oil may be in good health. But, as the oil ages and the additives deplete, an increase in acid concentration (and/or a decrease in base concentration) may indicate the introduction of an acidic contaminant and/or degradation (e.g., oxidation) of the oil, indicating poor oil health. The oil health descriptors may include threshold levels or ranges of water, acid, and base, and may also include threshold rates of change for the concentrations of water, acid, and base. The oil may be considered to have good health if the determined concentrations of water, acid, and base are all within the designated threshold levels. The oil health descriptors may include multiple thresholds for the water concentration, acid concentration, and base concentration. For example, if the acid concentration of the oil exceeds a first threshold, the model of oil health may indicate that the oil should be replaced within a designated period of time (or miles, revolutions, etc.) to avoid the oil degrading to a level of poor health that could damage the machine. Furthermore, if the acid concentration of the oil exceeds a second threshold that is greater than the first threshold, the model of oil health may indicate that the oil has a poor quality and should be replaced immediately without further operation of the machine until the oil is replaced and/or the machine is repaired (e.g., if a contamination leak is detected).

At 326, the concentrations of water, acid, and/or base in the oil may be used to generate or update a model of the health of the engine (e.g., or another machine in which the oil is disposed), which may be based on an earlier-built model using engine health descriptors at 328. For example, if the engine is operated with a poor quality of oil, the health of the engine may suffer, reducing the expected performance and/or operational lifetime of the engine. On the other hand, if the oil in the engine is maintained in good health such that the oil is replaced before the oil degrades to a poor health condition, then the engine may be determined to have a good health. The health of the oil and the engine may be used to predict the remaining operational lifetimes of the oil and the engine using the models at steps 322 and 326.

Figure 65A:
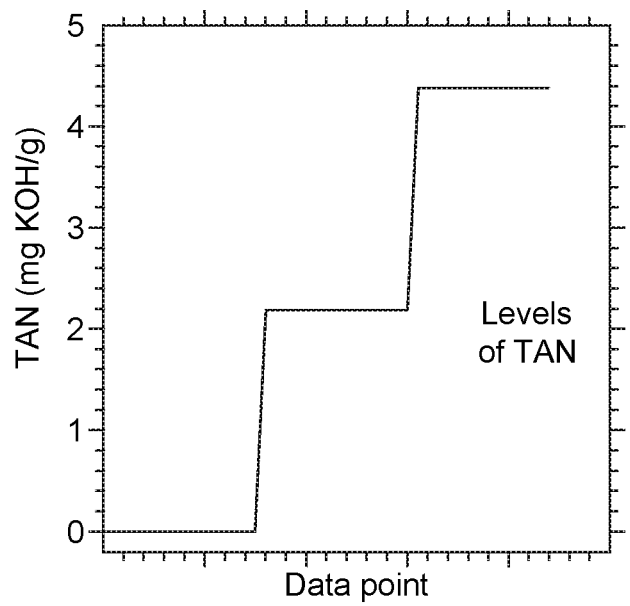
FIGS. 65A-B depict an experimental setup showing three different acid levels in a sample of oil and three different water levels in the sample of oil according to an embodiment.
Figure 65B:
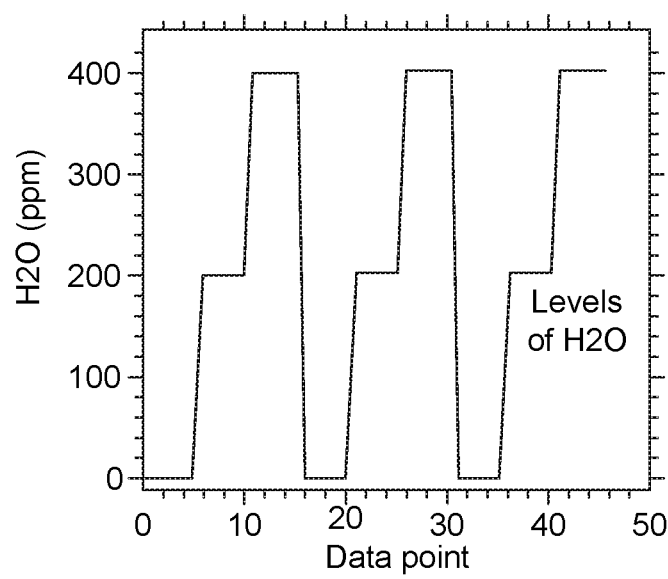

FIGS. 65A and 65B depict an experimental plan showing three different acid levels in a sample of oil and three different water levels in the sample of oil according to an embodiment. The experimental plan was tested to validate the detection of independent changes of two types of polar additives in oil (e.g., acid and water) using the multivariable resonant sensor described herein. The resonant sensor provides simultaneous measurements of at least two outputs. As shown in FIG. 65A, the different levels of total acid number (TAN) in the oil during the experiment were 0, 2, and 4 mg KOH/g, which was prepared using decanoic acid. As shown in FIG. 65B, the different levels of water in the oil were 0, 200, and 400 ppm. The goal of the testing was to resolve various TAN amounts at different levels of water in oil. As shown in FIGS. 65A and 65B, oil samples at each of the different levels of TAN were injected with different amounts of water such that nine different sample scenarios were tested.

Measurements of the resonance impedance of sensors were performed with a network analyzer under computer control using LabVIEW. The network analyzer was used to scan the frequencies over the range of interest and to collect the impedance response from the sensors. Collected impedance data was analyzed using KaleidaGraph (Synergy Software, Reading, Pa.) and PLS_Toolbox (Eigenvector Research, Inc., Manson, Wash.) operated with Matlab (The Mathworks Inc., Natick, Mass.). The multivariable response of the resonant transducers originates from the measured whole resonance spectra of the transducer followed by the processing of these spectra using multivariate analysis tools. The resonance impedance spectra $(f)=Z_{re}(f)+jZ^{im}(f)$ of the resonant transducer were measured. Several parameters from the measured (f) spectra were calculated that included the frequency position $F_p$ and magnitude $Z_p$ of $Z_{re}(f)$ and the resonant $F_1$ and antiresonant $F_2$ frequencies, their impedance magnitudes $Z_1$ and $Z_2$ of $Z_{im}(f)$, and zero-reactance frequency $F_z$ of $Z_{im}(f)$.

Figure 66:
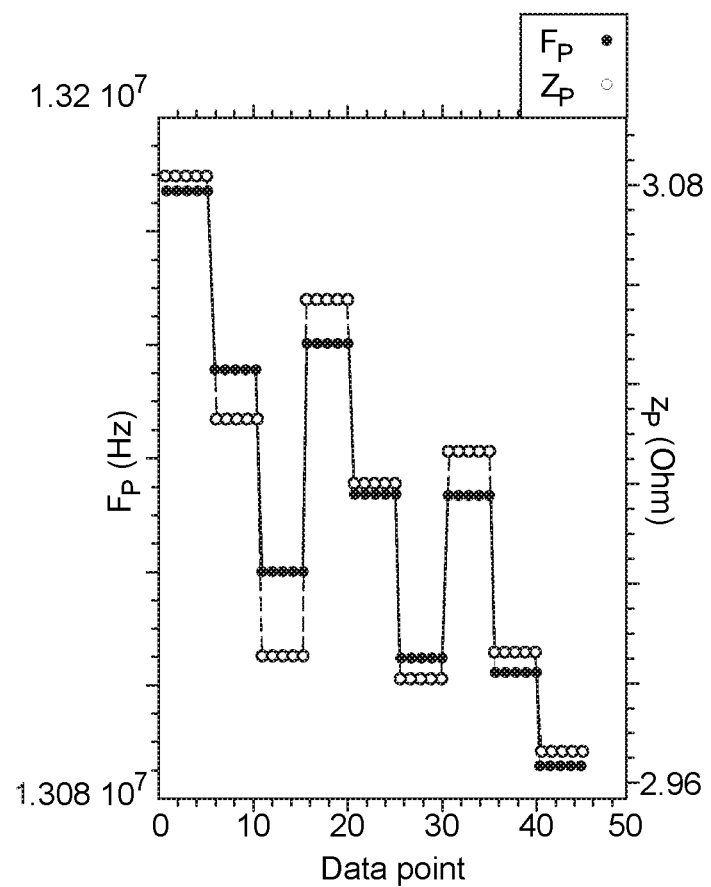
FIG. 66 plots the resonance parameters $F_p$ (in Hz) and $Z_p$ (in Ohm) of the measured impedance response of the oil samples to the electrical stimulus of the multivariable resonant sensor in the experiment described in FIGS. 65A-B.

FIG. 66 plots the resonance parameters $F_p$ (in Hz) and $Z_p$ (in Ohm) of the measured impedance response of the oil samples to the electrical stimulus of the multivariable resonant sensor in the experiment described in FIGS. 65A and 65B.

Figure 67:
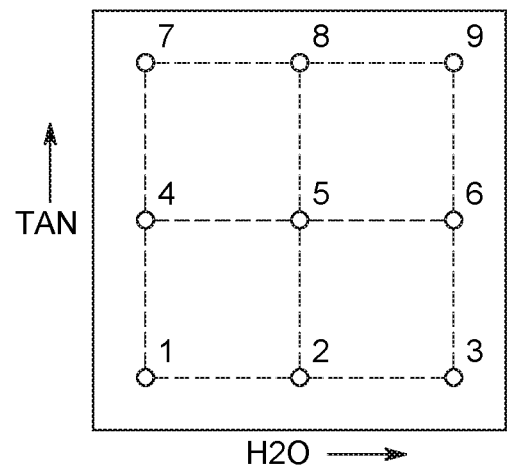
FIG. 67 depicts an experimental grid of nine samples with varying total acid number (TAN) and water levels according to the experiment described in FIGS. 65A-B.

FIG. 67 depicts an experimental grid of nine samples with varying TAN and water levels according to the experiment described in FIGS. 65A and 65B. For example, sample 1 represents the oil sample that includes 0 mg KOH/g TAN and 0 ppm water; sample 2 represents the oil sample including 0 mg KOH/g TAN and 200 ppm water; and sample 3 represents the oil sample including 0 mg KOH/g TAN and 400 ppm water. Samples 4-6 represent the oil samples including 2 mg/KOH/g TAN and 0, 200, and 400 ppm water, respectively. Samples 7-9 represent the oil samples including 4 mg/KOH/g TAN and 0, 200, and 400 ppm water, respectively.

Figure 68:
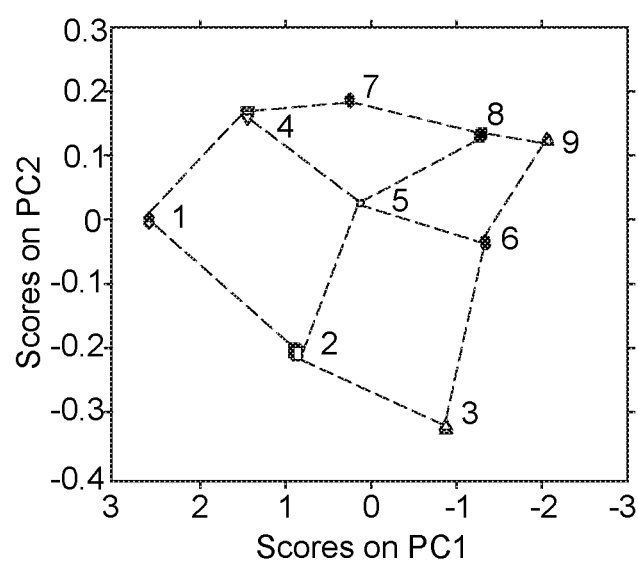
FIG. 68 depicts a scores plot of a developed PCA model illustrating spectral relation between sensor responses to the different types of contamination in the nine oil samples shown in FIG. 67.

FIG. 68 depicts a scores plot of a developed Principal Components Analysis (PCA) model showing Principal component 1 (PC1) vs. Principal component 2 (PC2) illustrating spectral relation between sensor responses to the different types of contamination in the nine oil samples shown in FIG. 67. As shown in FIG. 68, the experimental grid from FIG. 67 is visible in the scores plot, which indicates an ability to discriminate between all nine points of the experimental grid of samples using the PCA. For example, the experimental grid in FIG. 68 is a distorted version of the grid shown in FIG. 67, but all nine points are visible in the distorted view and have different coordinates in the scores plot.

Figure 69A:
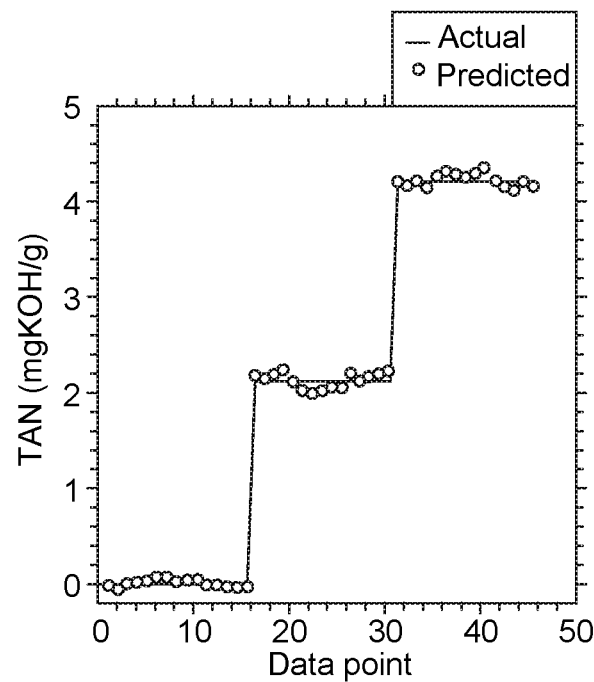
FIGS. 69A-B plot the results of predicted and actual TAN levels for the different samples of oil tested using the multivariable resonant sensor and the residual error of the TAN prediction, respectively.
Figure 69B:
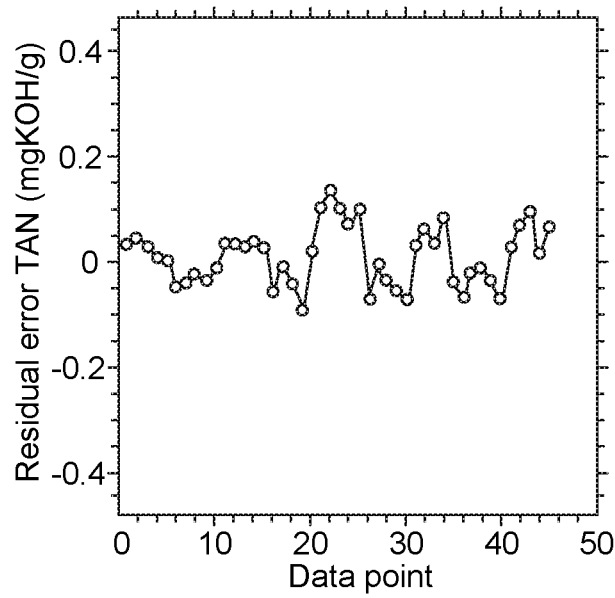

In the experimental methodology, the TAN and water levels were further determined or predicted using a multivariate regression technique. FIG. 69A plots the results of predicted and actual TAN levels for the different samples of oil tested using the multivariable resonant sensor. FIG. 69B plots the residual error of the TAN prediction using the multivariable resonant sensor. The results shown in FIGS. 69A and 69B illustrate that the multivariable sensor quantifies TAN in oil samples having different amounts of water therein with less than ±0.2 mgKOH/g residual error. Therefore, the multivariable resonant sensor is able to predict a TAN level (e.g., an acid concentration) in an oil sample, regardless of whether or not the oil sample includes a non-negligible concentration of water or other polar additives therein.

Figure 70A:
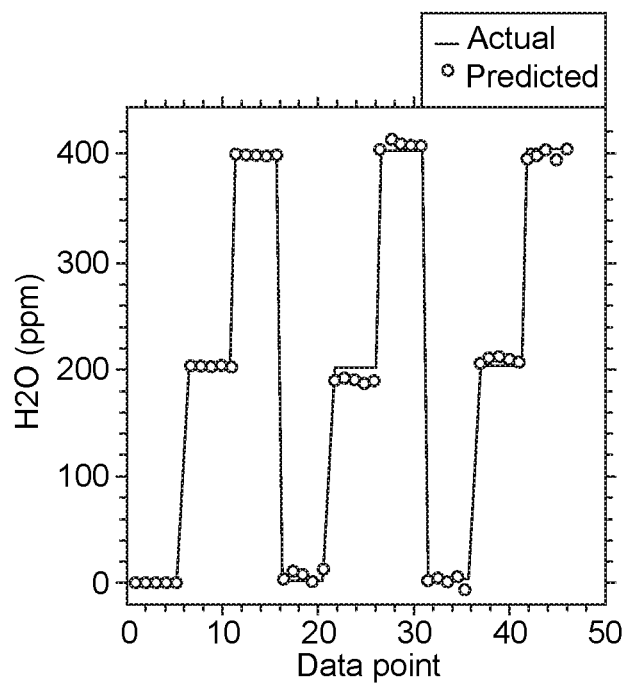
FIGS. 70A-B plot the results of predicted and actual water concentrations in oil for the different samples of oil tested using the multivariable resonant sensor and the residual error of the water concentration prediction, respectively.
Figure 70B:
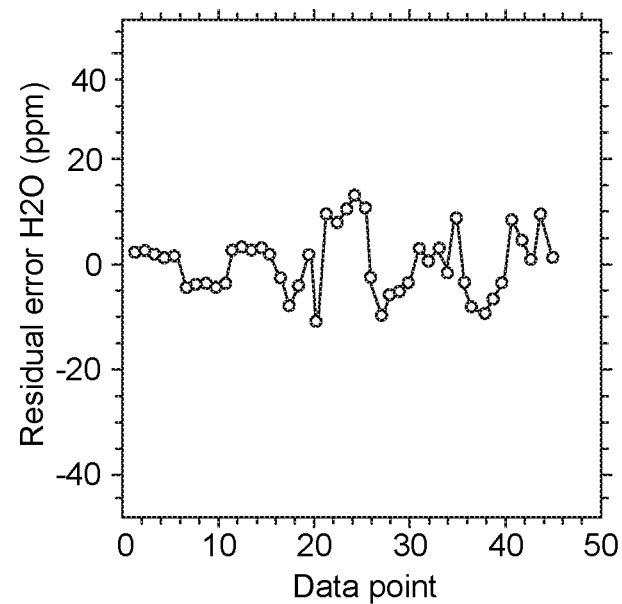

FIG. 70A shows the results of predicted and actual concentrations of water in oil for the different samples of oil tested using the multivariable resonant sensor at different TAN levels. FIG. 70B plots the residual error of the water concentration prediction using the multivariable resonant sensor. The results shown in FIGS. 70A and 70B illustrate that the multivariable sensor quantifies water concentrations in oil samples having different amounts of acid therein with less than ±20 ppm residual error. Therefore, the multivariable resonant sensor is able to predict a concentration of water in an oil sample, regardless of whether or not the oil sample includes a non-negligible concentration of acid or other polar additives therein. Furthermore, the single multivariable resonant sensor is able to predict both a water concentration and a TAN level of an oil sample based on a single spectral impedance response of the sensor in contact with the oil.

Figure 71:
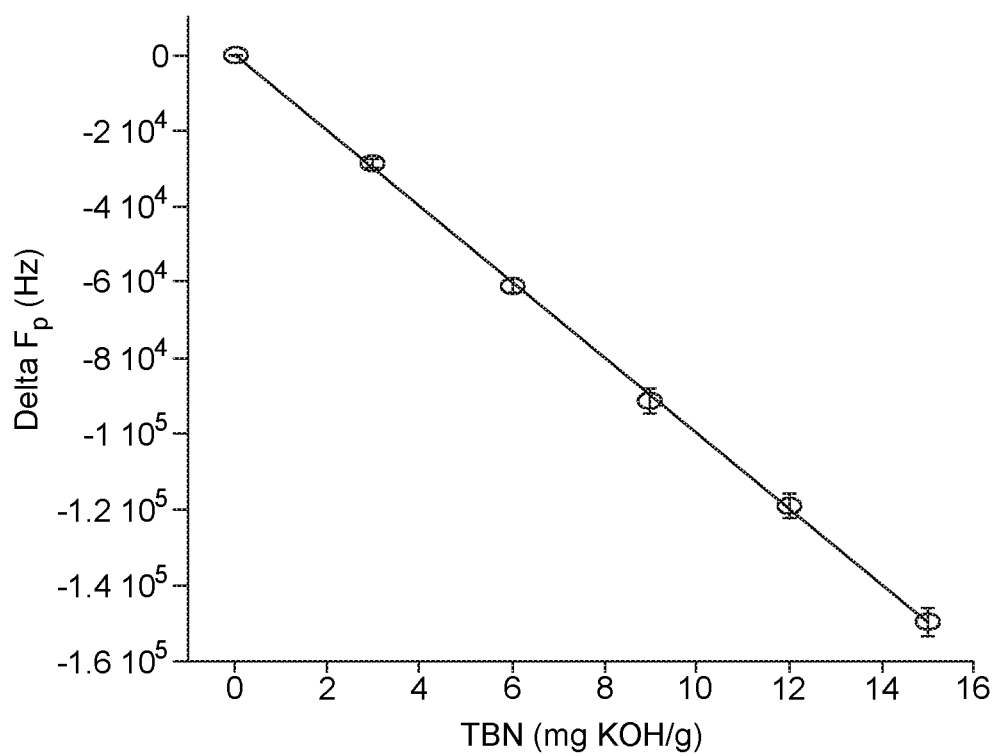
FIG. 71 illustrates a calibration plot of resonance parameter $F_p$ of the measured impedance response of oil samples with different total base number (TBN) levels to an electrical stimulus of the multivariable resonant sensor.

FIG. 71 illustrates a calibration plot of resonance parameter $F_p$ of the measured impedance response of oil samples with different total base number (TBN) levels to an electrical stimulus of the multivariable resonant sensor. The results shown in FIG. 71 illustrate that the multivariable sensor quantifies TBN levels in oil samples with a linear sensor response over a TBN range from 0 to 15 mg KOH/g.

Figure 72:
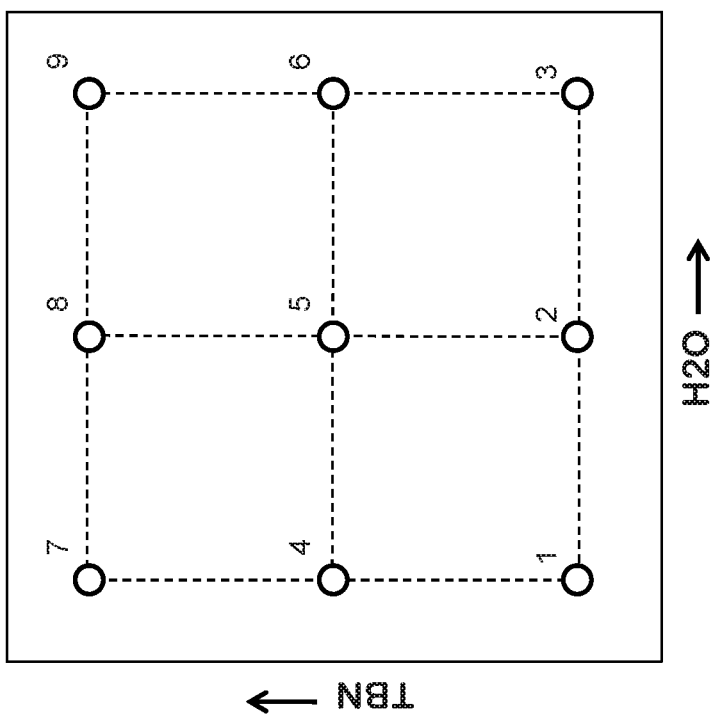
FIG. 72 depicts an experimental grid of nine oil samples with varying TBN and water levels in the oil.

FIG. 72 depicts an experimental grid of nine samples with varying TBN and water levels in locomotive engine oil. For example, sample 1 represents an oil sample that includes 0 mg KOH/g TBN and 0 ppm water; sample 2 represents an oil sample including 0 mg KOH/g TBN and 29 ppm water; and sample 3 represents an oil sample including 0 mg KOH/g TBN and 58 ppm water. Samples 4-6 represent oil samples including 3 mg/KOH/g and 0, 29, and 58 ppm water, respectively. Samples 7-9 represent oil samples including 6 mg/KOH/g and 0, 29, and 58 ppm water, respectively. These relatively small concentrations of TBN and water were selected as the nine samples to demonstrate the applicability of the developed sensor. Such low concentrations of TBN and water are difficult to measure reliably using known available sensors.

Figure 73:
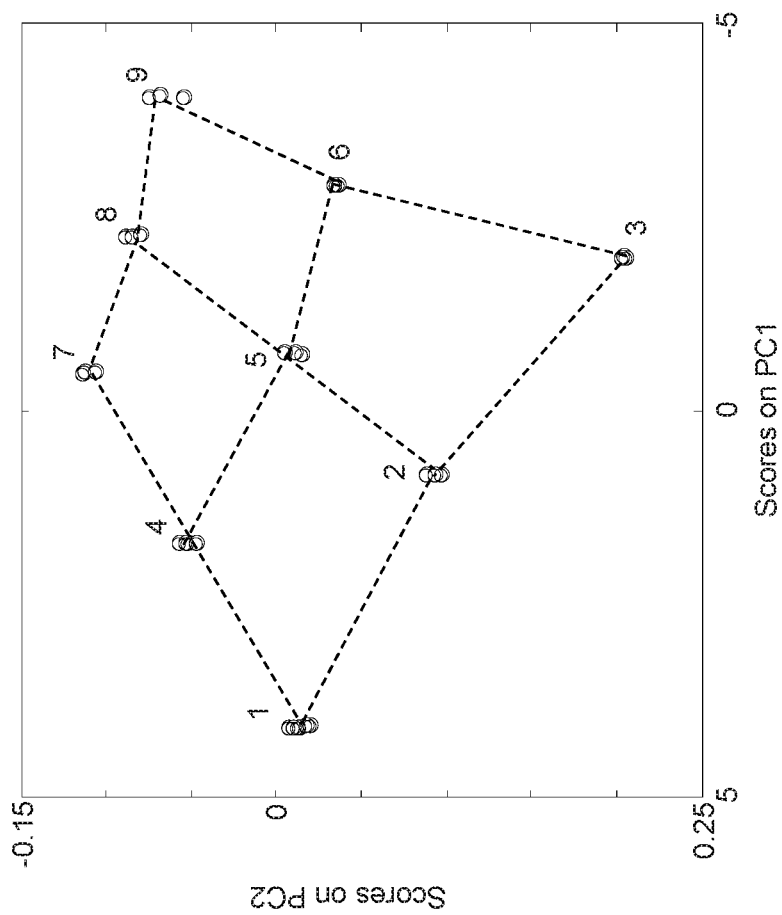
FIG. 73 depicts a scores plot of a developed PCA model illustrating spectral relation between sensor responses to the different types of contamination in the nine oil samples shown in FIG. 72.

FIG. 73 depicts a scores plot of a developed PCA model showing Principal component 1 (PC1) vs. Principal component 2 (PC2) illustrating spectral relation between sensor responses to the different types of contamination in the nine oil samples shown in FIG. 72. As shown in FIG. 73, the experimental grid from FIG. 72 is visible in the scores plot, which indicates an ability to discriminate between all nine samples using the PCA. For example, the experimental grid in FIG. 73 is a distorted version of the grid shown in FIG. 72, but all nine points are visible in the distorted view and have different coordinates in the scores plot.

In the experimental methodology, the TBN and water levels were further determined or predicted using a multivariate regression technique. FIG. 74A plots the results of predicted and actual TBN levels for the different samples of oil tested using the multivariable resonant sensor. FIG. 74B plots the residual error of the TBN prediction using the multivariable resonant sensor. The results shown in FIGS. 74A and 74B illustrate that the multivariable sensor quantifies TBN in oil samples having different amounts of water therein with less than ±0.5 mg KOH/g residual error. Therefore, the multivariable resonant sensor is able to predict a TBN level (e.g., a base concentration) in an oil sample, regardless of whether or not the oil sample includes water or acidic components therein.

Figures 75A, 75B:
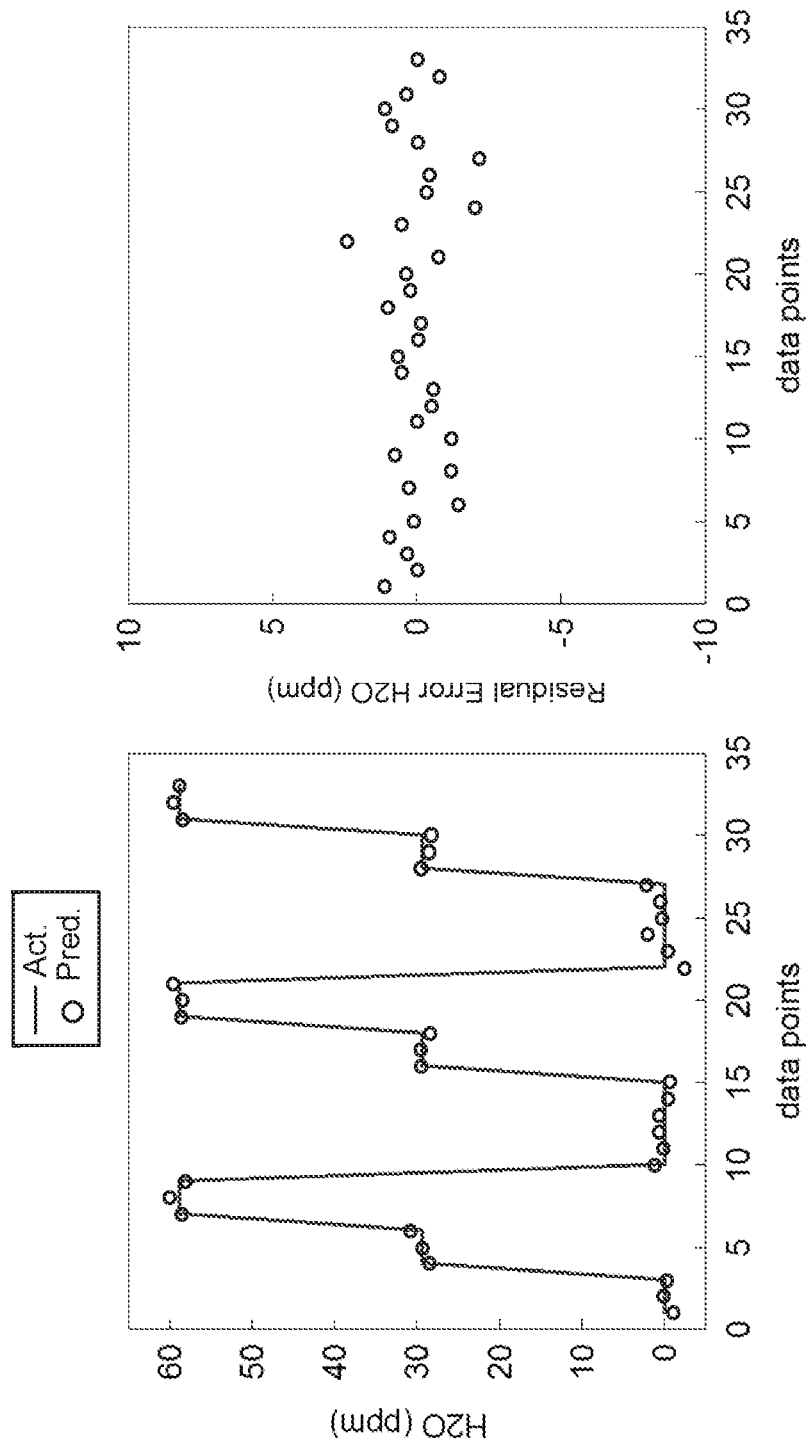
FIGS. 75A-B plot the results of predicted and actual water concentrations in oil for the different samples of oil tested using the multivariable resonant sensor and the residual error of the water concentration prediction, respectively.

FIG. 75A shows the results of predicted and actual concentrations of water in oil for the different samples of oil tested using the multivariable resonant sensor at different TBN levels. FIG. 75B plots the residual error of the water concentration prediction using the multivariable resonant sensor. The results shown in FIGS. 75A and 75B illustrate that the multivariable sensor quantifies water concentrations in oil samples having different amounts of basic components therein with less than ±10 ppm residual error. Therefore, the multivariable resonant sensor is able to predict a concentration of water in an oil sample, regardless of whether or not the oil sample includes variable concentrations of base additives or other basic components therein. Furthermore, the single multivariable resonant sensor is able to predict both a water concentration and a TBN level of an oil sample based on a single spectral impedance response of the sensor in contact with the oil.

In one embodiment, a sensing system is provided that includes a sensor and one or more processors. The sensor includes a sensing region configured to be in contact with an industrial fluid. The sensing region includes electrodes and a sensing region circuit electrically connected to the electrodes. The sensing region circuit is configured to generate an electrical stimulus having multiple different frequencies that are applied to the industrial fluid via the electrodes. The one or more processors are configured to receive one or more electrical signals from the sensor representative of an impedance response of the sensing region to the electrical stimulus. The one or more processors are configured to analyze the impedance response and determine at least one of a contaminant concentration of an external contaminant in the industrial fluid, an acid concentration of acidic components in the industrial fluid, or a base concentration of basic components in the industrial fluid based on the impedance response.

Optionally, the one or more processors are configured to determine the contaminant concentration, the acid concentration, and the base concentration in the industrial fluid based on the impedance response.

Optionally, the sensing region of the sensor is configured to be disposed with the industrial fluid within a reservoir of a machine having moving parts. The industrial fluid lubricates the moving parts of the machine.

Optionally, the industrial fluid is at least one of an oil, a fuel, a gas, or a solvent.

Optionally, the one or more processors are configured to analyze the impedance response by extracting resonance parameters of the impedance response. The resonance parameters include one or more of a frequency position (Fp) and magnitude (Zp) of a real part of the resonant impedance spectral response, a resonant frequency (F1) and antiresonant frequency (F2) of an imaginary part of the resonant impedance spectral response, an impedance magnitude (Z1) at the resonant frequency (F1) and an impedance magnitude (Z2) at the antiresonant frequency (F), and a zero-reactance frequency (Fz) at the imaginary part of the resonant impedance spectral response.

Optionally, the sensing region circuit includes an inductor-capacitor-resistor (LCR) resonant circuit.

Optionally, the sensing region includes a sensing material.

Optionally, the one or more processors are configured to analyze the impedance response by extracting resonance parameters of the impedance response. The one or more processors are configured to determine at least one of the contaminant concentration or the acid concentration of the industrial fluid by comparing the resonance parameters that are extracted to known resonance parameters associated with at least one of different contaminant concentrations, different acid concentrations, or different base concentrations in the industrial fluid.

Optionally, the one or more processors are configured to determine the acid concentration of the industrial fluid within one of at least three different acid levels. The one or more processors are further configured to determine the contaminant concentration of the industrial fluid within one of at least three different contaminant levels.

Optionally, the external contaminant is water.

Optionally, the industrial fluid is an oil and at least some of the acidic components in the industrial fluid are products of oxidation of the oil. The one or more processors are configured to determine the acid concentration in the industrial fluid to estimate at least one of an amount of acidic contamination of the oil, an amount of the basic components in the oil, or an amount of degradation of the oil.

In another embodiment, a method is provided that includes applying an electrical stimulus having multiple different frequencies to an industrial fluid via electrodes of a sensor that is in contact with the industrial fluid. The electrical stimulus is generated by a sensing region circuit of the sensor that is electrically connected to the electrodes. The method also includes receiving one or more electrical signals from the sensor at one or more processors. The one or more electrical signals are representative of an impedance response of the sensor to the electrical stimulus. The method further includes analyzing the impedance response using the one or more processors to determine at least one of a contaminant concentration of an external contaminant in the industrial fluid, an acid concentration of acidic components in the industrial fluid, or a base concentration of basic components in the industrial fluid based on the impedance response.

Optionally, the impedance response is analyzed by extracting resonance parameters of the impedance response. The method further includes comparing the resonance parameters that are extracted to known resonance parameters associated with at least one of different contaminant concentrations, different acid concentrations, or different base concentrations in the industrial fluid.

Optionally, the impedance response is analyzed to determine both the contaminant concentration and the acid concentration in the industrial fluid based on the impedance response.

Optionally, the impedance response is analyzed to determine both the contaminant concentration and the base concentration in the industrial fluid based on the impedance response.

Optionally, the impedance response is analyzed to determine both the contaminant concentration and a concentration of an additive package in the industrial fluid based on the impedance response.

In another embodiment, a sensing system is provided that includes a sensor and one or more processors. The sensor includes a sensing region configured to be in contact with an industrial fluid. The sensing region includes electrodes and a sensing region circuit electrically connected to the electrodes. The sensing region circuit includes an inductor-capacitor-resistor (LCR) resonant circuit. The sensing region circuit is configured to generate an electrical stimulus having multiple different frequencies that is applied to the industrial fluid via the electrodes. The one or more processors are configured to receive one or more electrical signals from the sensor representative of an impedance response of the sensing region to the electrical stimulus. The one or more processors are configured to analyze the impedance response and determine a contaminant concentration of an external contaminant in the industrial fluid, a base concentration of basic components in the industrial fluid, and an acid concentration of acidic components in the industrial fluid based on the impedance response.

Optionally, the electrodes in the sensing region include at least one pair of electrodes.

Optionally, the sensing region circuit includes multiple LCR resonant circuits that have different resonant frequencies. The electrical stimulus applied to the industrial fluid has a spectral frequency range that includes the different resonant frequencies of the multiple LCR resonant circuits.

Optionally, the industrial fluid is an oil and at least some of the acidic components in the industrial fluid are products of oxidation of the oil. The one or more processors are configured to determine the acid concentration in the industrial fluid to estimate at least one of an amount of acidic contamination of the oil, an amount of depletion of the basic components in the oil, or an amount of degradation of the oil.

Optionally, the sensing region includes a sensing material.

Optionally, the industrial fluid is an oil and at least some of the basic components in the industrial fluid are additives added to the oil. The one or more processors are configured to determine the base concentration in the industrial fluid to estimate at least one of an amount of depletion of the additives, an amount of basic contamination of the oil, or an amount of degradation of the oil.

The term "multivariable sensor" is referred to herein as a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" refers to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the LCR sensor. In addition to measuring the impedance spectrum in the form of Z-parameters, S-parameters, and other parameters, the impedance spectrum (for example, both real and imaginary parts) may be analyzed simultaneously using various parameters for analysis, such as, the frequency of the maximum of the real part of the impedance ($F_p$), the magnitude of the real part of the impedance ($Z_p$), the resonant frequency of the imaginary part of the impedance ($F_1$), the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra may also be called "features" or "descriptors." The appropriate selection of features is performed from all potential features that can be calculated from spectra.

As used herein the term "sensing materials and sensing films" includes, but is not limited to, materials deposited onto a transducer's electronics circuit components, such as LCR circuit components to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensing system comprising:
a sensor including a sensing region configured to be in contact with an oil, the sensing region including electrodes and a sensing region circuit electrically connected to the electrodes, the sensing region circuit configured to generate an electrical stimulus having multiple different frequencies that are applied to the oil via the electrodes; and
one or more processors configured to receive one or more electrical signals from the sensor representative of an impedance response of the sensing region to the electrical stimulus, the one or more processors configured to analyze the impedance response to extract resonance parameters of the impedance response and to determine, based on the resonance parameters that are extracted, (i) a contaminant concentration of an external contaminant in the oil and (ii) at least one of an acid concentration of acidic components in the oil or a base concentration of basic components in the oil.

2. The sensing system of claim 1, wherein the one or more processors are configured to determine the contaminant concentration, the acid concentration, and the base concentration in the oil based on the impedance response.

3. The sensing system of claim 1, wherein the sensing region of the sensor is configured to be disposed with the oil within a reservoir of a machine having moving parts, the oil lubricating the moving parts of the machine.

4. The sensing system of claim 1, wherein the resonance parameters extracted from the impedance response include one or more of a frequency position (Fp) and magnitude (Zp) of a real part of the resonant impedance spectral response, a resonant frequency (F1) and antiresonant frequency (F2) of an imaginary part of the resonant impedance spectral response, an impedance magnitude (Z1) at the resonant frequency (F1) and an impedance magnitude (Z2) at the antiresonant frequency (F2), and a zero-reactance frequency (Fz) at the imaginary part of the resonant impedance spectral response.

5. The sensing system of claim 1, wherein the sensing region circuit includes an inductor-capacitor-resistor (LCR) resonant circuit.

6. The sensing system of claim 1, wherein the sensing region includes a sensing material.

7. The sensing system of claim 1, wherein the one or more processors are configured to determine the contaminant concentration and at least one of the acid concentration or the base concentration in the oil by comparing the resonance parameters that are extracted to known resonance parameters associated with different contaminant concentration and at least one of different acid concentrations or different base concentrations in the oil.

8. The sensing system of claim 1, wherein the one or more processors are configured to determine the acid concentration in the oil within one of at least three different acid levels, the one or more processors further configured to determine the contaminant concentration in the oil within one of at least three different contaminant levels.

9. The sensing system of claim 1, wherein the external contaminant is water.

10. The sensing system of claim 1, wherein at least some of the acidic components in the oil are products of oxidation of the oil, the one or more processors configured to determine the acid concentration in the oil to estimate at least one of an amount of acidic contamination of the oil, an amount of the basic components in the oil, or an amount of degradation of the oil.

11. The sensing system of claim 1, wherein the sensing region circuit of the sensing region of the sensor includes multiple inductor-capacitor-resistor (LCR) resonant circuits that have different resonant frequencies, the electrical stimulus applied to the oil having a spectral frequency range that includes the different resonant frequencies of the multiple LCR resonant circuits.

12. A method comprising:
applying electrical stimulus having multiple different frequencies to an industrial fluid via electrodes of a sensor that is in contact with the industrial fluid, the industrial fluid including one or more of an oil, a fuel, or a solvent, the electrical stimulus generated by a sensing region circuit of the sensor that is electrically connected to the electrodes;
receiving one or more electrical signals from the sensor at one or more processors, the one or more electrical signals representative of an impedance response of the sensor to the electrical stimulus; and
analyzing the impedance response using the one or more processors to extract resonance parameters of the impedance response and to determine, based on the resonance parameters that are extracted, (i) a contaminant concentration of an external contaminant in the industrial fluid and (ii) at least one of an acid concentration of acidic components in the industrial fluidal or a base concentration of basic components in the industrial fluid.

13. The method of claim 12, wherein the method further comprising comparing the resonance parameters that are extracted to known resonance parameters associated with different contaminant concentrations and at least one of different acid concentrations, or different base concentrations in the industrial fluid.

14. The method of claim 12, wherein the impedance response is analyzed to determine both the contaminant concentration and the acid concentration in the industrial fluid based on the impedance response.

15. The method of claim 12, wherein the impedance response is analyzed to determine both the contaminant concentration and the base concentration in the industrial fluid based on the impedance response.

16. The method of claim 12, wherein the impedance response is analyzed to determine both the contaminant concentration and a concentration of an additive package in the industrial fluid based on the impedance response.

17. A sensing system comprising:
a sensor including a sensing region configured to be in contact with an oil, the sensing region including electrodes and a sensing region circuit electrically connected to the electrodes, the sensing region circuit including an inductor-capacitor-resistor (LCR) resonant circuit, the sensing region circuit configured to generate an electrical stimulus having multiple different frequencies that is applied to the oil via the electrodes; and
one or more processors configured to receive one or more electrical signals from the sensor representative of an impedance response of the sensing region to the electrical stimulus, the one or more processors configured to analyze the impedance response to extract resonance parameters of the impedance response and to determine, based on the resonance parameters that are extracted, a contaminant concentration of an external contaminant in the oil, a base concentration of basic components in the oil, and an acid concentration of acidic components in the oil.

18. The sensing system of claim 17, wherein the electrodes in the sensing region include at least one pair of electrodes.

19. The sensing system of claim 17, wherein the sensing region circuit includes multiple LCR resonant circuits that have different resonant frequencies, the electrical stimulus applied to the oil having a spectral frequency range that includes the different resonant frequencies of the multiple LCR resonant circuits.

20. The sensing system of claim 17, wherein at least some of the acidic components in the oil are products of oxidation of the oil, the one or more processors configured to determine the acid concentration in the oil to estimate at least one of an amount of acidic contamination of the oil, an amount of depletion of the basic components in the oil, or an amount of degradation of the oil.

21. The sensing system of claim 17, wherein the sensing region includes a sensing material.

22. The sensing system of claim 17, wherein at least some of the basic components in the oil are additives added to the oil, the one or more processors configured to determine the base concentration in the oil to estimate at least one of an amount of depletion of the additives, an amount of basic contamination of the oil, or an amount of degradation of the oil.

* * * * *